US012312328B2

(12) United States Patent
Acker et al.

(10) Patent No.: US 12,312,328 B2
(45) Date of Patent: *May 27, 2025

(54) PYRAZOLINE DIHYDROQUINOLONES, PHARMACEUTICAL COMPOSITIONS, AND USES

(71) Applicant: Emory University, Atlanta, GA (US)

(72) Inventors: Timothy M. Acker, San Francisco, CA (US); Dennis C. Liotta, Atlanta, GA (US); Stephen F. Traynelis, Decatur, GA (US); Yao Jing, Dunwoody, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 395 days.

This patent is subject to a terminal disclaimer.

(21) Appl. No.: 17/404,579

(22) Filed: Aug. 17, 2021

(65) Prior Publication Data

US 2021/0380559 A1 Dec. 9, 2021

Related U.S. Application Data

(60) Continuation of application No. 16/053,265, filed on Aug. 2, 2018, now Pat. No. 11,117,882, which is a division of application No. 14/901,628, filed as application No. PCT/US2014/044573 on Jun. 27, 2014, now abandoned.

(60) Provisional application No. 61/840,544, filed on Jun. 28, 2013.

(51) Int. Cl.
*C07D 401/14* (2006.01)
*A61K 31/4709* (2006.01)
*A61K 31/497* (2006.01)
*A61K 45/06* (2006.01)
*C07D 401/04* (2006.01)

(52) U.S. Cl.
CPC ........ *C07D 401/14* (2013.01); *A61K 31/4709* (2013.01); *A61K 31/497* (2013.01); *A61K 45/06* (2013.01); *C07D 401/04* (2013.01); Y02A 50/30 (2018.01)

(58) Field of Classification Search
CPC ................ C07D 401/14; C07D 401/04; A61K 31/4709; A61K 31/497; A61K 45/06; Y02A 50/30
See application file for complete search history.

(56) References Cited

U.S. PATENT DOCUMENTS

| 5,252,584 | A | 10/1993 | Carling |
| 8,178,667 | B2 | 5/2012 | Lindsley |
| 11,117,882 | B2 | 9/2021 | Acker |
| 2011/0082137 | A1* | 4/2011 | Giovannini ............. A61P 25/00 544/118 |
| 2021/0017149 | A1 | 1/2021 | Liotta |

FOREIGN PATENT DOCUMENTS

| CN | 106568976 | 5/2018 |
| WO | 2009006437 | 1/2009 |
| WO | 2009137843 | 11/2009 |
| WO | 2010088408 | 8/2010 |
| WO | 2010088414 | 8/2010 |
| WO | WO-2010088408 A2 * | 8/2010 ........... C07D 209/08 |

OTHER PUBLICATIONS

Acker, T. et al., "Mechanism for noncompetitive inhibition by novel GluN2C/D N-methyl-D-aspartate receptor subunit-selective modulators", Molecular Pharmacology, 2011, vol. 80, No. 5, pp. 782-795.

Acker et al., "Structure-Activity Relationships and Pharmacophore Model of a Noncompetive Pyrazoline Containing Class of GluN2C/GluN2D Selective Antagonists", Journal of Medicinal Chemistry, 2013, vol. 56, No. 16, pp. 6434-6456.

Chen, L. et al., "Discovering severe acute respiratory syndrome coronavirus 3CL protease inhibitors: cirtual screening, surface plasmon resonance, and fluororescence resonance energy transfer assays", Journal of Biomolecular Screening, 2006, vol. 11, No. 8, pp. 915-921.

Desos, P. et al., "Structure-activity relationships in a series of 2(1H)-quinolones bearing different acidic function in the 3-position: 6,7-dicholor-2(1H)-oxoquinoline-3-phosphonic acid, a new potent and selective AMPA/Kainate antagonist with neuroprotective properties", Journal of Medicinal Chemistry, 1996, vol. 39, No. 1, pp. 197-206.

(Continued)

*Primary Examiner* — Jeffrey S Lundgren
*Assistant Examiner* — Ibrahim D Bori
(74) *Attorney, Agent, or Firm* — Emory Patent Group

(57) ABSTRACT

This disclosure relates to pyrazoline dihydroquinolone derivatives, pharmaceutical compositions, and uses. In certain embodiments, the compounds are selective NMDA receptor inhibitors and are useful in therapeutic methods related thereto. In certain embodiments, this disclosure relates to pharmaceutical compositions comprising a compound of the following formula:

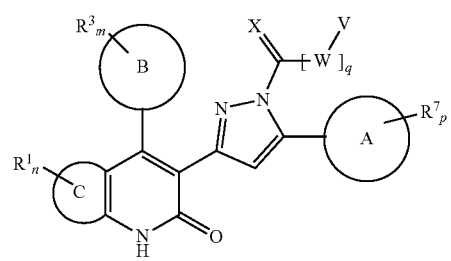

Formula I or salts, esters, or prodrugs thereof, as provided herein.

22 Claims, 21 Drawing Sheets

(56) References Cited

OTHER PUBLICATIONS

Kadieva M.G. et al., "Antagonists of AMPA/KA and NMDA (glycine site) glutamate receptors", Pharmaceutical Chemistry Journal, 2008, vol. 42, No. 2, pp. 72-80.

Podvinec, M., et al., "Novel inhibitors of dengue virus methyltransferase: discovery by in vitro-driven virtual screening on a desktop computer grid", Journal of Medicinal Chemistry, 2010, vol. 53, No. 4, pp. 1483-1495 and supporting information.

* cited by examiner

Electronics are optimal with para-Br or para-Cl

Configuration confers potency; Negative charge not required (S) Enantiomer preferred Functional groups are tolerated Potency correlates with para-σ values at GluN2C/D-containing receptors when $R_1$ is Cl

| DQP- | R$_6$ | R$_7$ | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|
| 1 | H | H | - | - | NE | NE | 86 | 88 |
| 2 | H | F | 9 | 6 | 128 | 87 | 23 | 14 |
| 3 | H | Cl | - | - | NE | NE | 5.5 | 4.5 |
| 4 | H | Br | - | 7 | NE | 22 | 3.6 | 3.1 |
| 5 | H | NO$_2$ | 85 | 42 | 91 | 45 | 0.9 | 1.1 |
| 6 | H | COOH | - | - | NE | NE | NE | NE |
| 7 | H | COOMe | - | - | NE | NE | 93 | 32 |
| 8 | H | CF$_3$ | 20 | 13 | 80 | 54 | 5 | 4.1 |
| 9 | H | OMe | 9 | 9 | 197 | 187 | 28 | 21 |
| 10 | H | NMe$_2$ | - | - | NE | NE | 39 | 19 |
| 11 | -OCH$_2$O- | | - | 4 | NE | 90 | 23 | 23 |

| DQP- | $R_5$ | $R_6$ | $R_7$ | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|---|
| 12 | H | F | H | 4 | 4 | 114 | 111 | 32 | 26 |
| 13 | H | Cl | H | 5 | 5 | 43 | 43 | 14 | 8.8 |
| 14 | H | Br | H | 6 | 7 | 24 | 30 | 6.8 | 4.0 |
| 15 | H | OMe | H | 9 | 7 | 162 | 129 | 38 | 19 |
| 16 | H | NO$_2$ | H | - | 6 | NE | 109 | 22 | 19 |
| 17 | F | H | H | 6 | 4 | 281 | 203 | 54 | 88 |
| 18 | Cl | H | H | 7 | 6 | 109 | 92 | 26 | 16 |
| 19 | Br | H | H | 8 | 6 | 102 | 80 | 21 | 13 |
| 20 | Cl | H | Cl | 9 | 9 | 28 | 28 | 3.4 | 3.1 |
| 99 | OMe | H | H | - | 4 | NE | 251 | 43 | 65 |

| DQP- | R$_3$ | R$_7$ | 2A IC$_{50}$ / 2D IC$_{50}$ | 2B IC$_{50}$ / 2D IC$_{50}$ | GluN2A IC$_{50}$ (µM) | GluN2B IC$_{50}$ (µM) | GluN2C IC$_{50}$ (µM) | GluN2D IC$_{50}$ (µM) |
|---|---|---|---|---|---|---|---|---|
| 21 | Br | Br | 33 | 59 | 13 | 23 | 0.71 | 0.39 |
| 22 | Br | Cl | 34 | 79 | 10 | 23 | 0.56 | 0.29 |
| 23 | Br | F | 12 | 26 | 34 | 75 | 3.8 | 2.9 |
| 24 | Br | H | 7 | 12 | 64 | 113 | 10 | 9.1 |
| 25 | Cl | Br | 37 | 67 | 19 | 34 | 0.95 | 0.51 |
| 26 | Cl | Cl | 48 | 50 | 21 | 22 | 0.77 | 0.44 |
| 27 | Cl | F | 14 | 26 | 47 | 90 | 4.1 | 3.4 |
| 28 | Cl | H | 4 | 13 | 49 | 143 | 13 | 11 |

| DQP- | $R_2$ | $R_3$ | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|
| 29 | H | F | 36 | 98 | 21 | 57 | 1.0 | 0.58 |
| 26 | H | Cl | 48 | 50 | 21 | 22 | 0.77 | 0.44 |
| 30 | H | Me | 24 | 30 | 33 | 42 | 2.5 | 1.4 |
| 31 | H | OMe | 27 | 33 | 62 | 75 | 5 | 2.3 |
| 32 | H | CN | 22 | - | 156 | NE | 12 | 7 |
| 33 | H | CF$_3$ | 10 | 14 | 29 | 39 | 3.6 | 2.8 |
| 34 | F | H | 67 | 101 | 46 | 70 | 1.1 | 0.69 |
| 35 | Cl | H | 20 | 43 | 20 | 43 | 2.1 | 1.0 |
| 36 | Me | H | 13 | 37 | 24 | 71 | 4.0 | 1.9 |
| 37 | OMe | H | 24 | 34 | 110 | 152 | 7.8 | 4.5 |
| 38 | CN | H | - | - | NE | NE | 19 | 13 |
| 39 | CF$_3$ | H | 11 | 18 | 28 | 47 | 3.4 | 2.6 |

| DQP- | R$_2$ | R$_3$ | R$_4$ | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|---|
| 40 | F | Cl | H | 23 | 53 | 12 | 28 | 0.91 | 0.53 |
| 41 | Cl | F | H | 19 | 34 | 19 | 34 | 1.4 | 1.0 |
| 42 | Cl | Cl | H | 8 | 22 | 7.7 | 20 | 0.79 | 0.91 |
| 43 | F | F | H | 32 | 108 | 21 | 71 | 0.78 | 0.66 |
| 44 | F | H | F | 26 | 123 | 21 | 100 | 1.1 | 0.81 |
| 45 | Cl | H | Cl | 8 | 19 | 5.5 | 13 | 0.78 | 0.70 |

| DQP- | R₁ | R₂ | R₃ | 2A IC$_{50}$ / 2D IC$_{50}$ | 2B IC$_{50}$ / 2D IC$_{50}$ | GluN2A IC$_{50}$ (µM) | GluN2B IC$_{50}$ (µM) | GluN2C IC$_{50}$ (µM) | GluN2D IC$_{50}$ (µM) |
|---|---|---|---|---|---|---|---|---|---|
| 46 | CH₃ | H | Cl | 42 | 82 | 54 | 107 | 1.5 | 1.3 |
| 47 | CH₃ | F | H | 28 | 32 | 128 | 144 | 5.9 | 4.5 |
| 48 | Cl | H | Cl | 11 | 9 | 14 | 12 | 2.2 | 1.3 |
| 49 | Cl | F | H | 11 | 10 | 57 | 51 | 7.3 | 5.3 |
| 50 | F | H | Cl | 10 | 16 | 14 | 23 | 2.5 | 1.4 |
| 51 | F | F | H | 10 | 16 | 43 | 69 | 3.4 | 4.3 |
| 52 | OMe | H | Cl | 10 | 27 | 50 | 140 | 3.8 | 5.2 |
| 53 | OMe | F | H | 10 | 13 | 100 | 132 | 14 | 10 |

| DQP- | $R_1$ | $R_2$ | $R_4$ | Acyl Chain | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|---|---|
| 4 | Cl | H | Br | succinyl | - | 7 | NE | 22 | 3.6 | 3.1 |
| 54 | Cl | H | Br | fumaryl | - | - | NE | NE | 2.1 | 1.4 |
| 55 | Cl | H | Br | maleyl | 15 | 7 | 74 | 37 | 8.9 | 5 |
| 56 | Cl | H | Br | methyl succinyl | - | - | NE | NE | NE | NE |
| 57 | Cl | H | Br | glutaryl | 20 | 23 | 78 | 90 | 6.4 | 4.0 |
| 22 | H | Br | Cl | succinyl | 34 | 79 | 10 | 23 | 0.56 | 0.29 |
| 58 | H | Br | Cl | fumaryl | 23 | 63 | 4.3 | 12 | 0.20 | 0.19 |
| 59 | H | Br | Cl | maleyl | 21 | 30 | 12 | 17 | 1.0 | 0.57 |
| 60 | H | Br | Cl | methyl fumaryl | - | - | NE | NE | 59 | 95 |
| 61 | H | Br | Cl | glutaryl | 33 | 91 | 10 | 29 | 0.6 | 0.32 |
| 5 | Cl | H | NO$_2$ | succinyl | 85 | 42 | 91 | 45 | 0.9 | 1.1 |

| | | | | | | | | | | |
|---|---|---|---|---|---|---|---|---|---|---|
| 5 | Cl | H | NO₂ | ⟨structure: ketone-CH₂CH₂-COOH⟩ | 85 | 42 | 91 | 45 | 0.9 | 1.1 |
| 63 | Cl | H | NO₂ | ⟨structure: ketone-(CH₂)₃-COOH⟩ | 10 | 8 | 109 | 92 | 10 | 11 |
| 26 | H | Cl | Cl | ⟨structure: ketone-CH₂CH₂-COOH⟩ | 48 | 50 | 21 | 22 | 0.77 | 0.44 |
| 64 | H | Cl | Cl | ⟨structure: ketone-(CH₂)₃-OH⟩ | 90 | 48 | 62 | 33 | 1.7 | 0.69 |
| 65 | H | Cl | Cl | ⟨structure: ketone-CH₂CH₂-C(O)NH₂⟩ | 31 | 18 | 34 | 20 | 2.0 | 1.1 |
| 66 | H | Cl | Cl | ⟨structure: methyl ester⟩ | - | - | NE | NE | NE | NE |
| 67 | H | Cl | Cl | ⟨structure: -(CH₂)₃-COOH⟩ | 34 | 31 | 58 | 53 | 3 | 1.7 |
| 68 | H | Cl | Cl | ⟨structure: ketone-(CH₂)₂-F⟩ | - | - | NE | NE | NE | NE |

FIG. 16B

| DQP- | R$_2$ | R$_4$ | 2A IC$_{50}$ / 2D IC$_{50}$ | 2B IC$_{50}$ / 2D IC$_{50}$ | GluN2A IC$_{50}$ (μM) | GluN2B IC$_{50}$ (μM) | GluN2C IC$_{50}$ (μM) | GluN2D IC$_{50}$ (μM) |
|---|---|---|---|---|---|---|---|---|
| 26 | Cl | Cl | 48 | 50 | 21 | 22 | 0.77 | 0.44 |
| 69 (S-26) | Cl | Cl | 78 | 156 | 13 | 26 | 0.22 | 0.17 |
| 70 (R-26) | Cl | Cl | 23 | 49 | 45 | 52 | 2.1 | 1.9 |

| Receptor | Agonist (μM) | (26) I$_{TEST}$ / I$_{CONTROL}$ (mean ± SEM, %) | N | (58) I$_{TEST}$ / I$_{CONTROL}$ (mean ± SEM, %) | N |
|---|---|---|---|---|---|
| GluN1/GluN2A | 100 glutamate, 30 glycine | 89 ± 4.2* | 14 | 89 ± 2.2* | 12 |
| GluN1/GluN2B | 100 glutamate, 30 glycine | 79 ± 2.9* | 12 | 98 ± 1.9 | 12 |
| GluN1/GluN2C | 100 glutamate, 30 glycine | 21 ± 1.2* | 14 | 26 ± 1.5* | 11 |
| GluN1/GluN2D | 100 glutamate, 30 glycine | 14 ± 1.6* | 13 | 14 ± 1.6* | 13 |
| GluA1 | 100 glutamate | 97 ± 2.2 | 6 | 99 ± 1.1 | 6 |
| GluA2 | 100 glutamate | 98 ± 0.8 | 3 | 96 ± 0.9* | 4 |
| GluA3 | 100 glutamate | 99 ± 0.3 | 4 | 100 ± 1.1 | 4 |
| GluA4 | 100 glutamate | 96 ± 1.3 | 3 | 97 ± 1.5 | 4 |
| GluK1 | 100 glutamate | 97 ± 1.0 | 3 | 100 ± 4.4 | 3 |
| GluK2 | 100 glutamate | 97 ± 1.1 | 4 | 97 ± 0.6* | 4 |
| GluK2/GluK5 | 100 glutamate | 97 ± 1.3 | 3 | 95 ± 1.8 | 3 |
| Serotonin 5-HT$_{3A}$ | 3 serotonin | 95 ± 1.5* | 4 | 95 ± 1.2* | 4 |
| GABA$_A$ α$_1$β$_2$γ2s | 20 GABA | 97 ± 2.7 | 4 | 95 ± 3.1 | 4 |
| GABA$_C$ (ρ1)$^{(human)}$ | 2 GABA | 99 ± 2.1 | 4 | 97 ± 0.6* | 4 |
| Glycine α$_1$ | 50 glycine | 101 ± 1.6 | 4 | 99 ± 1.0 | 4 |
| Nicotinic α$_1$β$_1$γδ$^{(mouse)}$ | 1 acetylcholine | 94 ± 1.2* | 6 | 98 ± 0.7 | 7 |
| Nicotinic α4β2$^{(human)}$ | 10 acetylcholine | 79 ± 4.2* | 6 | 82 ± 1.7* | 5 |
| Nicotinic α3β4$^{(human)}$ | 10 acetylcholine | 77 ± 2.7* | 7 | 87 ± 2.2* | 5 |
| Nicotinic α7$^{(human)}$ | 300 acetylcholine | 82 ± 9.4 | 3 | 64 ± 7.3* | 3 |
| Nicotinic α9α10 | 100 acetylcholine | 67 ± 4.6* | 3 | 72 ± 4.7* | 4 |
| Purinergic P$_{2X2}$ $^{(human)}$ | 9 ATP | 113 ± 1.8* | 5 | 100 ± 0.9 | 4 |
| Purinergic P$_{2X2}$ | 9 ATP | 97 ± 1.2* | 5 | 96 ± 1.0* | 4 |

FIG. 18

| Test Compound | Direction | Recovery (%) | $P_{app}(10^{-6}cm/s)$ | | | Efflux Ratio |
|---|---|---|---|---|---|---|
| | | | 1 | 2 | Avg | |
| 64 | A-to-B | 43 | 2.45 | 2.48 | 2.46 | 26 |
| | B-to-A | 73 | 66.2 | 62.7 | 64.5 | |
| 26 | A-to-B | 73 | 0.47 | 0.47 | 0.47 | 55 |
| | B-to-A | 76 | 33.4 | 17.9 | 25.6 | |
| 68 | A-to-B | 43 | 4.51 | 3.24 | 3.88 | 2.5 |
| | B-to-A | 67 | 9.32 | 9.72 | 9.52 | |

FIG. 19

| Test Compound | % Remaining of initial | | | | | Half-life | $CL_{int}^{b}$ (ml/min/mg protein) |
|---|---|---|---|---|---|---|---|
| | 0 min | 10 min | 20 min | 30 min | 60 min | | |
| 64 | 100 | 52 | 31 | 24 | 6.5 | 13 | 0.110 |
| 26 | 100 | 101 | 100 | 115 | 86 | >60 | <0.02 |
| 68 | 100 | 67 | 49 | 49 | 39 | 35 | 0.040 |

FIG. 20

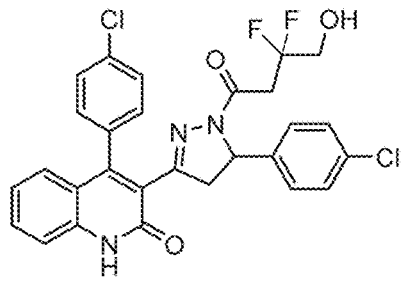

4-(4-chlorophenyl)-3-(5-(4-chlorophenyl)-1-(3,3-difluoro-4-hydroxybutanoyl)-4,5-dihydro-1H-pyrazol-3-yl)quinolin-2(1H)-one

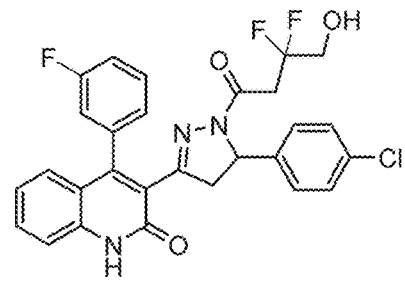

3-(5-(4-chlorophenyl)-1-(3,3-difluoro-4-hydroxybutanoyl)-4,5-dihydro-1H-pyrazol-3-yl)-4-(3-fluorophenyl)quinolin-2(1H)-one

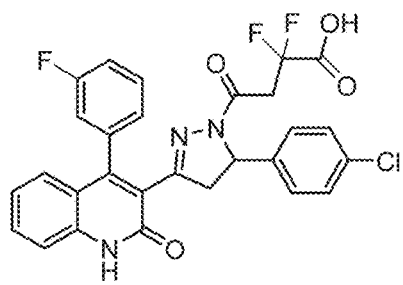

4-(5-(4-chlorophenyl)-3-(4-(3-fluorophenyl)-2-oxo-1,2-dihydroquinolin-3-yl)-4,5-dihydro-1H-pyrazol-1-yl)-2,2-difluoro-4-oxobutanoic acid

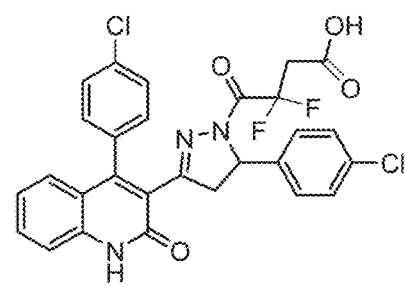

4-(5-(4-chlorophenyl)-3-(4-(4-chlorophenyl)-2-oxo-1,2-dihydroquinolin-3-yl)-4,5-dihydro-1H-pyrazol-1-yl)-3,3-difluoro-4-oxobutanoic acid

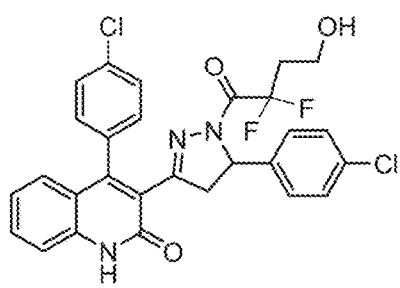

4-(4-chlorophenyl)-3-(5-(4-chlorophenyl)-1-(2,2-difluoro-4-hydroxybutanoyl)-4,5-dihydro-1H-pyrazol-3-yl)quinolin-2(1H)-one

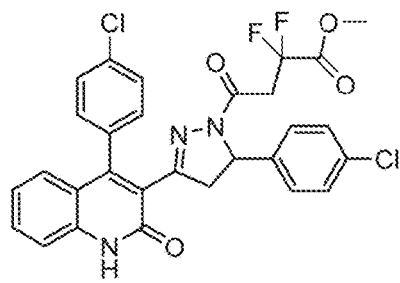

methyl 4-(5-(4-chlorophenyl)-3-(4-(4-chlorophenyl)-2-oxo-1,2-dihydroquinolin-3-yl)-4,5-dihydro-1H-pyrazol-1-yl)-2,2-difluoro-4-oxobutanoate

FIG. 21

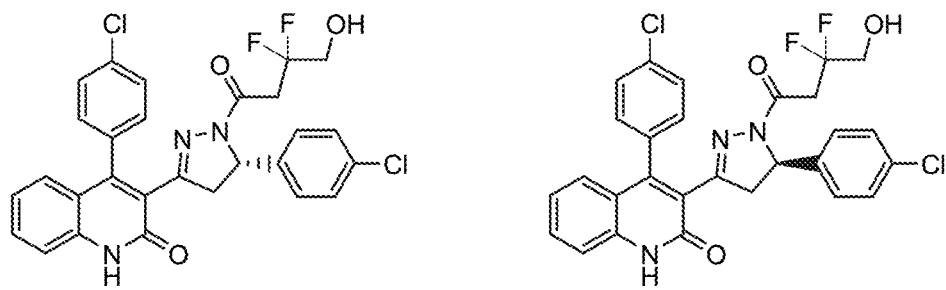

(S)-4-(4-chlorophenyl)-3-(5-(4-chlorophenyl)-1-(3,3-difluoro-4-hydroxybutanoyl)-4,5-dihydro-1H-pyrazol-3-yl)quinolin-2(1H)-one (R)-4-(4-chlorophenyl)-3-(5-(4-chlorophenyl)-1-(3,3-difluoro-4-hydroxybutanoyl)-4,5-dihydro-1H-pyrazol-3-yl)quinolin-2(1H)-one

FIG. 22

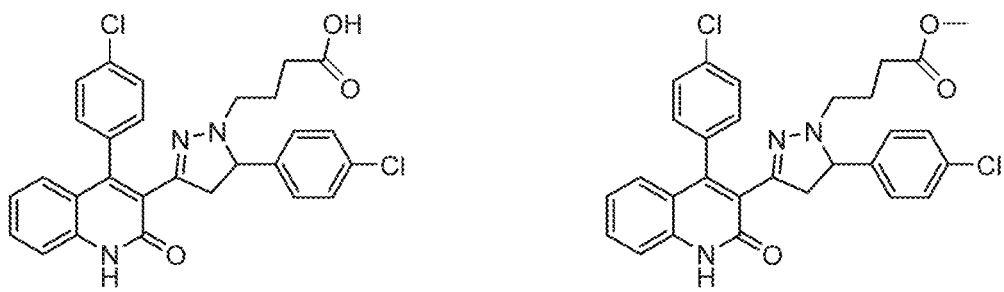

4-(5-(4-chlorophenyl)-3-(4-(4-chlorophenyl)-2-oxo-1,2-dihydroquinolin-3-yl)-4,5-dihydro-1H-pyrazol-1-yl)butanoic acid methyl 4-(5-(4-chlorophenyl)-3-(4-(4-chlorophenyl)-2-oxo-1,2-dihydroquinolin-3-yl)-4,5-dihydro-1H-pyrazol-1-yl)butanoate

FIG. 23

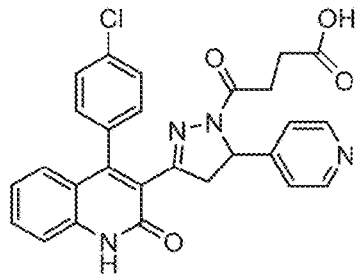

4-(3-(4-(4-chlorophenyl)-2-oxo-1,2-dihydroquinolin-3-yl)-5-(pyridin-4-yl)-4,5-dihydro-1H-pyrazol-1-yl)-4-oxobutanoic acid

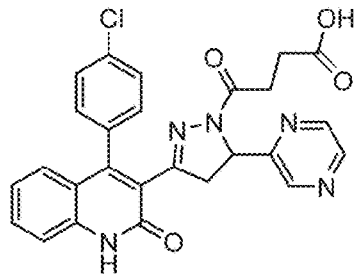

4-(3-(4-(4-chlorophenyl)-2-oxo-1,2-dihydroquinolin-3-yl)-5-(pyrazin-2-yl)-4,5-dihydro-1H-pyrazol-1-yl)-4-oxobutanoic acid

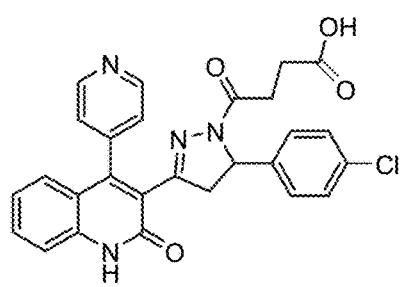

4-(5-(4-chlorophenyl)-3-(2-oxo-4-(pyridin-4-yl)-1,2-dihydroquinolin-3-yl)-4,5-dihydro-1H-pyrazol-1-yl)-4-oxobutanoic acid

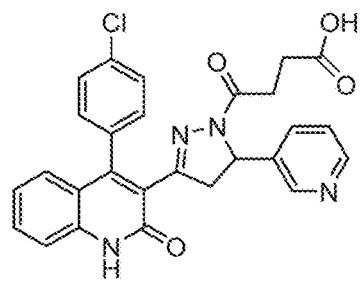

4-(3-(4-(4-chlorophenyl)-2-oxo-1,2-dihydroquinolin-3-yl)-5-(pyridin-3-yl)-4,5-dihydro-1H-pyrazol-1-yl)-4-oxobutanoic acid

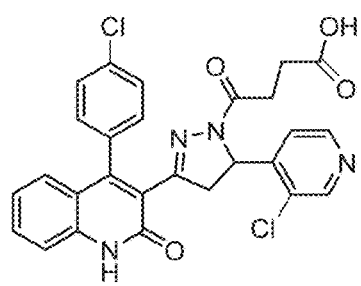

4-(3-(4-(4-chlorophenyl)-2-oxo-1,2-dihydroquinolin-3-yl)-5-(3-chloropyridin-4-yl)-4,5-dihydro-1H-pyrazol-1-yl)-4-oxobutanoic acid

FIG. 24

PYRAZOLINE DIHYDROQUINOLONES, PHARMACEUTICAL COMPOSITIONS, AND USES

CROSS REFERENCE TO RELATED APPLICATIONS

This application is a continuation of U.S. application Ser. No. 16/053,265 filed Aug. 2, 2018, which is a division of U.S. application Ser. No. 14/901,628 filed Dec. 28, 2015, which is the National Stage of International Application No. PCT/US2014/044573 filed Jun. 27, 2014, which claims priority to U.S. Provisional Application No. 61/840,544 filed Jun. 28, 2013. The entirely of each of these applications is hereby incorporated by reference for all purposes.

STATEMENT REGARDING FEDERALLY SPONSORED RESEARCH OR DEVELOPMENT

This invention was made with government support under NS071802 and NS065371 awarded by the National Institutes of Health. The government has certain rights in the invention.

BACKGROUND

Glutamatergic neurotransmission through ionotropic-glutamate receptors is the primary means of excitatory synaptic transmission in the mammalian central nervous system (CNS). The receptor family is comprised of the α-amino-3-hydroxy-5-methyl-4-isoxazolepropionate (AMPA), N-methyl-D-aspartate (NMDA), and kainate receptors. NMDA receptors are widely expressed in the central nervous system and are thought to be involved in a range of important physiological processes including axonal guidance, synaptic plasticity, and memory formation. NMDA receptors are also thought to play an important role in pathophysiological conditions including Parkinson's disease, schizophrenia, depression, and ischemia. See Traynelis et al., Pharmacol Rev, 2010, 62, 405-496; Mony et al., British Journal of Pharmacology, 2009, 157, 1301-1317; Huei-Sheng Vincent & Stuart, Journal of Neurochemistry, 2006, 97, 1611-1626; and Hallett & Standaert, Pharmacology & Therapeutics, 2004, 102, 155-174.

NMDA receptors mediate the slow component of excitatory synaptic transmission and require the binding of both glutamate and glycine for channel activation. Glycine binds to the GluN1 subunit, which has eight splice variants encoded by a single gene. The GluN2 subunits (GluN2A-D) bind glutamate, and are encoded by four distinct genes. The GluN2 subunits control many of the functional and pharmacological properties of the receptor, including agonist $EC_{50}$, single-channel open time, open probability, and deactivation-time course following removal of glutamate. NMDA receptor deactivation time course determines the time course for the slow, $Ca^{2+}$-permeable component of synaptic transmission. Typically, NMDA receptors are blocked by extracellular $Mg^{2+}$ at resting membrane potentials, and the requirements of both glutamate release and depolarization-induced relief of $Mg^{2+}$ block have led to the idea that the NMDA receptors act as coincidence detectors in the brain. The $Mg^{2+}$ $IC_{50}$ and the kinetics of block and unblock also vary according to the GluN2 subunit.

The GluN1 subunits are expressed throughout the CNS, but GluN2 subunit composition and expression vary both during development as well as anatomically. The spatially-restricted expression patterns, together with distinct functional and pharmacological differences imparted by the GluN2 subunits make NMDA receptor subunit-selective modulators of therapeutic interest for several neurological disorders, including stroke, schizophrenia, treatment-resistant depression, Parkinson's disease. See Bräuner-Osborne et al., Journal of Medicinal Chemistry, 2000, 43, 2609-2645; Chen & Lipton, J Neurochem, 2006, 97, 1611-1626; Goff et al., Schizophrenia Research, 2008, 106, 320-327, Traynelis et al., Pharmacol Rev, 2010, 62, 405-496. Subunit-selectivity restricts modulator actions to brain regions that express the subunit of interest, potentially limiting side effects that occur as a result of global NMDA receptor block. Thus, there is a need for identifying selective inhibitors.

Acker et al. report a mechanism for noncompetitive inhibition by GluN2C/D N-methyl-D-aspartate receptor subunit-selective modulators. See Molecular Pharmacology, 2011, 80, 782-795. See also WO/2010/088408, WO/2010/088414, WO/2009/137843, WO/2009/006437.

References cited herein are not an admission of prior art.

SUMMARY

This disclosure relates to pyrazoline dihydroquinolone derivatives, pharmaceutical compositions, and uses. In certain embodiments, the compounds are selective NMDA receptor inhibitors and are useful in therapeutic methods related thereto. In certain embodiments, this disclosure relates to pharmaceutical compositions comprising a compound of the following formula:

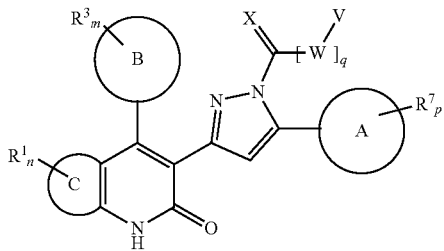

Formula I or salts, esters, or prodrugs thereof, as provided herein.

In certain embodiments, the disclosure relates to pharmaceutical compositions comprising a compound as disclosed herein or a pharmaceutically acceptable salt thereof and a pharmaceutically acceptable excipient.

In certain embodiments, the disclosure relates to methods of treating or preventing a cognitive, psychiatric, or neurodegenerative disease or condition comprising administering to a subject in need of such treatment an effective amount of a pharmaceutical composition as described herein. In certain embodiments, the disease or condition is cognitive impairment, a neurodegenerative disease, pain, depression, schizophrenia, attention deficit hyperactivity disorder, ischemia, or addiction.

In certain embodiments, the neurodegenerative disease is Alzheimer's disease, mild cognitive impairment, or Parkinson's disease. In certain embodiments, this disclosure relates to therapeutic methods disclosed herein wherein pharmaceutical compositions are administered in combination with a second active agent. In certain embodiments, the second active agent is an antidepressant or antipsychotic.

In certain embodiments, the disclosure relates to compounds disclosed herein for use in treating or preventing a cognitive, psychiatric, or neurodegenerative disease or condition disclosed herein. In certain embodiments, the disclosure relates to the use of compounds disclosed herein for the manufacture of a medicament for treating or preventing a cognitive, psychiatric, or neurodegenerative disease or condition disclosed herein.

BRIEF DESCRIPTION OF THE DRAWINGS

FIG. 16B shows a table containing data for evaluation activity of derivatives with certain acyl chain modifications.

FIG. 18 shows a table containing data for evaluation of off-target responses for compounds (26) 997-23 and (58) 997-33. Agonist-evoked currents were recorded from the receptors listed using the Xenopus laevis oocyte expression system under two-electrode voltage clamp (VHOLD=−30 to −60 mV) in the absence and presence of 3 μM (26) 997-23 or 3 μM (58) 997-33. The cDNA origin used was rat unless otherwise indicated.

FIG. 19 shows a table containing data for MDR1-MDCK permeability of certain embodiments. The $P_{app}$ and efflux ratio were calculated as described in the Methods. Compounds displaying a $P_{app}<3.0\times10^{-6}$ cm/s and efflux ratio >10 are interpreted to have a low potential for crossing the BBB. Compounds with Papp $>3.0\times10^{-6}$ cm/s and an efflux ratio <10 are expected to have high brain penetration. See Wang et al., International Journal of Pharmaceutics, 2005, 288, 349-359.

FIG. 20 shows a table containing data for human microsomal stability of certain embodiments. a Half-life was calculated based on $t_{1/2}=0.693/k$, where k is the elimination rate constant based on the slope of the natural logarithm percent remaining versus incubation time. b Intrinsic clearance ($CL_{int}$) was calculated on $CL_{int}=k/P$, where k is the elimination rate constant and P is the protein concentration in the incubation.

FIG. 21 illustrates certain embodiments of the disclosure. Testing indicated 4-(4-chlorophenyl)-3-(5-(4-chlorophenyl)-1-(3,3-difluoro-4-hydroxybutanoyl)-4,5-dihydro-1H-pyrazol-3-yl)quinolin-2(1H)-one derivative has an inhibition $IC_{50}$ of 1.6 and 0.8 (μM) for GluN2C and GluN2D respectively and 4-(5-(4-chlorophenyl)-3-(4-(3-fluorophenyl)-2-oxo-1,2-dihydroquinolin-3-yl)-4,5-dihydro-1H-pyrazol-1-yl)-2,2-difluoro-4-oxobutanoic acid has an inhibition $IC_{50}$ of 0.6 and 0.5 (μM) for GluN2C and GluN2D respectively. Testing indicated 4-(5-(4-chlorophenyl)-3-(4-(4-chlorophenyl)-2-oxo-1,2-dihydroquinolin-3-yl)-4,5-dihydro-1H-pyrazol-1-yl)-3,3-difluoro-4-oxobutanoic acid has an inhibition $IC_{50}$ of 0.39 and 0.05 (μM) for GluN2C and GluN2D, respectively.

FIG. 22 illustrates two enantiomers. Testing indicated (S)-4-(4-chlorophenyl)-3-(5-(4-chlorophenyl)-1-(3,3-difluoro-4-hydroxybutanoyl)-4,5-dihydro-1H-pyrazol-3-yl) quinolin-2(1H)-one has an inhibition $IC_{50}$ of 1.4 and 0.6 (μM) for GluN2C and GluN2D respectively. Testing indicated (R)-4-(4-chlorophenyl)-3-(5-(4-chlorophenyl)-1-(3,3-difluoro-4-hydroxybutanoyl)-4,5-dihydro-1H-pyrazol-3-yl) quinolin-2(1H)-one has an inhibition $IC_{50}$ of 8.5 and 3.6 (μM) for GluN2C and GluN2D, respectively.

FIG. 23 illustrates certain embodiments of the disclosure. Testing indicated 4-(5-(4-chlorophenyl)-3-(4-(4-chlorophenyl)-2-oxo-1,2-dihydroquinolin-3-yl)-4,5-dihydro-1H-pyrazol-1-yl)butanoic acid has an inhibition $IC_{50}$ of 3 and 1.7 (μM) for GluN2C and GluN2D, respectively.

FIG. 24 illustrated certain embodiments of the disclosure. Testing indicated 4-(5-(4-chlorophenyl)-3-(2-oxo-4-(pyridin-4-yl)-1,2-dihydroquinolin-3-yl)-4,5-dihydro-1H-pyrazol-1-yl)-4-oxobutanoic acid has an inhibition $IC_{50}$ of 15 and 8.1 (μM) for GluN2C and GluN2D, respectively.

DETAILED DESCRIPTION

Figure 1A:
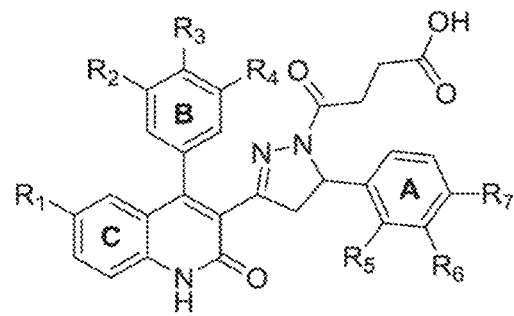
FIG. 1A illustrates certain embodiments and substituent effects of A-ring. The structure of a general analogue with numbered substituents is shown.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

Unless specifically designated by a specific structural character, chemical formulas as provided herein that have chiral centers are intended to encompass racemic, enantiomeric, and diastereomeric forms.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, indolizinyl, indazolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e., —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, or heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry textbooks, such as those provided in March's Advanced Organic Chemistry: Reactions, Mechanisms, and Structure, Wiley, 6th Edition (2007) Michael B. Smith, or Domino Reactions in Organic Synthesis, Wiley (2006) Lutz F. Tietze, which are hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Pyrazoline Dihydroquinolone Derivatives

In certain embodiments, this disclosure relates to pyrazoline dihydroquinolone derivatives as provided in any formula described herein. In certain embodiments, the pyrazoline dihydroquinolone derivative is a compound of the following formula:

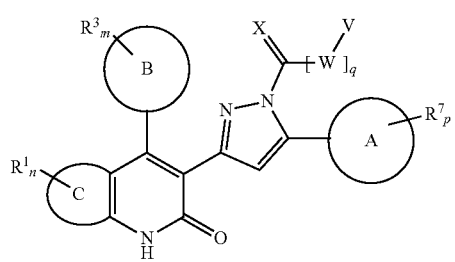

Formula I or salts, esters, or prodrugs thereof, wherein
rings A, B, or C are each individually and independently aryl, cycloalkyl, or heterocyclyl;
dotted line represents a single or double bond;
n, m, or p are each individually and independently 0, 1, 2, 3, or 4;
V is (C=Y)Z, $SO_3H$, $SO_2NH$, or $OSO_3H$;
W is at each occurrence $CH_2$, $CF_2$, $CH_2CH_2$, $CH_2CH_2CH_2$, $CF_2CH_2$, $CH_2CF_2$, CH, CH=CH, C=O, O, S, or NH;
q is 1, 2, or 3;
X or Y are each individually and independently O, S, NH, N-alkyl, or two hydrogens each of which are singly bonded to the adjacent C, or two fluoros each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^3$, and $R^7$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, W is $CH_2$ and q is 2.
In certain embodiments, W is $CH_2$ and q is 3.
In certain embodiments, X is two hydrogens each of which are singly bonded to the adjacent C, Y is O, and Z is halogen, OH, O-alkyl, or O-alkanoyl.
In certain embodiments, X is O, Y is two hydrogens each of which are singly bonded to the adjacent C, and Z is halogen, OH, O-alkyl, or alkanoyl.
In certain embodiments, X is O, Y is two hydrogens each of which are singly bonded to the adjacent C, and Z is halogen, $NH_2$, NH-alkyl, or NH-alkanoyl.
In certain embodiments, X is O, Y is two fluoros each of which are singly bonded to the adjacent C and Z is halogen, OH, O-alkyl, alkanoyl, or $NH_2$.
In certain embodiments, rings A, B, and C are phenyl.
In certain embodiments, the A ring is para-substituted with $R^7$, wherein $R^7$ is a halogen.
In certain embodiments, the B ring is para-substituted with $R^3$, wherein $R^3$ is a halogen.
In certain embodiments, the C ring is para-substituted to the nitrogen in the amide with $R^1$, wherein $R^1$ is a halogen.
In certain embodiments, $R^1$ is hydrogen, $R^3$ and $R^7$ are halogen.
In certain embodiments, the compounds for formula II have formula IA or IB,

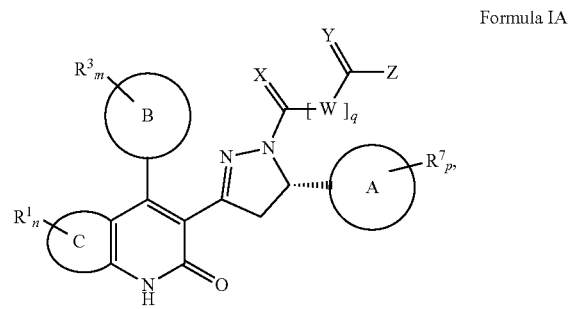

Formula IA

-continued

Formula IB

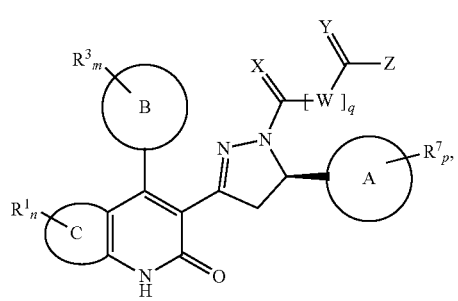

or salts, esters, or prodrugs thereof. In certain embodiments, compositions comprised the compounds of Formula IA or IB in greater than 55%, 65%, 75%, 85%, or 95% enantiomeric excess or diastereomeric excess.

In certain embodiments, the pyrazoline dihydroquinolone derivative is a compound of the following formula:

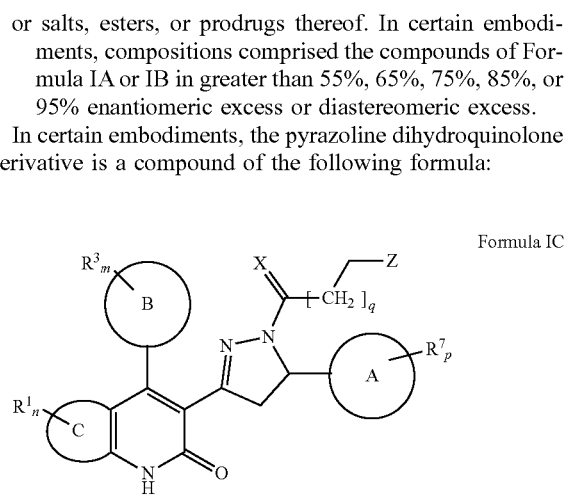

Formula IC or salts, esters, or prodrugs thereof, wherein
rings A, B, or C are each individually and independently aryl, cycloalkyl, or heterocyclyl;
n, m, or p are each individually and independently 0, 1, 2, 3, or 4;
q is 1, 2, or 3;
X is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^3$, and $R^7$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, q is 2.

In certain embodiments, X is two hydrogens each of which are singly bonded to the adjacent C and Z is halogen, OH, O-alkyl, or O-alkanoyl.

In certain embodiments, X is O and Z is halogen, OH, O-alkyl, or alkanoyl.

In certain embodiments, rings A, B, and C are phenyl.

In certain embodiments, the A ring is para-substituted with $R^7$, wherein $R^7$ is a halogen.

In certain embodiments, the B ring is para-substituted with $R^3$, wherein $R^3$ is a halogen.

In certain embodiments, the C ring is para-substituted to the nitrogen in the amide with $R^1$, wherein $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

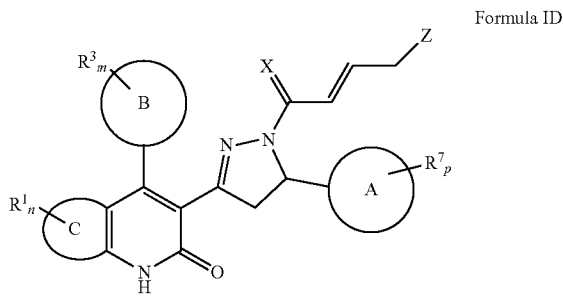

Formula ID or salts, esters, or prodrugs thereof, wherein
rings A, B, or C are each individually and independently aryl, cycloalkyl, or heterocyclyl;
n, m, or p are each individually and independently 0, 1, 2, 3, or 4;
X is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^3$, and $R^7$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is two hydrogens each of which are singly bonded to the adjacent C and Z is halogen, OH, O-alkyl, or O-alkanoyl.

In certain embodiments, X is O and Z is halogen, OH, O-alkyl, or alkanoyl.

In certain embodiments, rings A, B, and C are phenyl.

In certain embodiments, the A ring is para-substituted with $R^7$, wherein $R^7$ is a halogen.

In certain embodiments, the B ring is para-substituted with $R^3$, wherein $R^3$ is a halogen.

In certain embodiments, the C ring is para-substituted with $R^1$ compared to the nitrogen, wherein $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

Formula IE

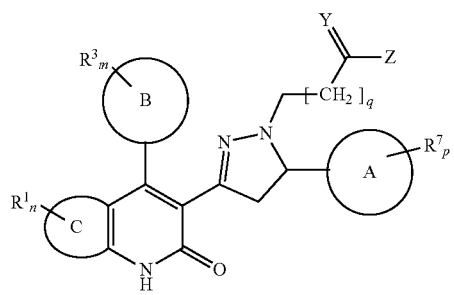

or salts, esters, or prodrugs thereof, wherein
rings A, B, or C are each individually and independently aryl, cycloalkyl, or heterocyclyl;
n, m, or p are each individually and independently 0, 1, 2, 3, or 4;
q is 1, 2, or 3;
Y is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^3$, and $R^7$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethyl-amino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is O and Z is halogen, OH, O-alkyl, or O-alkanoyl.

In certain embodiments, Y is two hydrogens each of which are singly bonded to the adjacent C and Z is halogen, OH, O-alkyl, or alkanoyl.

In certain embodiments, rings A, B, and C are phenyl.

In certain embodiments, the A ring is para-substituted with $R^7$, wherein $R^7$ is a halogen.

In certain embodiments, the B ring is para-substituted with $R^3$, wherein $R^3$ is a halogen.

In certain embodiments, the C ring is para-substituted to the nitrogen in the amide with $R^1$, wherein $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

Formula IF

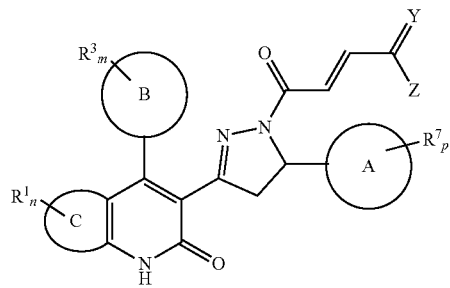

or salts, esters, or prodrugs thereof, wherein
rings A, B, or C are each individually and independently aryl, cycloalkyl, or heterocyclyl;
n, m, or p are each individually and independently 0, 1, 2, 3, or 4;
Y is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^1$, R$^3$, and R$^7$ are optionally substituted with one or more, the same or different R$^{10}$;

R$^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Y is O and Z is halogen, OH, O-alkyl, or O-alkanoyl.

In certain embodiments, Y is two hydrogens each of which are singly bonded to the adjacent C and Z is halogen, OH, O-alkyl, or alkanoyl.

In certain embodiments, rings A, B, and C are phenyl.

In certain embodiments, the A ring is para-substituted with R$^7$, wherein R$^7$ is a halogen.

In certain embodiments, the B ring is para-substituted with R$^3$, wherein R$^3$ is a halogen.

In certain embodiments, the C ring is para-substituted to the nitrogen of the amide with R$^1$, wherein R$^1$ is a halogen.

In certain embodiments, R$^1$ is hydrogen, R$^3$ and R$^7$ are halogen.

In certain embodiments, the pyrazoline dihydroquinolone derivative is a compound of the following formula:

Formula IG

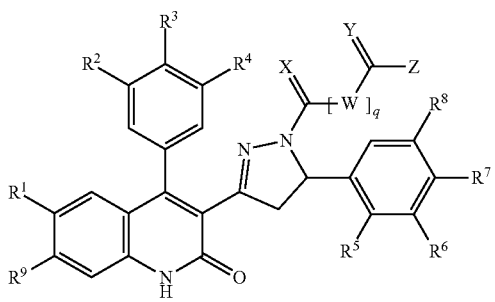

or salts, esters, or prodrugs thereof, wherein

W is at each occurrence CH$_2$, CH$_2$CH$_2$, CH, CH=CH, C=O, O, S, or NH;

q is 1, 2, or 3;

X or Y are each individually and independently O, S, NH, N-alkyl, or two hydrogens each of which are singly bonded to the adjacent C;

Z is halogen, OH, O-alkyl, O-alkanoyl, NH$_2$, NH-alkyl, NH-alkanoyl, SH, S-alkyl, or S-alkanoyl wherein Z is optionally substituted with one or more the same or different R$^{10}$;

R$^1$, R$^2$, R$^3$, R$^4$, R$^5$, R$^6$, R$^7$, R$^8$ and R$^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein R$^1$, R$^2$, R$^3$, R$^4$, R$^5$, R$^6$, R$^7$, R$^8$ and R$^9$ are optionally substituted with one or more, the same or different R$^{10}$;

R$^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein R$^{10}$ is optionally substituted with one or more, the same or different, R$^{11}$; and R$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, W is CH$_2$ and q is 2.

In certain embodiments, X is two hydrogens each of which are singly bonded to the adjacent C, Y is O, and Z is halogen, OH, O-alkyl, or O-alkanoyl.

In certain embodiments, X is O, Y is two hydrogens each of which are singly bonded to the adjacent C, Z is halogen, OH, O-alkyl, or alkanoyl.

In certain embodiments, R$^7$ is a halogen.

In certain embodiments, R$^3$ is a halogen.

In certain embodiments, R$^1$ is a halogen.

In certain embodiments, R$^1$ is hydrogen, R$^3$ and R$^7$ are halogen.

In certain embodiments, the compounds for formula II have formula IA or IB,

Formula IH

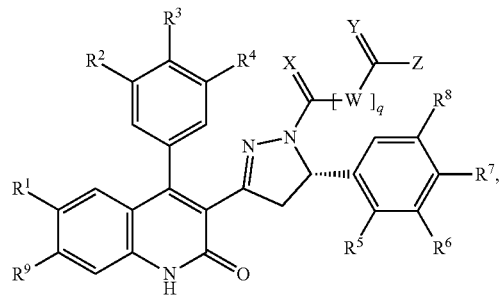

-continued

Formula IJ or salts, esters, or prodrugs thereof. In certain embodiments, compositions comprised the compounds of Formula IH or II in greater than 55%, 65%, 75%, 85%, or 95% enantiomeric excess or diastereomeric excess.

In certain embodiments, the pyrazoline dihydroquinolone derivative is a compound of the following formula:

Formula IJ or salts, esters, or prodrugs thereof, wherein
W is at each occurrence $CH_2$, $CH_2CH_2$, CH, CH=CH, C=O, O, S, or NH;
q is 1, 2, or 3;
X is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^2$, $R^3$, $R^4$, $R^5$, $R^6$, $R^7$, $R^8$ and $R^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^1$, $R^2$, $R^3$, $R^4$, $R^5$, $R^6$, $R^7$, $R^8$ and $R^9$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, W is $CH_2$ and q is 2.
In certain embodiments, X is two hydrogens each of which are singly bonded to the adjacent C and Z is halogen, OH, O-alkyl, or O-alkanoyl.
In certain embodiments, X is O and Z is halogen, OH, O-alkyl, or alkanoyl.
In certain embodiments, $R^7$ is a halogen.
In certain embodiments, $R^3$ is a halogen.
In certain embodiments, $R^1$ is a halogen.
In certain embodiments, $R^1$ is hydrogen, $R^3$ and $R^7$ are halogen.

In certain embodiments, the pyrazoline dihydroquinolone derivative is a compound of the following formula:

Formula IK or salts, esters, or prodrugs thereof, wherein
q is 1, 2, or 3;
X is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^2$, $R^3$, $R^4$, $R^5$, $R^6$, $R^7$, $R^8$ and $R^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^1$, $R^2$, $R^3$, $R^4$, $R^5$, $R^6$, $R^7$, $R^8$ and $R^9$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, q is 2.

In certain embodiments, X is two hydrogens each of which are singly bonded to the adjacent C and Z is halogen, OH, O-alkyl, or O-alkanoyl.

In certain embodiments, X is O and Z is halogen, OH, O-alkyl, or alkanoyl.

In certain embodiments, $R^7$ is a halogen.

In certain embodiments, $R^3$ is a halogen.

In certain embodiments, $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

Formula IL or salts, esters, or prodrugs thereof, wherein
X is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^2$, $R^3$, $R^4$, $R^5$, $R^6$, $R^7$, $R^8$ and $R^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^1$, $R^2$, $R^3$, $R^4$, $R^5$, $R^6$, $R^7$, $R^8$ and $R^9$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is two hydrogens each of which are singly bonded to the adjacent C and Z is halogen, OH, O-alkyl, or O-alkanoyl.

In certain embodiments, X is O and Z is halogen, OH, O-alkyl, or alkanoyl.

In certain embodiments, $R^7$ is a halogen.

In certain embodiments, $R^3$ is a halogen.

In certain embodiments, $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

Formula IM or salts, esters, or prodrugs thereof, wherein
q is 1, 2, or 3;
Y is O, S, NH, N-alkyl, or two hydrogens each of which are singly bonded to the adjacent C;
Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;
$R^1$, $R^2$, $R^3$, $R^4$, $R^5$, $R^6$, $R^7$, $R^8$ and $R^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^1$, $R^2$, $R^3$, $R^4$, $R^5$, $R^6$, $R^7$, $R^8$ and $R^9$ are optionally substituted with one or more, the same or different $R^{10}$;
$R^{10}$ is alkyl, halogen, nitro, cyano, hydroxy, amino, mercapto, formyl, carboxy, alkanoyl, carbamoyl, alkoxy, alkylthio, alkylamino, $(alkyl)_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, q is 2.

In certain embodiments, Y is O and Z is halogen, OH, O-alkyl, or O-alkanoyl.

In certain embodiments, Y is two hydrogens each of which are singly bonded to the adjacent C and Z is halogen, OH, O-alkyl, or alkanoyl.

In certain embodiments, $R^7$ is a halogen.

In certain embodiments, $R^3$ is a halogen.

In certain embodiments, $R^1$ is a halogen.

In certain embodiments, $R^1$ is hydrogen, $R^3$ and $R^7$ are halogen.

In certain embodiments, the pyrazoline dihydroquinolone derivative is a compound of the following formula:

Formula IN

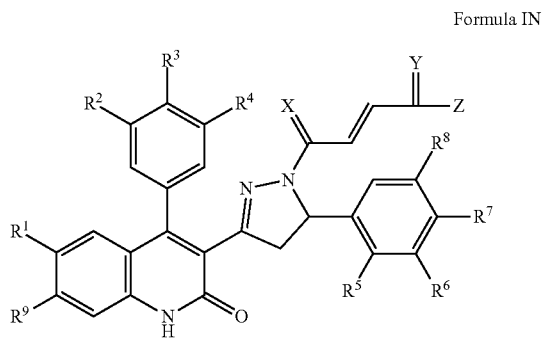

or salts, esters, or prodrugs thereof, wherein

X or Y are each individually and independently O, S, NH, N-alkyl, or two hydrogens each of which are singly bonded to the adjacent C;

Z is halogen, OH, O-alkyl, O-alkanoyl, $NH_2$, NH-alkyl, NH-alkanoyl, SH, S-alkyl, or S-alkanoyl wherein Z is optionally substituted with one or more the same or different $R^{10}$;

$R^1$, $R^2$, $R^3$, $R^4$, $R^5$, $R^6$, $R^7$, $R^8$ and $R^9$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^1$, $R^2$, $R^3$, $R^4$, $R^5$, $R^6$, $R^7$, $R^8$ and $R^9$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is two hydrogens each of which are singly bonded to the adjacent C, Y is O, and Z is halogen, OH, O-alkyl, or O-alkanoyl.

In certain embodiments, X is O, Y is two hydrogens each of which are singly bonded to the adjacent C, Z is halogen, OH, O-alkyl, or alkanoyl.

In certain embodiments, $R^7$ is a halogen.

In certain embodiments, $R^3$ is a halogen.

In certain embodiments, $R^1$ is a halogen.

In certain embodiments, $R^1$ is hydrogen, $R^3$ and $R^7$ are halogen.

In certain embodiments, with regard to any of the above-disclosed herein, $R^2$, $R^4$, $R^5$, $R^6$, $R^8$, and $R^9$ are hydrogen.

In certain embodiments, the pyrazoline dihydroquinolone derivative is a compound such as 4-(5-(4-chlorophenyl)-3-(4-(4-chlorophenyl)-2-oxo-1,2-dihydroquinolin-3-yl)-4,5-dihydro-1H-pyrazol-1-yl)-4-oxobutanoic acid optionally substituted with one or more the same or different substituents;

(S)-4-(5-(4-chlorophenyl)-3-(4-(4-chlorophenyl)-2-oxo-1,2-dihydroquinolin-3-yl)-4,5-dihydro-1H-pyrazol-1-yl)-4-oxobutanoic acid optionally substituted with one or more the same or different substituents;

4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoic acid optionally substituted with one or more the same or different substituents; and 4-(4-chlorophenyl)-3-(5-(4-chlorophenyl)-1-(4-hydroxybutanoyl)-4,5-dihydro-1H-pyrazol-3-yl)quinolin-2(1H)-one optionally substituted with one or more the same or different substituents; or any compound disclosed herein optionally substituted with one or more the same or different substituents or a derivative of any compound disclosed herein optionally substituted with one or more the same or different substituents.

Negative Allosteric Modulators of the NMDA Receptor

Described herein is the synthesis and structure-activity relationship for a class of pyrazoline containing dihydroquinolone negative allosteric modulators of the NMDA receptor that show strong subunit-selectivity for GluN2C- and GluN2D-containing receptors over GluN2A- and GluN2B-containing receptors. Several members of this class inhibit NMDA receptor responses in the nanomolar range, and are more than 50-fold selective over GluN1/GluN2A and GluN1/GluN2B NMDA receptors, as well as AMPA, kainate, GABA, glycine, nicotinic, serotonin, and purinergic receptors. Analysis of the purified enantiomers of one of the more potent and selective compounds show that the S enantiomer is more potent and more selective than the R enantiomer. For one of the tested compounds, the S enantiomer has an IC50 value of 0.17-0.22 μM at GluN2D- and GluN2C-containing receptors, respectively, and shows over 200-fold selectivity over other NMDA receptor subunits. The subunit-selectivity of this class of compounds should be useful in defining the role of GluN2C/GluN2D-containing receptors in specific brain circuits in both physiological and patho-physiological conditions.

Figure 4:
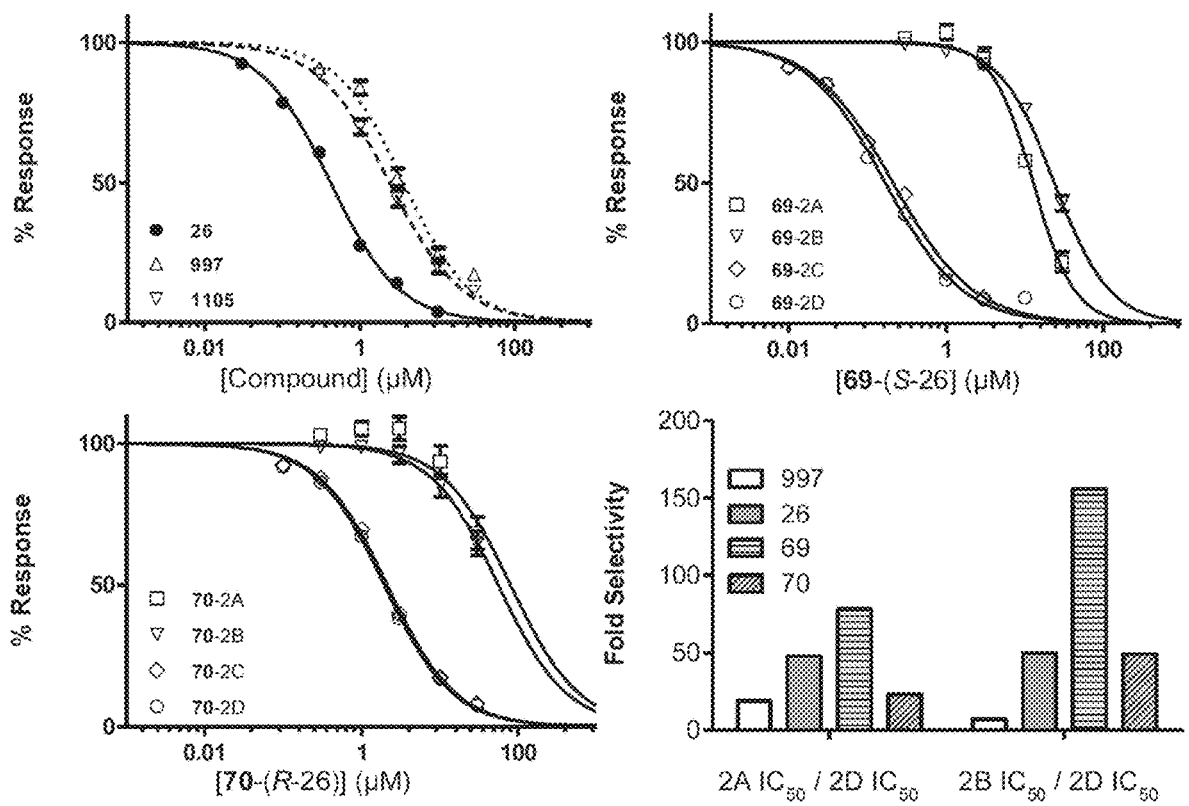
FIG. 4 shows data indicating improvements in selectivity and potency for certain embodiments. The potency of the racemic compounds at GluN2D-containing receptors was improved 10-fold over the previous members in the class. The potency of the S-enantiomer of compound (26)997-23 is two-fold more potent than the racemic mixture at GluN2D-containing receptors while the potency at GluN2A- and GluN2B containing receptors is unaffected. The potency of the R-enantiomer at GluN2C- and GluN2D-containing receptors is diminished as compared to the racemate making it less selective over GluN2A- and GluN2B-containing receptors. Bar graph showing the fold-selectivity improvements attained through SAR.

Described herein are potent, selective, and soluble negative allosteric modulators for GluN2C- and GluN2D-containing NMDA receptors that act on the membrane proximal lobe of the GluN2 glutamate binding domain. Several compounds have $IC_{50}$ values in the 100-500 nanomolar range that show 50-140 fold selectivity over GluN2A- and GluN2B-containing receptors (FIG. 4).

Figure 5:
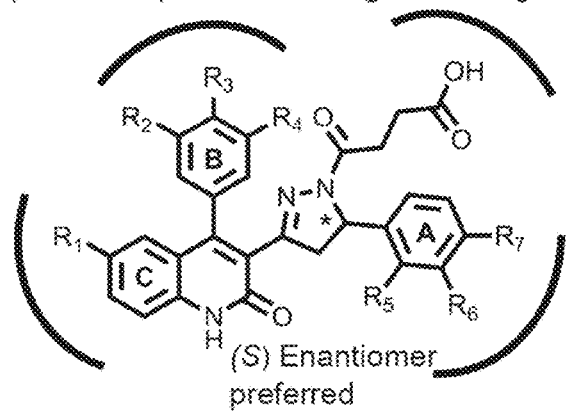
FIG. 5 illustrates a pharmacophore model describing findings from the SAR. The para-substitution of the A-ring shows correlation between the sigma coefficient and activity when $R_1$ is a chloro; The length and configuration of the acyl-chain is flexible, with the trans-configuration improving potency; B-ring modification shows an optimal para-sigma coefficient close to that of chloro and bromo substitutions for GluN2A-, GluN2C- and GluN2D-containing receptors, suggesting a conserved nature of the binding interaction at each of the three receptors and possibly a halogen bond. The C-ring substitutions explored are consistent with this portion of the molecule interacting with a hydrophobic pocket.

Experimental results indicated there is a conserved portion of the binding pocket between GluN2A-, GluN2C- and GluN2D-containing receptors with respect to the para-position of the B-ring, specifically with regard to the α coefficient (FIG. 2). The observation that there is desired activity with a chloro or bromo at this position has led to the hypothesis that there could be a halogen bond being formed with the receptors. Furthermore, the SAR has revealed that rigidifying the acyl-chain in the trans-conformation can enhance potency, while the length of the chain was found not to be crucial for activity (FIG. 5). Furthermore, the finding that 64 (997-57) (FIG. 16) retained both potency and selectivity suggests that the charge on the carboxylic acid is not crucial. The substituents that were explored on the A-ring allowed for an analysis that directly correlated potency to the α coefficients, when the R8 position was substituted with a chloro (FIG. 1). Thus, the electronics of the A-ring are an important factor for activity at the desired GluN2C- and GluN2D-containing receptors when the quinolone core is substituted with a chloro (FIGS. 1 and 5).

The GluN2C and GluN2D NMDA receptor subunits remain understudied, largely because of a lack of potent and selective pharmacological tools. However, these NMDA receptor subunits reside in a number of brain regions that are highly relevant for neurological disease. For example, expression of functional GluN2D in the subthalamic nuclei raises the possibility that GluN2D-selective inhibitors could attenuate neuronal firing rate and alter firing patterns in subthalamic neurons, which could be of utility in Parkinson's disease. See Monyer et al., Neuron, 1994, 12, 529-540; Monyer et al., Neuron, 1994, 12, 529-540; Standaert et al., Neuroscience Letters, 1993, 152, 161-164; Standaert et al., J Comp Neurol, 1994, 343, 1-16; Wilson & Bevan, Neuroscience, 2011, 198, 54-68; Wichmann & DeLong, Neurosurgery Clinics of North America, 1998, 9, 223; Bolam et al., Journal of Anatomy, 2000, 196, 527-542; Mullasseril et al., Nat Commun 2010, 1, 90. In addition, expression of GluN2D in substantia nigra pars compacta neurons raises the possibility that GluN2D-selective antagonists might serve neuro-protective roles in Parkinson's disease by diminishing $Ca^{2+}$ influx into the dopaminergic SNc neurons, which may lead to neuronal death. GluN2C is expressed widely in the cerebellum, and has also been suggested to have a role in both emotional learning and schizophrenia. See Dravid et al., Journal of Neuroscience, 2010, 30, 2741-2754 and Lisman et al., Trends in Neurosciences, 2008, 31, 234-242.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyoptehilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Methods of Treating CNS Diseases

In certain embodiments, the disclosure relates to the method of treating or preventing a disease or condition by administering to a person in need of such treatment an effective amount of a compound of formula I, wherein the disease or condition is cognitive impairment, a neurodegenerative disease, such as Parkinson's disease, pain, depression, schizophrenia, attention deficit hyperactivity disorder, or addiction.

In certain embodiments, the disclosure relates to the method of treating or preventing a disease or condition by administering to a person in need of such treatment an effective amount of a compound of formula I, wherein the disease or condition is neurodegenerative disease such as Alzheimer's, Parkinson's, dementia with Lewy bodies, or mild cognitive impairment.

In certain embodiments, the disclosure relates to the method of treating or preventing a disease or condition by administering to a person in need of such treatment an effective amount of a compound of formula I, wherein the disease or condition is stress, a thought disorder such as hallucinations, delusions, or atatonia or psychiatric disorders such as schizophrenia or a mood disorders such as depression, bipolar disorder, manic depression, post-traumatic stress disorder, obsessive-compulsive disorder, severe sleep deprivation.

In certain embodiments, the disclosure relates to the method of treating or preventing a disease or condition by administering to a person in need of such treatment an effective amount of a compound of formula I, wherein the disease or condition is stroke, traumatic brain injury, brain tumors, multiple sclerosis, or epilepsy.

In certain embodiments, the disclosure relates to the method of treating or preventing a disease or condition by administering to a person in need of such treatment an effective amount of a compound of formula I, wherein the disease or condition is a motor disorder, dysfunction, or sensory impairment, ataxia, dystonia, or dyskineisa. In certain embodiments, the motor dysfunction is developmental dyspraxia, cerebral palsy, muscular dystrophy, multiple sclerosis, or Parkinson's disease.

In certain embodiments, the disclosure relates to the method of treating or preventing a disease or condition by administering to a person in need of such treatment an effective amount of a compound of formula I, wherein the disease or condition is infectious and postinfectious syndromes, including infections causing delirium, viral encephalitis, HIV, malaria, Lyme disease, or syphilis.

In certain embodiments, the disclosure relates to the method of treating or preventing a disease or condition by administering to a person in need of such treatment an effective amount of a compound of formula I, wherein the disease or condition is endocrine disease, such as hypothyroidism, hyperthyroidism, adrenal failure, Cushing's syndrome, hypoparathyroidism and hyperparathyroidism.

In certain embodiments, the disclosure relates to the method of treating or preventing a disease or condition by administering to a person in need of such treatment an effective amount of a compound of formula I, wherein the disease or condition is an acquired metabolic disorders, including electrolyte disturbances such as hypocalcemia, hypernatremia, hyponatremia, hypokalemia, hypomagnesemia, hypermagnesemia, hypercalcemia, and hypophosphatemia, but also hypoglycemia, hypoxia, and failure of the liver or kidney.

In certain embodiments, the disclosure relates to the method of treating or preventing a disease or condition by administering to a person in need of such treatment an effective amount of a compound of formula I, wherein the disease or condition is autoimmune and related disorders, such as systemic lupus erythematosus (lupus, SLE), sarcoidosis, encephalopathy, and anti-NMDA-receptor encephalitis.

In certain embodiments, the disclosure relates to the method of treating or preventing a disease or condition by administering to a person in need of such treatment an effective amount of a compound of formula I, wherein the disease or condition is poisoning, by therapeutic drugs, recreational drugs, and a range of plants, fungi, metals, organic compounds, and a few animal toxins.

In certain embodiments, the disclosure relates to the method of treating or preventing a disease or condition by administering to a person in need of such treatment an effective amount of a compound of formula I, wherein the disease or condition is some sleep disorders, including hallucinations in narcolepsy (in which REM sleep intrudes into wakefulness).

In certain embodiments, the disclosure relates to a method of treatment, wherein a composition comprised of a compound of formulas I is administered in combination with a second active ingredient, selected from an antidepressant, antipsychotic, or anti-inflammatory agent.

In certain embodiments, the disclosure relates to a method of treatment, wherein a composition comprised of a compound of formulas I is administered in combination with a second active ingredient, selected from acamprosate, amlodipine, argatroban, baclofen, cilostazol, cinacalcet, clopidogrel, dyphylline, fenoldopam, leflunomide, mepacrine, methimazole, phenformin, prilocalne, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefinenoxime, aprindine, etomidate, mitiglinide, benidipine, levosimendan, zonisamide, imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, neurokinin receptor antagonists and triiodothyronine, or salts thereof.

Examples

Structure-Activity Relationship Studies

Figure 6:
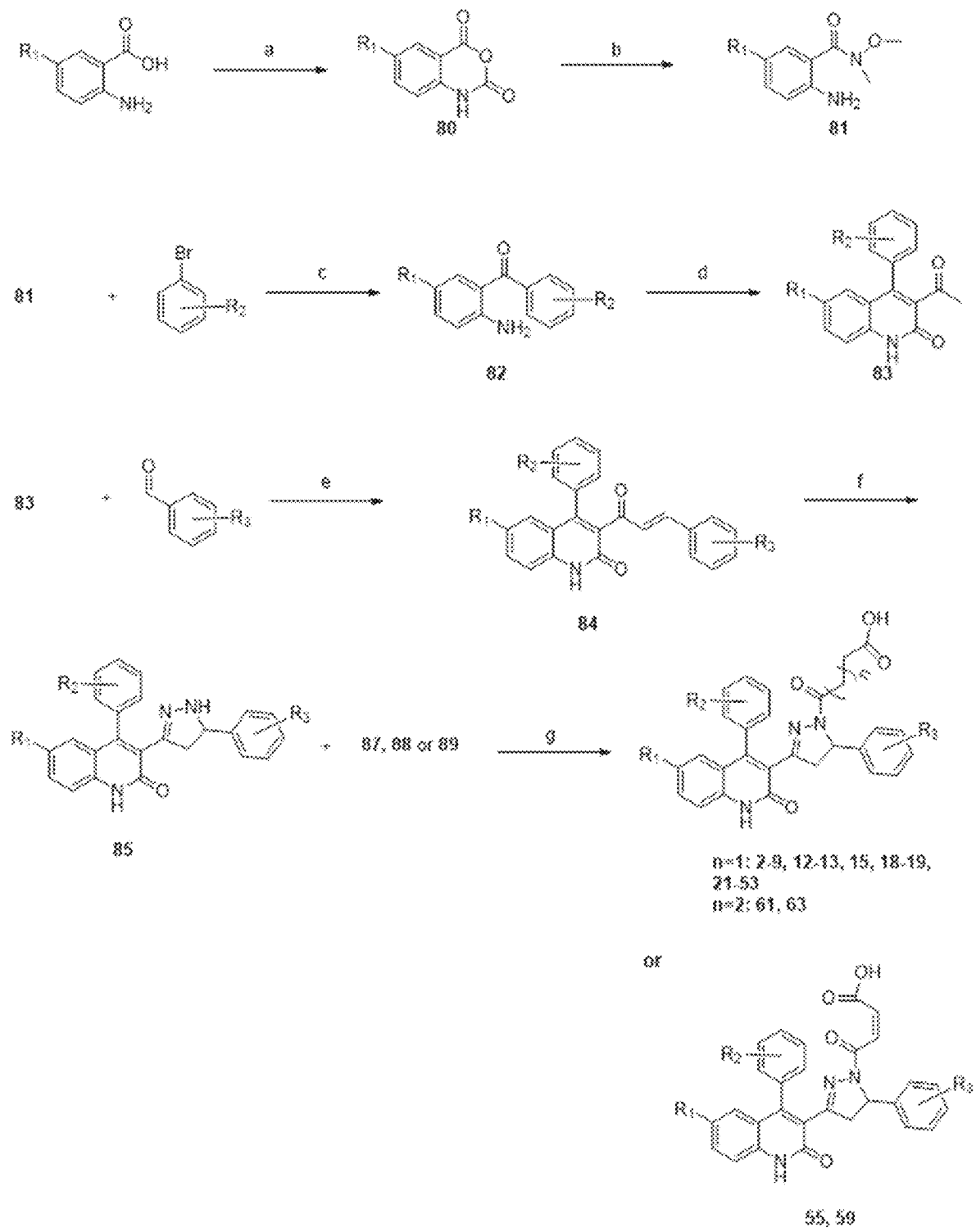
FIG. 6 shows a scheme illustrating the synthesis of certain dihydro-quinolone-pyrazoline derivatives. (a) Anhydrous THF, Triphosgene (warning, triphosgene is toxic, see methods), reflux. (b) EtOH, Weinreb's HCl salt, reflux. (c) Anhydrous THF, n-butyllithium, −78° C. (d) Ethylacetoacetate, DMF, 4 Å molecular sieves, 180° C., μW. (e) 4:3 EtOH:H$_2$O (0.05 M), 0° C. to r.t. (f) EtOH, 110° C., μW. (g) Anhydrous THF, 4 Å molecular sieves, 165° C., μW.

The structure-activity relationship around the quinolone-pyrazoline core was probed by testing the potency and selectivity of analogues with aromatic rings containing a variety of substitutions in combination with perturbations of the acyl chain moiety (FIG. 1a). A representative synthesis of these analogs is shown in FIG. 6. Briefly, anthranillic acids were allowed to react with triphosgene under standard conditions to yield the isatoic anhydride derivatives (80). These compounds were then converted to the appropriate benzophenones via a two-step sequence (82). See Frye et al., The Journal of Organic Chemistry, 1991, 56, 3750-3752.

The substituted quinolone core was accessed by condensation with ethyl acetoacetate using microwave irradiation (83). The resultant methyl ketone underwent base-catalyzed condensation with an appropriate aryl aldehyde yielding the α,β-unsaturated ketone compounds (84). These intermediates could be treated with hydrazine monohydrate in ethanol, utilizing microwave irradiation, to yield the pyrazoline containing compounds (85). The pyrazoline amine was then functionalized with succinic anhydride (87), glutaric anhydride (88), or maleic anhydride (89) to yield the fully saturated or cis-double bond acyl chain derivatives.

Figure 7:
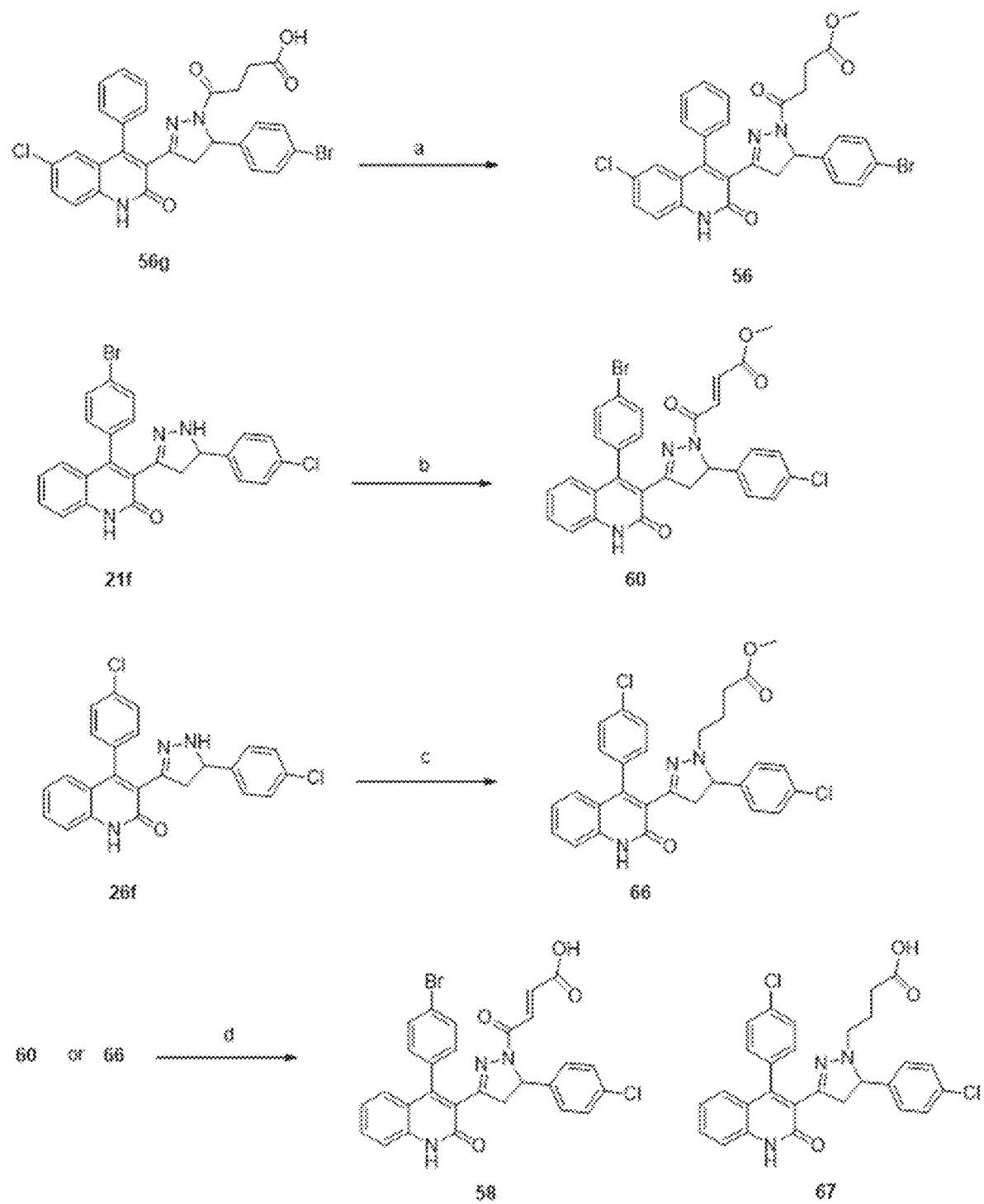
FIG. 7 shows a scheme illustrating modifications to the acyl-chain of certain embodiments. (h) SOCl$_2$, MeOH. (i) Anhydrous THF, (E)-methyl 4-chloro-4-oxobut-2-enoate, 4 Å molecular sieves, 165° C., μW. (j) NaOH, EtOH:H$_2$O. (k) Methyl 4-oxobutanoate, BH$_3$-DMS, THF.

A saturated mono-methyl ester analog (56) was prepared under standard esterification conditions (FIG. 7). The unsaturated fumaric derivatives could be accessed under standard amide coupling conditions using (E)-4-methoxy-4-oxobut-2-enoic acid, or with the acid chloride of the same compound, which could be saponified under basic conditions yielding the target scaffolds (58, FIG. 7). Additionally, the acyl chain was replaced with the alkyl chain using the pyrazoline derivative and methyl 4-oxobutanoate under reductive amination conditions to give compound 67.

Figure 1B:
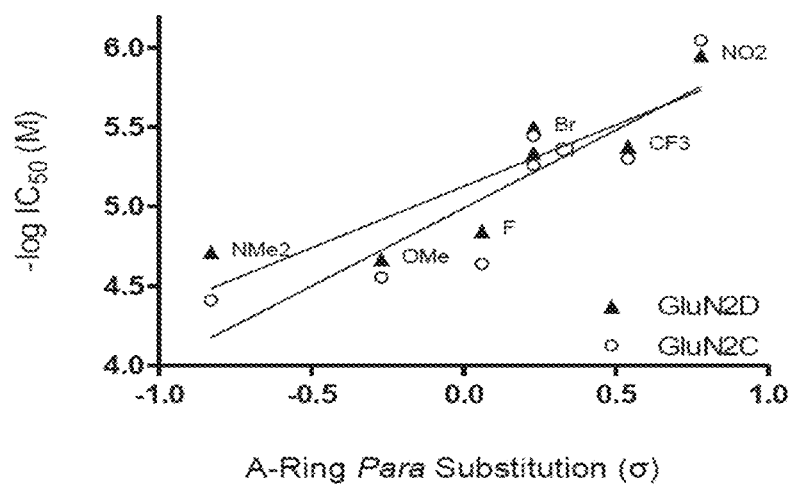
FIG. 1B. The σ contribution of the para-substitution vs. $-\log IC_{50}$ values of the A-ring shows a correlation for GluN2C- and GluN2D-containing receptors. (GluN2D $r^2=0.82$, $p<0.05$ Pearson two-tailed correlation analysis); GluN2C $r^2=0.84$, $p<0.05$ Pearson two-tailed correlation analysis).
Figure 1C:
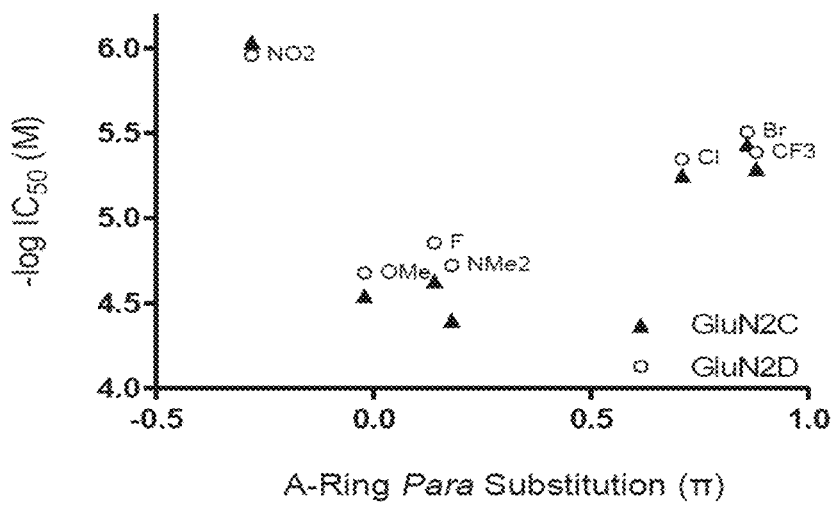
FIG. 1C. The π contribution of the para-substitution vs. $-\log IC_{50}$ values of the A-ring shows no correlation for GluN2C- and GluN2D-containing receptors (Pearson two-tailed correlation analysis $p>0.05$ for both).
Figure 10:
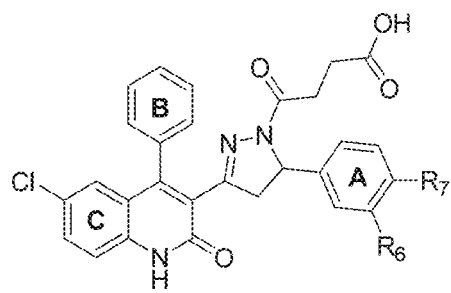
FIG. 10 shows a table containing data for evaluating activity of derivatives with certain A-ring para substitutions. IC$_{50}$ values were obtained by fitting the Hill equation to the average composite concentration-effect curves. Data are from 7-18 oocytes between 2-4 frogs; NE indicates less than 30% inhibition at 100 μM.
Figure 11:
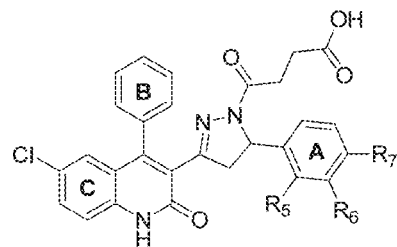
FIG. 11 shows a table containing data for evaluating activity of derivatives with certain A-ring ortho- and meta-substitutions. IC$_{50}$ values were obtained by fitting the Hill equation to the average composite concentration-effect curves. Data are from 6-10 oocytes between 2 frogs; NE indicates less than 30% inhibition at 100 μM.

The effect of substituents on the A-phenyl ring was evaluated (FIG. 1a) by holding the chloro substitution on the quinolone core constant and evaluating the substitutions shown is in FIGS. 10 and 11. Although substitution at any of the three available positions is tolerated, substitution at either the R5 or R6 position showed no improvement in potency or selectivity with any of the analogs tested (FIG. 11). Similarly, analogs with the C-ring replaced with furan, thiophene and pyridine substituents were evaluated and were inactive. However, 4-substituted phenyl derivatives result in improved potency and selectivity. This observation led to the identification of 5 (2023), with a para-nitro group at R7, which was a potent para-substituted analogue compared to the un-substituted compound 1 (1149) (1.1 µM vs. 88 µM, respectively, FIG. 10). Bio-isosteres of the nitro substitution were explored; replacing this group with a carboxylic acid (6)(997-5, FIG. 10) which showed no activity. By contrast, the methyl ester 7 (997-6) remained active but had decreased potency (32 µM vs 1.1 µM). Interestingly, sp3 hybridization is tolerated, but not preferred, as can be seen with the tri-fluoromethyl-containing compound 8 (997-8) (IC$_{50}$ 4.1 µM, GluN2D). A Hansch analysis of the para-σ and para-π parameters of the A-ring at GluN2D-containing receptors suggests that the σ contribution seems to be more directly associated with the IC$_{50}$ values (r2=0.82, p<0.05 Pearson two-tailed correlation analysis) than the relative hydrophobicity (r2=0.21, p>0.29, Pearson two-tailed correlation analysis) (FIG. 1b,c). See Topliss, Journal of Medicinal Chemistry. 1977, 20, 463-469.

Figure 12:
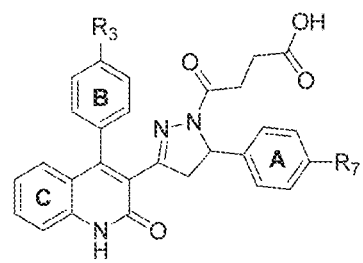
FIG. 12 shows a table containing data for evaluating activity of derivatives with certain A and B ring modifications. IC$_{50}$ values were obtained by fitting the Hill equation to the average composite concentration-effect curves. Data are from 8-18 oocytes between 2-3 frogs.

The B-ring substituents were modified with the aim of understanding the physical properties of the substituent effects at the meta- and para-positions. Para-B-ring substitutions showed enhanced potency at GluN2D- and GluN2C-containing receptors, with IC$_{50}$ values of 0.71 µM and 0.39 µM for (21) 997-7 inhibition of GluN2C- and GluN2D-containing receptors, respectively (FIG. 12). Interestingly, this compound also showed less selectivity for GluN2D-containing over GluN2A-containing receptors (33-fold) as compared to GluN2B-containing receptors (67-fold), suggesting perhaps a more favorable interaction with GluN2A-containing receptors.

Figure 2A:
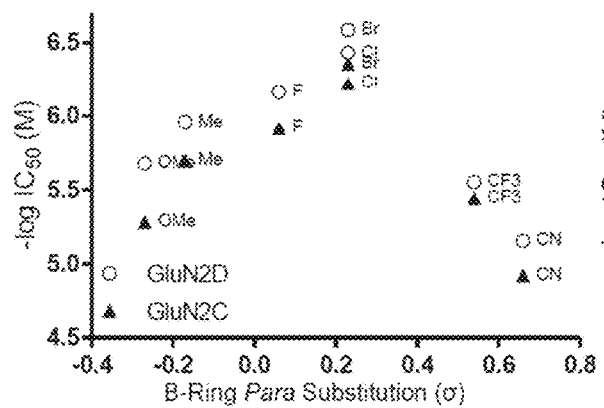
FIG. 2A shows data on the evaluation of substituent effects of B-ring modifications. The analysis of the para-substituents at GluN2C- and GluN2D-containing receptors appears parabolic with respect to the σ coefficient with an optimal value close to that of chloro and bromo substitutions.
Figure 2B:
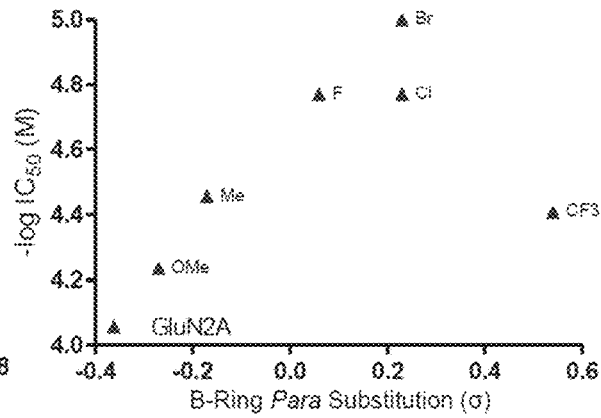
FIG. 2B. The analysis of the para-substituents at GluN2A-containing receptors shows a similar parabolic relationship as observed at the GluN2C- and GluN2D-containing receptors with the σ coefficient.
Figure 2C:
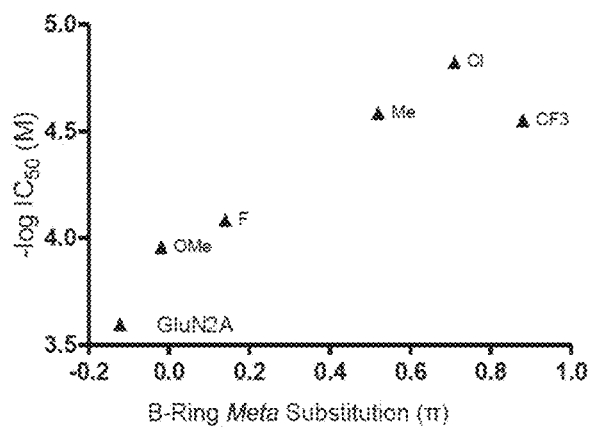
FIG. 2C. The analysis of the meta-substituent effects showed no clear correlation with the π coefficient for GluN2C- or GluN2D-containing receptors.
Figure 2D:
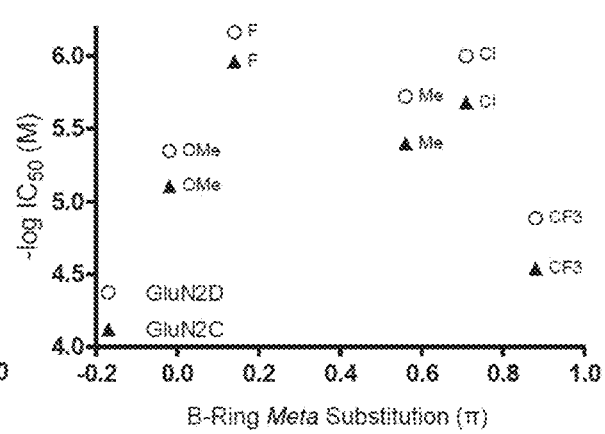
FIG. 2D. The analysis of the meta-substituent effects appears parabolic with respect to the π coefficient for GluN2A-containing receptors, suggesting an optimal interaction close to that of the chloro substitution.

Co-varying the A-ring para-substituents with the para-bromo B ring substitution allowed us to determine that the para-chloro A-ring substitution was optimal for potency (21, 22, 23, 24) (997-7, -20, -29, -55). A similar trend was observed using the para-chlorine substitution on the B-ring while co-varying the A-ring substituents (25, 26, 27, 28) (997-54, -23, -52, -53); therefore, this substitution was used for further SAR elaboration. The evaluation of the para-σ substituent effects at the B-ring show a seemingly parabolic relationship when compared to potency for GluN2A-, GluN2C- and GluN2D-containing receptors with an optimal σ value corresponding to the bromo and chloro substitutions at all three receptors (FIG. 2a, b). At the meta-position on the B ring, the correlation between the potency and the hydrophobic π value for substitutions at GluN2A-containing receptors also appears parabolic, but similar results were not found with GluN2B-, GluN2C-, or GluN2D-containing receptors (FIG. 2C, D). The decrease in potency at GluN2A-containing receptors in compounds that are meta-substituted with the CF3 group ((36) 997-51, FIG. 13 and FIG. 2D) could be a result of steric clashes with the receptor, or as was observed with the para-σ substituent, indicating that the optimal hydrophobicity at the GluN2A-containing receptors is attained with the chloro substitution.

Figure 14:
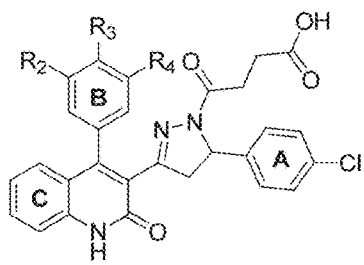
FIG. 14 shows a table containing data for evaluating activity of derivatives with certain B-ring di-substitutions. IC$_{50}$ values were obtained by fitting the Hill equation to the average composite concentration-effect curves. Data are from 8-15 oocytes between 2 frogs.

Whether combining a para-substitution for potency at GluN2D-containing receptors with a meta-substitution at GluN2A-containing receptors to improve selectivity was tested. Both Cl- and F-substitutions gave improved activity and selectivity, thus these groups were co-varied (FIG. 14). Compound 37 (997-38) was synthesized which maintained potency but did not increase selectivity (FIG. 14). Several other compounds that were di-substituted on the B-ring exhibited submicromolar potency at GluN2D-containing receptors (38, 39, 30, 41, 42) (997-34, 41, 42, 35, 37, FIG. 14).

Figure 15:
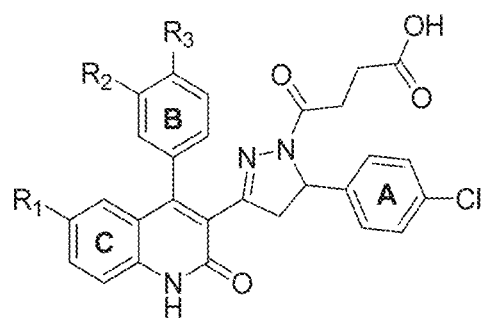
FIG. 15 shows a table containing data for evaluating activity of derivative with certain C-ring modification. IC$_{50}$ values were obtained by fitting the Hill equation to the average composite concentration-effect curves. Data are from 7-12 oocytes between 2 frogs.

A series of substitutions were made to the C-ring on the quinolone core (FIG. 15). Beginning with a methyl group at R1 in combination with either the para-chloro- or the meta-fluoro-substitution on the B-ring, compounds (43)997-43 and (44) 997-44 were synthesized, which decreased the potency as compared to the more favorable compounds with only B-ring and A-ring substitution. Interestingly, the modifications showed variability with regards to the relative selectivity for GluN2A- over GluN2B-containing receptors.

Figure 8:
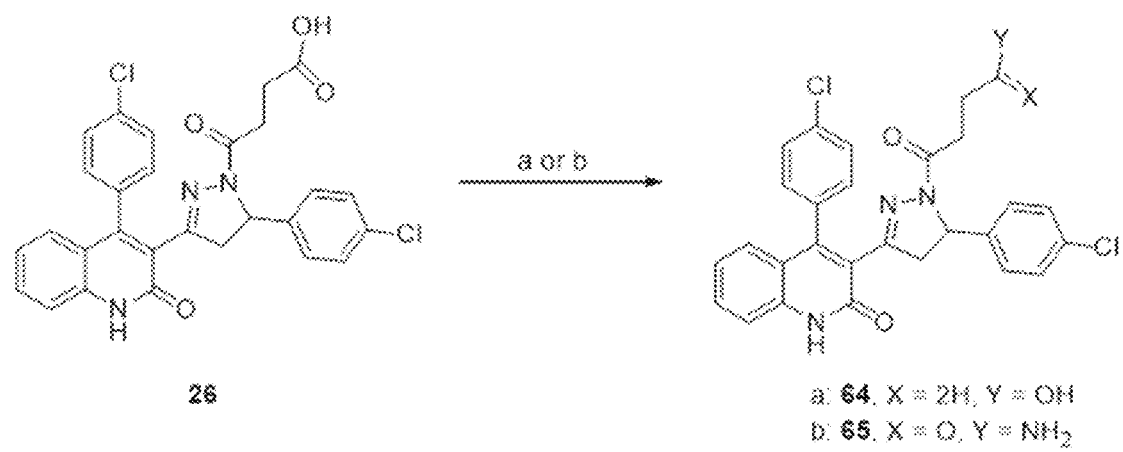
FIG. 8 shows a scheme illustrating the synthesis of certain primary alcohol and primary amide derivatives. (a) BH$_3$-DMS, anhydrous THF, 0° C. (b) EDCI, DMAP, NH$_3$ in dioxane (0.5M), THF.
Figure 9:
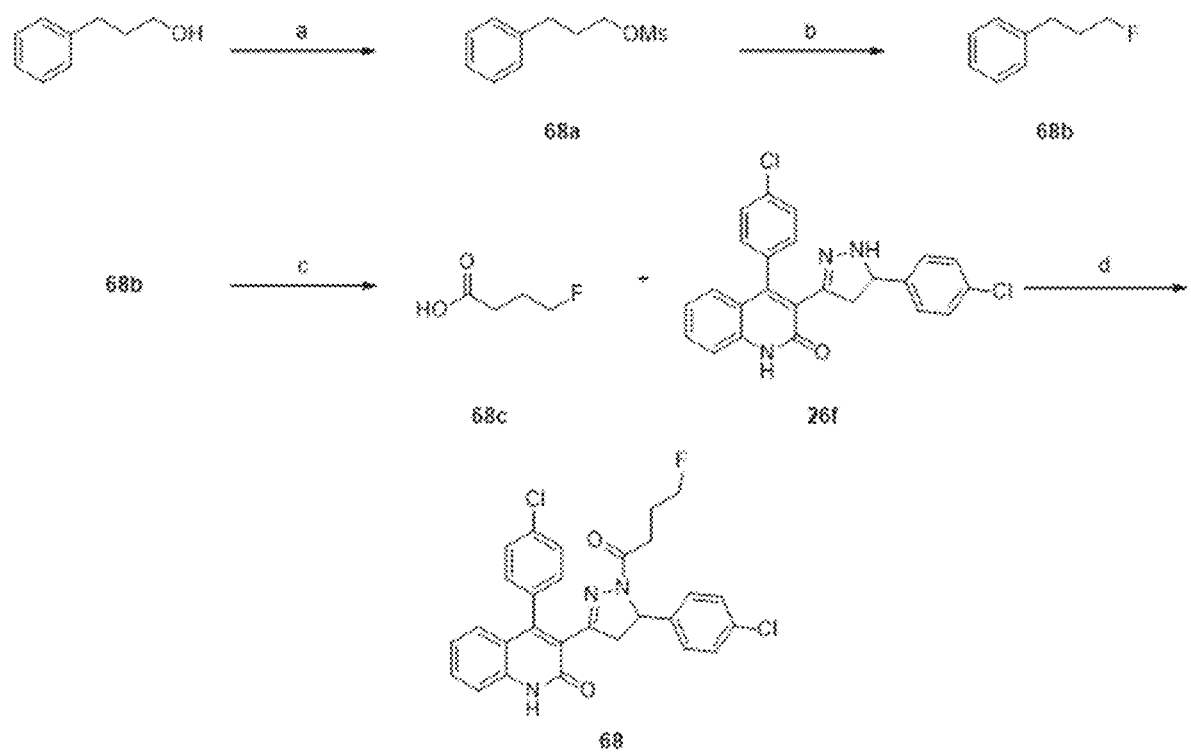
FIG. 9 shows a scheme illustrating synthesis of mono-fluoro acyl chain derivative. (a) MsCl, Et$_3$N, DCM. (b) CsF, t-BuOH. (c) RuCl$_3$, KNaIO$_4$, CCl$_4$:ACN:H$_2$O. (d) 68c, EDCI, DMAP, DCM.
Figure 13:
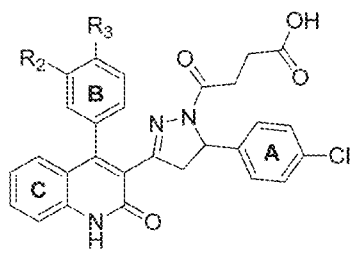
FIG. 13 shows a table containing data for evaluating activity of derivatives with certain B ring modifications. IC$_{50}$ values were obtained by fitting the Hill equation to the average composite concentration-effect curves. Data are from 6-14 oocytes between 2-3 frogs.
Figure 16A:
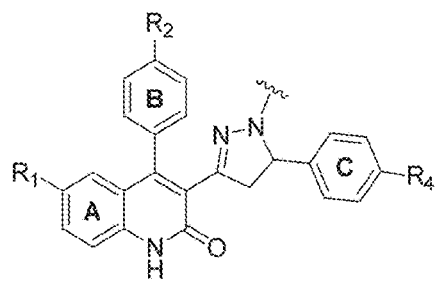
FIG. 16A shows a table containing data for evaluation activity of derivatives with certain acyl chain modifications. IC$_{50}$ values were obtained by fitting the Hill equation to the average composite concentration-effect curves. Data are from 5-24 oocytes between 2-4 frogs; NE indicates less than 30% inhibition at 100 μM.

A series of perturbations of the acyl chain of the pyrazoline nitrogen was evaluated (FIG. 16). Restricting the conformation to a cis-configuration with the maleate derivative maintained potency as compared with the parent compound in each instance tested. The trans-fumaric derivatives (58 and 54) (997-33 and 997-10) were more selective over GluN2A- and GluN2B-containing receptors, but no more potent at GluN2D-containing receptors than the saturated derivatives (FIGS. 16, 13, and 11). The fumaric ester was inactive, as was the succinic ester and (60 and 56) (997-31 and 997-11). Several glutaric derivatives were evaluated such as compound (61)997-32 (FIG. 16 and (22)997-20 in FIG. 12) at the receptors tested, suggesting that the length of the acyl chain is not crucial for activity. Reduction of the acid to the primary alcohol led to (64)997-57 (FIGS. 16 and 8) which retained activity at GluN2C- and GluN2D-containing receptors while improving selectivity over GluN2A-containing receptors to 90-fold as compared to the acid-containing compound ((26)997-23, FIG. 11). The primary amide derivative of the succinate acyl chain was then synthesized via a coupling reaction with NH3 (65) (997-58, FIG. 8), and found to retain activity but showed decreased potency and selectivity compared to the alcohol and acid moieties. Replacing the amide linkage with the alkyl derivative in compound (66) 997-62 slightly diminished potency at GluN2D-containing receptors over the parent compound (26)997-23, but maintained selectivity over the other receptor subtypes (FIGS. 18 and 8). Replacing the primary alcohol with the mono-fluoro isostere led to compound (68) 997-64 (FIGS. 16 and 9). These observations indicate that a hydrogen bond donor is important at the gamma position of the succinic acyl moiety.

Figure 3A:
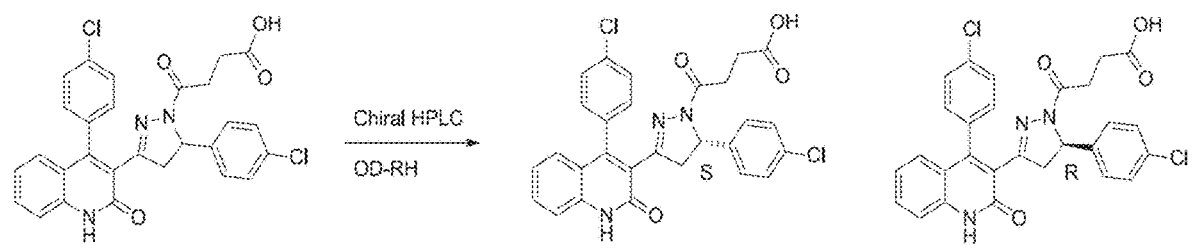
FIG. 3A illustrates a method for the separation of enantiomers. The enantiomers of the final compound (26)997-26, could be separated using reverse phase chiral chromatography (see Methods).
Figure 3B:
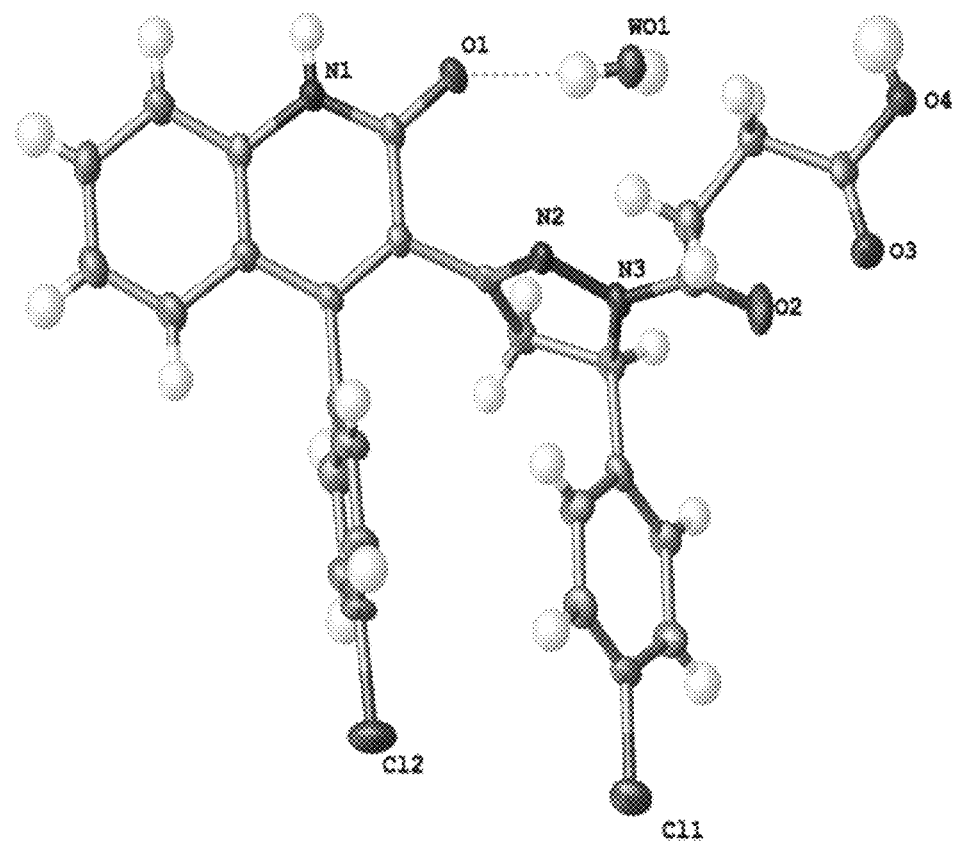
FIG. 3B. The crystal structure of the inactive enantiomer was solved using X-ray diffraction and has the R configuration.
Figure 17:
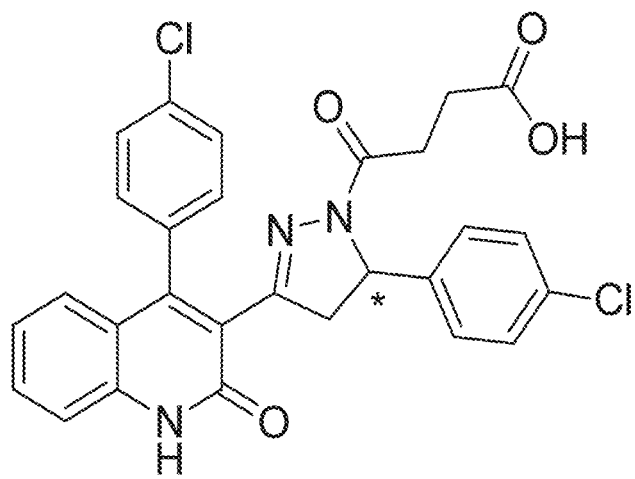
FIG. 17 shows a table containing data for evaluation activity of derivatives with certain racemic compositions. $IC_{50}$ values were obtained by fitting the Hill equation to the average composite concentration-effect curves. Data are from 8-17 oocytes between 2-4 frogs.

The selectivity and potency of purified enantiomers were evaluated. The enantiomers of the racemic final product (26) (997-23) were separable via reverse phase chiral chromatography using an OD-RH column (FIG. 3). Absolute stereochemistry of the second peak to elute was assigned using X-ray crystallography. Evaluation of the purified enantiomers showed that the S enantiomer (69) is 13 times more potent at GluN2D-containing receptors (IC$_{50}$ 0.17 μM) than the R enantiomer (70) (IC$_{50}$ 1.9 μM; FIGS. 17 and 4). In addition, the S enantiomer (69) shows enhanced selectivity for GluN2C- and GluN2D- over GluN2A- and GluN2B- containing receptors as compared to the racemic mixture (FIGS. 17 and 4).

Mechanism and Site of Action

Although it is not intended that embodiments of this disclosure be limited by any mechanism, Acker et al. report a mechanism for noncompetitive inhibition by GluN2C/D N-methyl-d-aspartate receptor subunit-selective modulators. Molecular Pharmacology 2011, 80, 782-795. Inhibition of GluN1/GluN2D responses by 1 μM (58) 997-33 was not surmounted by increasing both glutamate and glycine from 30 μM to 3 mM (4.1+0.58% of control in 30 μM, 3.1+0.50% of control in 3 mM; n=6, unpaired t-test). Moreover, inhibition produced by 1 μM (58) was not significantly different at −40 or +30 mV for (58) 997-33 (4.9+1.3% and 4.8+1.2% of control, respectively, n=8, Student's t-test, p=0.93).

Mutations to the wild type GluN2D receptor (Q801Y, L705F and A752V) were described to decrease sensitivity of the GluN2D receptor to blockade by either DQP-1105 and/or QNZ-46 in the membrane proximal region of the bilobed ligand binding domain encoded by the S2 region of the polypeptide chain were evaluated. See Acker et al. and Hansen & Traynelis, J Neurosci, 2011, 31, 3650-3661. A test of the effectiveness of racemic mixture of compound (26) 997-23 revealed that these mutants each significantly reduced the degree of inhibition, consistent with their acting at a similar site.

The actions of (58) 997-33 on GluN1/GluN2D receptors expressed in human embryonic kidney-293 (HEK293) cells were evaluated using patch clamp recordings. Evaluation of the concentration-effect relationship for inhibition of the response under whole-cell voltage clamp yielded an IC$_{50}$ value of 0.99 μM (n=4), consistent with that observed in oocytes. The time course of the onset of inhibition could be described by a single exponential function, and was concentration dependent. Evaluation of the reciprocal of the time constant as a function of concentration yields an association rate k$_{ON}$ of $1.23 \times 10^5$ M$^{-1}$ s$^{-1}$. The time course of recovery from inhibition could also be well described by a single exponential function, and the k$_{OFF}$ was determined by the y-intercept in the linear regression relationship between the reciprocal of the tau describing the onset of inhibition and the drug concentration. The dissociation rate was estimated from this value as 0.122 s$^{-1}$, and from this and k$_{ON}$, one can calculate the dissociation constant KD, which was 0.99 μM (FIG. 4). This value fits well with the IC$_{50}$ value determined from responses in oocytes.

Evaluation of Off-Target Effects

The off-target actions for the racemic compounds (26) 997-23 and (58) 997-33 were evaluated in a series of two-electrode voltage-clamp recordings using recombinant ligand-gated ion channels expressed in *Xenopus* oocytes (FIG. 18). Compounds (26)997-23 and (58) 997-33 were tested at 3 μM on GluA1-4, GluK1-2, GluK2/GluK5, 5HT3A, GABAA, GABAC, glycine α1, nicotinic acetylcholine receptors comprised of α1β1δγ, α3β4, α4β2, α7, or α9/α10, and purinergic P2X2 receptors. Of the ion channel classes evaluated, compounds (26)997-23 and (58) 997-33 altered agonist-induced currents by less than 10%, with the exception of the nicotinic acetylcholine receptors, which exhibited 13-28% inhibition by (26)997-23 and (58)997-33 (FIG. 18).

The actions of these two compounds at 5 μM on were tested 42 different ion channels, G-protein coupled receptors, and transporters via the National Institutes of Mental Health (NIMH) psychoactive drug screening program (PDSP). The primary binding assay demonstrated that compounds (26)997-23 and (58) 997-33 had a minimal effect on the receptors and transporters, with initial screens showing inhibition of 3 receptors by (26)997-23 (5HT6, H$_2$, kappa-opioid) and 4 receptors by (58) 997-33 (5-HT1E, 5-HT6, kappa-opioid, mu-opioid). The Ki values at these receptors were greater than 10 μM for both compounds on all receptors. The data collected from both the two-electrode voltage-clamp experiments and the PDSP demonstrate the utility of this class of compounds as selective inhibitors of the GluN2C- and GluN2D-containing NMDA receptors.

Plasma Stability, Aqueous Solubility, BBB Penetration and Human Liver Microsomal Stability Three analogs, (58) 997-33, (26)997-23 and (64) 997-57 were evaluated for plasma stability as well as aqueous solubility. The compounds showed minimal degradation in human, rat or mouse plasma over a two-hour time-course. The aqueous solubility of compounds (26)997-23 and (58) 997-33 was evaluated in oocyte recording buffer using nephelometry. Both compounds were assessed to be soluble at >80 μM. The topological polar surface area (TPSA) of the carboxylic acid compounds was calculated to be outside the optimal range (<90 Å$^2$) for blood-brain barrier penetration ((26)997-23 TPSA, 129.5 Å$^2$, QikProp). However, reduction of the acid to the alcohol moves the properties of this class closer to a typical range for CNS penetration ((64)997-57; 102.0 Å$^2$, QikProp). In order to assess the potential BBB penetration, compounds (26)997-23 and (64)997-57 were selected for evaluation in the MDR1-MDCK permeability assay (FIG. 19). The results for the alcohol containing compound indicated a low BBB potential, however, the permeability coefficient (Papp (A-B)) was much closer to the recommended $3.0 \times 10^{-6}$ cm/s ((64)997-57, (P$_{app}$ A-B; $2.46 \times 10^{-6}$ cm/s)) than that of the carboxylic acid containing compound ((26)997-23, ($P_{app}$ A-B; 0.47×10$^{-6}$ cm/s)). The same compounds were also evaluated for metabolic stability using human liver microsomes. While the carboxylic acid containing (26)997-23 showed minimal degradation over the 60 minute assay, the alcohol derivative 64 (997-57) had a half-life of 13 minutes (FIG. 20). In order to evaluate an analog with lower TPSA, the mono-fluoro (68)997-64 (TPSA 79.08 Å$^2$; QikProp) was assayed in the MDR1-MDCK assay and was classified as being highly brain penetrable ($P_{app}$ A-B; 3.88×10$^{-6}$ cm/s; $P_{app}$ B-A; 9.52×10$^{-6}$ cm/s; FIG. 19). Furthermore, the half-life of this compound was determined to be 35 minutes in the human liver microsomal assay (FIG. 20).

Two-Electrode Voltage-Clamp Electrophysiology

*Xenopus laevis* oocytes were isolated and maintained as described in Hansen & Traynelis, J Neurosci 2011, 31, 3650-3661. Oocytes were placed in a perfusion chamber with recording solution comprised of (in mM) 90 NaCl, 1 KCl, 0.5 BaCl$_2$, 0.005 EDTA and 10 HEPES, pH adjusted to 7.4 with NaOH at 23° C. The glass electrodes used had tip resistance of 0.5-2.0 MΩ and were filled with 0.3-3.0 M KCl. Compounds were made as 20 mM stock solutions in DMSO and diluted to final concentrations in recording solution (final DMSO was 0.1-0.05% vol/vol). The current recordings were performed using a Warner OC-725B or C amplifier at a holding potential of −40 mV.

Subunit selectivity was determined by recording from various ligand-gated ion channels expressed in *Xenopus laevis* oocytes. The glutamate receptors GluA1-4, GluK1, and GluK2 were activated by 100 µM glutamate. GluK1 and GluK2 expressing oocytes were incubated for 5 minutes in 1 mg/ml of concanavalin A prior to recording. The GluK2/K5 receptor was activated with 100 µM AMPA (2-amino-3-(3-hydroxy-5-methyl-isoxazol-4-yl)propanoic acid). The GABAA and GABAC receptors were activated by 20 µM and 2 µM GABA respectively. Acetylcholine was used activate the nicotinic acetylcholine α1β1δγ (1 µM), α3β4 (10 µM), α2β4 (10 µM), α7 (300 µM), α9α10 (10 µM) receptors. The glycine α1 and 5-HT3A currents were evoked by 50 µM glycine receptor and 3 µM serotonin, respectively. The purinergic receptors human and rat P2X2 were activated with 9 µM adenosine tri-phosphate.

MDR1-MDCK Permeability

Cell monolayers were grown to confluence on collagen-coated, microporous, polycarbonate membranes in 12-well Costar Transwell® plates. The permeability assay buffer was Hanks Balanced Salt Solution containing 10 mM HEPES and 15 mM glucose at pH 7.4. The buffer in the receiver chamber also contained 1% bovine serum albumin. The dosing solution concentration in the assay buffer was 5 µM for each compound tested. The cell monolayers were dosed on the apical side (A-to-B) or basolateral side (B-to-A) and incubated at 37° C. with 5% CO$_2$ in a humidified incubator. Samples were taken from the donor and receiver chambers at 120 minutes. Each determination was performed in duplicate. The co-dosed lucifer yellow flux was also measured for each monolayer to ensure no damage was inflicted to the cell monolayers during the flux period. All samples were assayed by LC-MS/MS using electrospray ionization. The apparent permeability (Papp) and percent recovery were calculated as follows.

$$P_{app} = (dC_r/dt) \times V_r/(A \times CA) \quad (1)$$

$$\text{Percent recovery} = 100 \times ((V_r \times C_r^{final}) + (V_d \times C_d^{final}) + (V_d \times C_d^{final}))/(V_d \times CN) \quad (2)$$

Where:
dC$_r$/dt is the slope of the cumulative concentration in the receiver compartment versus time in µM s$^{-1}$;
V$_r$ is the volume in the receiver compartment in cm$^3$;
V$_d$ is the volume in the donor compartment in cm3;
A is the area of the insert (1.13 cm$^2$ for 12-well Transwell®);
CA is the average of the nominal dosing concentration and the measured 120 minute donor concentration in µM;
CN is the nominal concentration of the dosing solution in µM;
C$_r^{final}$ is the cumulative receiver concentration in µM at the end of the incubation period;
C$_d^{final}$ is the concentration of the donor in µM at the end of the incubation period.

Human Liver Microsomal Stability

Human liver microsomes were obtained from XenoTech. The reaction mixture was prepared with 0.5 mg/mL human liver microsomes, 100 mM potassium phosphate (pH 7.4), 5 mM magnesium chloride, 1 µM test compound. The reaction mixture was incubated in a shaking water bath at 37° C. for 3 minutes prior to the addition of NADPH (1 mM). Testosterone was run simultaneously in a separate vessel as a control. 100 µl aliquots were taken at 0, 10, 20, 30 and 60 minutes for both test compound and testosterone. The aliquots were combined immediately with 400 µl of ice cold 50/50 ACN/dH$_2$O containing 0.1% formic acid and internal standard to terminate the reaction. The samples were then mixed and centrifuged to precipitate microsomal proteins. All samples were assayed by LC-MS/MS using electrospray ionization and multiple reaction monitoring and the peak area responses to internal standard of the compounds at each time point was compared to the peak area response at time 0 to determine the percent compound remaining. The human liver microsomal stability assays were performed by Absorption Systems.

Separation and X-Ray Crystallography of Enantiomers

Separation of the final compounds used for biological testing from the racemic 997-23 was obtained using a ChiralPak OD-RH 30 mm×250 mm, 5 µm column using the following conditions: Flow rate 10 ml/min, injection volume 4-6 ml (2 mg/ml), 60% ACN (0.1% Formic acid): 40% H$_2$O (0.1% Formic acid); (66) S-997-23, R$_t$, 21.8; (67) R-997-23 R$_t$, 25.1 minutes. The e.e. of the final products, (67) R-997-23 and (66) S-997-23 was determined using an Agilent 1200 HPLC pump on a ChiralPak OD-RH column (4.6 mm×150 mm, 5 µm) using the following conditions: Flow rate 1 ml/min, injection volume 10 µl, 60% ACN (0.1% Formic acid): 40% H$_2$O (0.1% Formic acid); S-66 (S-997-23, [α]D20 −34.0 (c=0.32 mg/ml, chloroform), R$_t$, 7.47 min, 100% e.e. R-67 (R-997-23) [α]D20+36.0 (c=0.245 mg/ml, MeOH), R$_t$, 8.79 min, 100% e.e. Optical rotation data was collected using a Perkin-Elmer 314 instrument. NMR spectrum was identical to that of racemic (26) 997-23 for each enantiomer.

Single crystals of peak two from the separation of racemic 26 (997-23) (retention time: 25.1 minutes) were grown by slow evaporation of a solution of the compound in a mixture of methanol and water. Crystal data: C$_{28}$H$_{23}$Cl$_2$N$_3$O$_5$, (M=552.39): 1.124×0.087×0.056, orthorhombic, space group P 2$_1$2$_1$2$_1$ (no.19), a=8.0529(5) Å, b=10.2097(5) Å, c=31.2978(13) Å, V=2573.2(2) Å$^3$, Z=4, µ(MoKα)=0.315 mm$^{-1}$, Dcalc=1.490 g/mm$^3$; Temperature 173 K. Intensity data were collected on a Bruker APEX II CCD diffractometer with monochromated MoKα radiation (λ=0.71073 Å) at 173 K, in the 2θ range 2.6-53.4°. The user interface Olex2 was used for the crystallographic calculations and crystal structure visualization. The structure was solved with Superflip by charge flipping and refined
by least squares minimization using Shelx. A total of 15745 reflections were measured (2.602≤2θ≤53.41) while 5408 unique data ($R_{int}$=0.124) were used in the refinements. The final $R_1$ was 0.0590 (I>2σ(I)) and the weighted R value $wR_2$ was 0.0874.

General Procedure (G) for the Synthesis of Acylated Quinolone-Pyrazoline Products In an appropriately sized microwaveable vessel, the pyrazol-3-yl-quinolin-2(1H)-one intermediate (1.00 equiv.) was dissolved in anhydrous THF (0.15 M) with 4 Å molecular sieves present. The appropriate anhydride (1.00 equiv.) was added. The solution was microwaved with stirring for 20 minutes at 165° C. The THF was removed under vacuum, the organics were dissolved in DCM, washed three times with acidified (pH 2, HCl) brine, dried over magnesium sulfate, filtered, concentrated under reduced pressure and subjected to flash column chromatography using 0-10% MeOH:DCM gradient unless otherwise noted.

4-(3-(6-Chloro-2-oxo-4-phenyl-1,2-dihydroquinolin-3-yl)-5-(2-chlorophenyl)-4,5-dihydro-1H-pyrazol-1-yl)-4-oxobutanoic acid (18) (997-14 g, GluN2D-75). Compound 18 (997-14) was prepared according to general procedure G using dihydrofuran-2,5-dione (0.046 g, 0.460 mmol) and 18f (0.200 g, 0.460 mmol). After removal of the THF, the title compound was obtained by precipitation from EtOAc using hexanes as a yellow solid. Yield 0.136 g, 55.3%. $^1$H NMR (400 MHz, DMSO-$d_6$) δ 12.40 (s, 1H), 12.13 (s, 1H), 7.63 (dd, J=8.6, 1.6 Hz, 1H), 7.56-7.49 (m, 2H), 7.45-7.41 (m, 4H), 7.26 (t, J=7.6 Hz, 1H), 7.19-7.15 (m, 2H), 6.93 (s, 1H), 6.41 (d, J=7.4 Hz, 1H), 3.87 (dd, J=18.4, 12.4 Hz, 1H), 2.75 (dd, J=18.2, 4.7 Hz, 1H), 2.60-2.54 (m, 1H), 2.46-2.32 (m, 2H), 2.39-2.30 (m, 2H).

4-(5-(2-Bromophenyl)-3-(6-chloro-2-oxo-4-phenyl-1,2-dihydroquinolin-3-yl)-4,5-dihydro-1H-pyrazol-1-yl)-4-oxobutanoic acid (19) (997-15 g, GluN2D-079). Compound 19 (997-15) was prepared according to general procedure G using dihydrofuran-2,5-dione (0.063 g, 0.627 mmol) and 19f (0.300 g, 0.627 mmol). After removal of the THF, the title compound was obtained by precipitation from EtOAc and hexanes as a yellow solid. Yield 0.140 g, 38.6%. $^1$H NMR (400 MHz, DMSO-$d_6$) δ 12.41 (s, 1H), 12.05 (s, 1H), 7.64 (dd, J=8.9, 2.5 Hz, 1H), 7.59 (d, J=7.5 Hz, 1H), 7.53 (p, J=7.6 Hz, 2H), 7.42 (dd, J=11.1, 7.9 Hz, 3H), 7.26-7.15 (m, 3H), 6.93 (d, J=2.3 Hz, 1H), 6.39-6.32 (m, 1H), 5.48 (dd, J=12.1, 4.6 Hz, 1H), 3.87 (dd, J=18.3, 12.0 Hz, 1H), 2.73 (dd, J=18.4, 4.6 Hz, 1H), 2.62-2.51 (m, 1H), 2.49-2.28 (m, 3H).

4-(3-(6-Chloro-2-oxo-4-phenyl-1,2-dihydroquinolin-3-yl)-5-(3-fluorophenyl)-4,5-dihydro-1H-pyrazol-1-yl)-4-oxobutanoic acid (12)(997-16, GluN2D-080). Compound 12 (997-16) was prepared according to general procedure G using dihydrofuran-2,5-dione (0.120 g, 1.20 mmol) and 12f (0.500 g, 0.1.20 mmol). After removal of the THF, the title compound was obtained by precipitation from EtOAc and hexanes as a yellow solid. Yield 0.380 g, 62%. $^1$H NMR (400 MHz, DMSO-$d_6$) δ 12.42 (s, 1H), 12.15 (s, 1H), 7.65 (dd, J=8.7, 2.6 Hz, 1H), 7.53 (dt, J=16.1, 7.3 Hz, 2H), 7.44 (dt, J=13.0, 6.4 Hz, 3H), 7.26 (d, J=7.0 Hz, 2H), 7.03 (t, J=8.7 Hz, 1H), 6.93 (d, J=2.3 Hz, 1H), 6.64 (dd, J=12.3, 8.8 Hz, 2H), 5.35 (dd, J=12.3, 4.4 Hz, 1H), 3.75 (dd, J=18.6, 12.1 Hz, 1H), 2.81 (dd, J=17.7, 4.7 Hz, 1H), 2.60-2.23 (m, 4H).

4-(3-(6-Chloro-2-oxo-4-phenyl-1,2-dihydroquinolin-3-yl)-5-(3-chlorophenyl)-4,5-dihydro-1H-pyrazol-1-yl)-4-oxobutanoic acid ((13) 997-13, GluN2D-072). Compound 13 (997-13) was prepared according to general procedure G using dihydrofuran-2,5-dione (0.046 g, 0.460 mmol) and 13f (0.200 g, 0.460 mmol). After removal of the THF, the title compound was obtained by precipitating from EtOAc using hexanes as a yellow solid. Yield 0.156 g, 63.4%. $^1$H NMR (400 MHz, DMSO-$d_6$) δ 12.39 (s, 1H), 12.04 (s, 1H), 7.64-7.57 (m, 1H), 7.56-7.34 (m, 5H), 7.27-7.17 (m, 3H), 6.97-6.87 (m, 2H), 6.68 (d, J=6.8 Hz, 1H), 5.29 (dd, J=12.2, 4.8 Hz, 1H), 3.71 (dd, J=18.5, 12.0 Hz, 1H), 2.84-2.73 (m, 1H), 2.50-2.32 (m, 2H), 2.25 (t, J=6.7 Hz, 2H).

4-(3-(6-Chloro-2-oxo-4-phenyl-1,2-dihydroquinolin-3-yl)-5-(4-fluorophenyl)-4,5-dihydro-1H-pyrazol-1-yl)-4-oxobutanoic acid (2) (997-19, GluN2D-094). Compound 2 (997-19) was prepared according to general procedure G using dihydrofuran-2,5-dione (0.062 g, 0.622 mmol) and 2f (0.260 g, 0.622 mmol). After removal of the THF, the residue was dissolved in hot EtOAc and small portions of hexanes were added until a solid began to form. The solid was filtered and column chromatographed using 0-10% MeOH:DCM and the title compound was obtained as a yellow solid. Yield 0.236 g, 73.2%. $^1$H NMR (400 MHz, DMSO-$d_6$) δ 12.42 (s, 1H), 12.15 (s, 1H), 7.68-7.38 (m, 6H), 7.27 (d, J=7.4 Hz, 1H), 7.04 (td, J=8.8, 2.4 Hz, 2H), 6.93 (d, J=2.5 Hz, 1H), 6.85-6.76 (m, 2H), 5.35-5.30 (m, 1H), 3.80-3.67 (m, 1H), 2.83-2.74 (m, 1H), 2.48-2.39 (m, 2H), 2.34-2.25 (m, 2H).

4-(3-(6-Chloro-2-oxo-4-phenyl-1,2-dihydroquinolin-3-yl)-5-(3-methoxyphenyl)-4,5-dihydro-1H-pyrazol-1-yl)-4-oxobutanoic acid (15) (997-56, GluN2D-372). Compound 15 (997-56) was prepared according to general procedure G using dihydrofuran-2,5-dione (0.029 g, 0.29 mmol) and (15f) 6-chloro-3-(5-(3-methoxyphenyl)-4,5-dihydro-1H-pyrazol-3-yl)-4-phenylquinolin-2(1H)-one (0.13 g, 0.29 mmol). The title compound was purified using flash chromatography (2-10% MeOH:DCM) and isolated as a yellow solid. Yield 0.090 g, 59%. $^1$H NMR (400 MHz, DMSO-$d_6$) δ 12.41 (s, 1H), 12.08 (s, 1H), 7.64 (dt, J=8.8, 2.1 Hz, 1H), 7.58-7.42 (m, 3H), 7.39 (d, J=7.3 Hz, 1H), 7.27 (d, J=7.3 Hz, 1H), 7.13 (t, J=7.9 Hz, 1H), 6.93 (d, J=2.2 Hz, 1H), 6.77 (dd, J=8.2, 2.4 Hz, 1H), 6.59 (s, 1H), 6.32 (d, J=7.7 Hz, 1H), 5.27 (dd, J=12.0, 4.7 Hz, 1H), 3.77-3.63 (m, 5H), 2.85 (dd, J=18.4, 4.7 Hz, 1H), 2.48-2.36 (m, 2H), 2.28 (t, J=6.8 Hz, 2H).

4-(3-(6-Chloro-2-oxo-4-phenyl-1,2-di hydroquinolin-3-yl)-5-(4-chlorophenyl)-4,5-dihydro-1H-pyrazol-1-yl)-4-oxobutanoic acid (3) (997-12, GluN2D-070). Compound 3 (997-12) was prepared according to general procedure G using dihydrofuran-2,5-dione (0.046 g, 0.460 mmol) and 3f 6-chloro-3-(5-(4-chlorophenyl)-4,5-dihydro-1H-pyrazol-3-yl)-4-phenyl quinolin-2(1H)-one (0.200 g, 0.460 mmol). The title compound was obtained by removing the THF, dissolving the crude mixture into hot EtOAc and adding small portions of hot hexanes until a yellow precipitate formed. The mixture was allowed to cool and filtered to give the title compound as a yellow solid. Yield 0.187 g, 76.0%. $^1$H NMR (400 MHz DMSO-$d_6$) δ 12.42 (s, 1H), 12.15 (s, 1H), 7.64 (dd, J=8.7, 2.5 Hz, 1H), 7.61-7.38 (m, 5H), 7.27 (d, J=7.9 Hz, 3H), 6.94 (d, J=2.5 Hz, 1H), 6.79 (d, J=8.2 Hz, 2H), 5.33 (dd, J=12.1, 4.7 Hz, 1H), 3.75 (dd, J=18.5, 12.0 Hz, 1H), 2.78 (dd, J=18.4, 4.7 Hz, 1H), 2.49-2.23 (m, 4H).

4-(1-(3-Carboxypropanoyl)-3-(6-chloro-2-oxo-4-phenyl-1,2-dihydroquinolin-3-yl)-4,5-dihydro-1H-pyrazol-5-yl) benzoic acid (6) (997-5, GluN2D-038). Compound 6 (997-5) was prepared according to general procedure G using dihydrofuran-2,5-dione (0.045 g, 0.451 mmol) and 6f (0.200 g, 0.451 mmol). The solvent was removed and the product was obtained by dissolving in hot EtOAc and adding hexanes until a solid began to precipitate. The solution was cooled and the product filtered to yield a white solid. Yield 0.040 g, 16.3%. $^1$H NMR (400 MHz, DMSO-$d_6$) δ 12.42 (bs, 3H), 7.79 (d, J=8.0 Hz, 2H), 7.64 (dd, J=8.7, 2.4 Hz, 1H), 7.60-7.41 (m, 5H), 7.27 (d, J=7.4 Hz, 1H), 6.96-6.82 (m, 3H), 5.39 (dd, J=12.0, 4.8 Hz, 1H), 3.79 (dd, J=18.4, 12.2 Hz, 1H), 2.79 (dd, J=18.4, 4.7 Hz, 1H), 2.61-2.37 (m, 2H), 2.30 (t, J=6.9 Hz, 2H).

4-(3-(6-Chloro-2-oxo-4-phenyl-1,2-dihydroquinolin-3-yl)-5-(4-(methoxycarbonyl)phenyl)-4,5-dihydro-1H-pyrazol-1-yl)-4-oxobutanoic acid (7) (997-6, GluN2D-044). Compound 7 (997-6) was prepared according to general procedure G using dihydrofuran-2,5-dione (0.055 g, 0.546 mmol) and 7f (0.250 g, 0.546 mmol). The title compound was purified using flash chromatography (2-10% MeOH:DCM), followed by precipitation from hot EtOAc using hot hexanes. Yield 0.040 g, 13.13%. $^1$H NMR (400 MHz, DMSO-$d_6$) δ 12.38 (s, 1H), 12.06 (s, 1H), 7.84-7.72 (m, 2H), 7.64-7.35 (m, 6H), 7.22 (d, J=7.4 Hz, 1H), 6.87 (d, J=8.4 Hz, 3H), 5.36 (dd, J=12.3, 4.6 Hz, 1H), 3.90-3.69 (m, 4H), 2.74 (dd, J=18.5, 4.6 Hz, 1H), 2.51-2.33 (m, 2H), 2.30-2.21 (m, 2H).

4-(3-(6-Chloro-2-oxo-4-phenyl-1,2-dihydroquinolin-3-yl)-5-(4-(trifluoromethyl)phenyl)-4,5-dihydro-1H-pyrazol-1-yl)-4-oxobutanoic acid (8) (997-8, GluN2D-351, NR2D-167). Compound 8 (997-8) was prepared according to general procedure G using dihydrofuran-2,5-dione (0.043 g, 0.427 mmol) and 8f (0.200 g, 0.427 mmol). The title compound was obtained after flash chromatography (2-10% MeOH:DCM) followed by precipitation from EtOAc as a yellow solid. Yield 0.030 g, 12.4%. $^1$H NMR (400 MHz, DMSO-$d_6$) δ 12.42 (s, 1H), 12.04 (s, 1H), 7.65 (dd, J=8.7, 2.4 Hz, 1H), 7.61-7.40 (m, 7H), 7.26 (d, J=7.4 Hz, 1H), 6.99 (d, J=8.0 Hz, 2H), 6.93 (d, J=2.3 Hz, 1H), 5.43 (dd, J=12.2, 4.7 Hz, 1H), 3.79 (dd, J=18.5, 12.2 Hz, 1H), 2.80 (dd, J=18.6, 4.7 Hz, 1H), 2.60-2.40 (m, 2H), 2.29 (t, J=6.8 Hz, 2H).

4-(3-(6-Chloro-2-oxo-4-phenyl-1,2-dihydroquinolin-3-yl)-5-(4-methoxyphenyl)-4,5-dihydro-1H-pyrazol-1-yl)-4-oxobutanoic acid (9) (997-17, GluN2D-084). Compound 9 (997-17) was prepared according to general procedure G using dihydrofuran-2,5-dione (0.058 g, 0.582 mmol) and 9f (0.250 g, 0.582 mmol). After removal of the THF, the title compound was obtained by dissolving the crude mixture into hot EtOAc and adding small portions of hot hexanes until a yellow precipitate formed, the mixture was allowed to cool and filtered to give the title compound as a yellow solid. Yield 0.132 g, 42.8%. $^1$H NMR (400 MHz, DMSO-$d_6$) δ 12.40 (s, 1H), 12.16 (s, 1H), 7.64 (dd, J=8.9, 2.4 Hz, 1H), 7.60-7.49 (m, 3H), 7.45 (d, J=8.7 Hz, 1H), 7.43-7.38 (m, 1H), 7.29 (d, J=7.0 Hz, 1H), 6.93 (d, J=2.5 Hz, 1H), 6.82-6.66 (m, 4H), 5.24 (dd, J=12.1, 4.6 Hz, 1H), 3.89-3.62 (m, 4H), 2.78 (dd, J=18.3, 4.6 Hz, 1H), 2.45 (t, J=7.0 Hz, 2H), 2.27 (t, J=6.9 Hz, 2H).

4-(5-(4-Bromophenyl)-3-(4-(4-bromophenyl)-2-oxo-1,2-dihydroquinolin-3-yl)-4,5-dihydro-1H-pyrazol-1-yl)-4-oxobutanoic acid (21) (997-7, GluN2D-048). Compound 21 (997-7) was prepared according to general procedure G using dihydrofuran-2,5-dione (0.057 g, 0.573 mmol) and 21f (0.300 g, 0.573 mmol). There was a yellow solid present in the reaction vessel which was filtered and determined to be the title compound. Yield 0.320 g, 90%. $^1$H NMR (400 MHz, DMSO-$d_6$) δ 12.30 (s, 1H), 12.18 (s, 1H), 7.75 (d, J=8.2 Hz, 1H), 7.66 (d, J=8.2 Hz, 1H), 7.58 (t, J=7.8 Hz, 1H), 7.48-7.39 (m, 3H), 7.36 (d, J=8.1 Hz, 1H), 7.22 (d, J=8.1 Hz, 1H), 7.15 (t, J=7.7 Hz, 1H), 7.03 (d, J=8.2 Hz, 2H), 6.74 (d, J=7.9 Hz, 2H), 5.33 (dd, J=11.8, 4.4 Hz, 1H), 3.74 (dd, J=18.7, 12.1 Hz, 1H), 2.76 (dd, J=18.5, 4.4 Hz, 1H), 2.65-2.39 (m, 2H), 2.39-2.30 (m, 2H).

4-(3-(4-(4-Bromophenyl)-2-oxo-1,2-dihydroquinolin-3-yl)-5-(4-chlorophenyl)-4,5-dihydro-1H-pyrazol-1-yl)-4-oxobutanoic acid (22) (997-20, GluN2D-113). Compound 22 (997-20) was prepared according to general procedure G using dihydrofuran-2,5-dione (0.105 g, 1.04 mmol) and 22f (0.500 g, 1.044 mmol). After removal of the THF, the residue was partitioned between EtOAc and acidified brine. The organics were washed three times, dried over magnesium sulfate and concentrated under vacuum. The title compound was obtained after column chromatography using 10% MeOH:DCM. Yield 0.240 g, 39.7%. $^1$H NMR (400 MHz, DMSO-$d_6$) δ 12.29 (s, 1H), 12.05 (s, 1H), 7.74 (dd, J=8.1, 2.2 Hz, 1H), 7.65 (dd, J=8.1, 2.2 Hz, 1H), 7.58 (t, J=7.6 Hz, 1H), 7.42 (d, J=8.3 Hz, 1H), 7.36 (dd, J=8.1, 2.3 Hz, 1H), 7.34-7.25 (m, 2H), 7.22 (dd, J=8.2, 2.3 Hz, 1H), 7.15 (t, J=7.6 Hz, 1H), 7.03 (d, J=8.1 Hz, 1H), 6.85-6.75 (m, 2H), 5.35 (dd, J=11.9, 4.4 Hz, 1H), 3.73 (dd, J=18.4, 12.1 Hz, 1H), 2.76 (dd, J=18.6, 4.4 Hz, 1H), 2.65-2.42 (m, 2H), 2.34 (t, J=6.7 Hz, 2H).

4-(3-(4-(4-Bromophenyl)-2-oxo-1,2-dihydroquinolin-3-yl)-5-(4-fluorophenyl)-4,5-dihydro-1H-pyrazol-1-yl)-4-oxobutanoic acid (23) (997-29, GluN2D-161). Compound 23 (997-29) was prepared according to general procedure G using dihydrofuran-2,5-dione (0.054 g, 0.541 mmol) and 23f (0.250 g, 0.541 mmol). The title compound, a yellow solid, was obtained after purifying using flash chromatography (0-10% MeOH:DCM). Yield 0.100 g, 32.9%. $^1$H NMR (400 MHz, DMSO-$d_6$) δ 12.29 (s, 1H), 12.11 (s, 1H), 7.74 (d, J=8.0 Hz, 1H), 7.66 (d, J=8.2 Hz, 1H), 7.58 (t, J=7.7 Hz, 1H), 7.43 (d, J=8.3 Hz, 1H), 7.36 (d, J=8.0 Hz, 1H), 7.23 (d, J=8.2 Hz, 1H), 7.15 (t, J=7.6 Hz, 1H), 7.05 (t, J=8.9 Hz, 3H), 6.83 (dd, J=8.4, 5.2 Hz, 2H), 5.35 (dd, J=12.0, 4.4 Hz, 1H), 3.72 (dd, J=18.5, 12.0 Hz, 1H), 2.78 (dd, J=18.4, 4.4 Hz, 1H), 2.65-2.43 (m, 2H), 2.34 (t, J=6.7 Hz, 2H).

4-(3-(4-(4-Bromophenyl)-2-oxo-1,2-dihydroquinolin-3-yl)-5-phenyl-4,5-dihydro-1H-pyrazol-1-yl)-4-oxobutanoic acid (24) (997-55, GluN2D-371). Compound 24 (997-55) was prepared according to general procedure G using dihydrofuran-2,5-dione (0.023 g, 0.23 mmol) and 24f (0.100 g, 0.23 mmol). The title compound was obtained after purifying using flash chromatography (0-10% MeOH:DCM) as an off-white solid. Yield 0.110 g, 86%. $^1$H NMR (400 MHz, DMSO-$d_6$) δ 12.29 (s, 1H), 12.20 (s, 1H), 7.76 (d, J=8.0 Hz, 1H), 7.67-7.54 (m, 2H), 7.47-7.34 (m, 2H), 7.23 (d, J=5.4 Hz, 4H), 7.15 (t, J=7.6 Hz, 1H), 7.03 (d, J=8.3 Hz, 1H), 6.77 (d, J=6.7 Hz, 2H), 5.32 (dd, J=11.8, 4.7 Hz, 1H), 3.75 (dd, J=18.2, 11.9 Hz, 1H), 2.77 (dd, J=18.3, 4.5 Hz, 1H), 2.62-2.48 (m, 1H), 2.41 (s, 1H), 2.33 (t, J=6.7 Hz, 2H).

4-(5-(4-Bromophenyl)-3-(4-(4-chlorophenyl)-2-oxo-1,2-dihydroquinolin-3-yl)-4,5-dihydro-1H-pyrazol-1-yl)-4-oxobutanoic acid (25) (997-54, GluN2D-368). Compound 25 (997-54) was prepared according to general procedure G using dihydrofuran-2,5-dione (0.031 g, 0.31 mmol) and 25f 3-(5-(4-bromophenyl)-4,5-dihydro-1H-pyrazol-3-yl)-4-(4-chlorophenyl)quinolin-2(1H)-one (0.15 g, 0.31 mmol). The title compound was obtained after purifying using flash chromatography (0-10% MeOH:DCM) as an off-white solid. Yield 0.048 g, 27%. $^1$H NMR (400 MHz, DMSO-$d_6$) δ 12.30 (s, 1H), 7.64-7.48 (m, 2H), 7.42 (t, J=7.9 Hz, 5H), 7.28 (d, J=8.2 Hz, 1H), 7.15 (t, J=7.6 Hz, 1H), 7.02 (d, J=8.1 Hz, 1H), 6.74 (d, J=8.0 Hz, 2H), 5.33 (dd, J=11.9, 4.4 Hz, 1H), 3.72 (dd, J=18.5, 12.0 Hz, 1H), 2.79-2.69 (m, 1H), 2.53-2.36 (m, 2H), 2.32 (t, J=6.9 Hz, 2H).

4-(5-(4-Chlorophenyl)-3-(4-(4-chlorophenyl)-2-oxo-1,2-dihydroquinolin-3-yl)-4,5-dihydro-1H-pyrazol-1-yl)-4-oxobutanoic acid (26) (997-23, GluN2D-135). Compound 26 (997-23) was prepared according to general procedure G using dihydrofuran-2,5-dione (0.046 g, 0.460 mmol) and 26f (0.200 g, 0.460 mmol). The title compound was obtained after removing the THF under vacuum, precipitating from EtOAc with hexanes and further purification using flash chromatography (2-10% MeOH:DCM) as a yellow solid. Yield 0.054 g, 22%. $^1$H NMR (400 MHz, DMSO-$d_6$) δ 12.29 (s, 1H), 12.06 (s, 1H), 7.65-7.55 (m, 2H), 7.52 (dd, J=8.2, 2.3 Hz, 1H), 7.48-7.38 (m, 2H), 7.34-7.24 (m, 3H), 7.15 (t, J=7.6 Hz, 1H), 7.03 (d, J=8.1 Hz, 1H), 6.82 (d, J=8.5 Hz, 2H), 5.35 (dd, J=11.9, 4.5 Hz, 1H), 3.73 (dd, J=18.5, 12.0 Hz, 1H), 2.77 (dd, J=18.4, 4.4 Hz, 1H), 2.65-2.43 (m, 2H), 2.34 (t, J=6.7 Hz, 2H).

4-(3-(4-(4-Chlorophenyl)-2-oxo-1,2-dihydroquinolin-3-yl)-5-(4-fluorophenyl)-4,5-dihydro-1H-pyrazol-1-yl)-4-oxobutanoic acid (27) (997-52, GluN2D-366). Compound 27 was prepared according to general procedure G using dihydrofuran-2,5-dione (0.029 g, 0.287 mmol) and 27f (0.120 g, 0.287 mmol). The title compound was obtained after removal of the residual solvent, dissolving the crude material in DCM and washing 3× with brine. The organics were collected, dried over magnesium sulfate and concentrated to yield the title compound as a brown solid. Yield 0.085 g, 57%. $^1$H NMR (400 MHz, DMSO-$d_6$) δ 12.30 (s, 1H), 12.08 (s, 1H), 7.65-7.49 (m, 3H), 7.47-7.34 (m, 2H), 7.34-7.26 (m, 1H), 7.15 (t, J=7.7 Hz, 1H), 7.10-7.00 (m, 3H), 6.88-6.80 (m, 2H), 5.35 (dd, J=11.7, 4.3 Hz, 1H), 3.72 (dd, J=18.1, 12.0 Hz, 1H), 2.78 (dd, J=18.5, 4.3 Hz, 1H), 2.64-2.42 (m, 2H), 2.33 (t, J=6.6 Hz, 2H).

4-(3-(4-(4-Chlorophenyl)-2-oxo-1,2-dihydroquinolin-3-yl)-5-phenyl-4,5-dihydro-1H-pyrazol-1-yl)-4-oxobutanoic acid (28) (997-53, GluN2D-367). Compound 28 (997-53) was prepared according to general procedure G using dihydrofuran-2,5-dione (0.055 g, 0.550 mmol) and 28f (0.220 g, 0.550 mmol). The title compound was obtained by filtering from DCM after removal of the THF in vacuo. Yield 0.204 g, 74%. $^1$H NMR (400 MHz, DMSO-$d_6$) δ 12.29 (s, 1H), 12.13 (s, 1H), 7.66-7.54 (m, 2H), 7.54-7.39 (m, 3H), 7.32-7.11 (m, 5H), 7.03 (d, J=8.1 Hz, 1H), 6.77 (dd, J=6.5, 3.0 Hz, 2H), 5.32 (dd, J=11.9, 4.3 Hz, 1H), 3.75 (dd, J=18.4, 12.1 Hz, 1H), 2.77 (dd, J=18.3, 4.3 Hz, 1H), 2.64-2.39 (m, 2H), 2.33 (t, J=6.6 Hz, 2H).

4-(5-(4-Chlorophenyl)-3-(4-(4-fluorophenyl)-2-oxo-1,2-dihydroquinolin-3-yl)-4,5-dihydro-1H-pyrazol-1-yl)-4-oxobutanoic acid (29) (997-24, GluN2D-136). Compound 29 (997-24) was prepared according to general procedure G using dihydrofuran-2,5-dione (0.072 g, 0.718 mmol) and 29f (0.300 g, 0.718 mmol). The title compound was obtained by filtering from DCM after removal of the THF in vacuo. Yield 0.210 g, 57%. $^1$H NMR (400 MHz, DMSO-$d_6$) δ 12.27 (s, 1H), 12.09 (s, 1H), 7.58 (t, J=7.7 Hz, 1H), 7.43 (d, J=7.6 Hz, 2H), 7.40-7.25 (m, 5H), 7.15 (t, J=7.7 Hz, 1H), 7.04 (d, J=8.2 Hz, 1H), 6.86 (d, J=8.2 Hz, 2H), 5.34 (dd, J=11.9, 4.6 Hz, 1H), 3.74 (dd, J=18.5, 11.9 Hz, 1H), 2.79 (dd, J=18.4, 4.6 Hz, 1H), 2.64-2.42 (m, 2H), 2.33 (t, J=6.8 Hz, 2H).

4-(5-(4-Chlorophenyl)-3-(2-oxo-4-p-tolyl-1,2-dihydroquinolin-3-yl)-4,5-dihydro-1H-pyrazol-1-yl)-4-oxobutanoic acid (30)(997-26, GluN2D-153). Compound 30 (997-26) was prepared according to general procedure G using dihydrofuran-2,5-dione (0.060 g, 0.604 mmol) and 30f (0.250 g, 0.604 mmol). The title compound was obtained as a yellow solid after purifying using flash chromatography (2-10% MeOH:DCM) followed by precipitation from EtOAc using hexanes. Yield 0.260 g, 84%. $^1$H NMR (400 MHz, DMSO-$d_6$) δ 12.24 (s, 1H), 12.08 (s, 1H), 7.57 (t, J=7.5 Hz, 1H), 7.42 (d, J=8.2 Hz, 1H), 7.36-7.21 (m, 5H), 7.18-7.04 (m, 3H), 6.84 (dd, J=8.5, 2.3 Hz, 2H), 5.32 (dd, J=11.9, 4.4 Hz, 1H), 3.68 (dd, J=18.4, 12.0 Hz, 1H), 2.74 (dd, J=18.4, 4.5 Hz, 1H), 2.63-2.39 (m, 5H), 2.31 (t, J=6.7 Hz, 2H).

4-(5-(4-Chlorophenyl)-3-(4-(4-methoxyphenyl)-2-oxo-1,2-dihydroquinolin-3-yl)-4,5-dihydro-1H-pyrazol-1-yl)-4-oxobutanoic acid (31) (997-21, GluN2D-139). Compound 31 (997-21) was prepared according to general procedure G using dihydrofuran-2,5-dione (0.047 g, 0.465 mmol) and 31f (0.200 g, 0.465 mmol). The title compound was obtained by filtering from DCM after removal of the THF in vacuo. Yield 0.165 g, 67%. $^1$H NMR (400 MHz, DMSO-$d_6$) δ 14.05 (s, 1H), 12.24 (s, 1H), 7.57 (t, J=7.7 Hz, 1H), 7.42 (d, J=8.3 Hz, 2H), 7.38-7.06 (m, 6H), 7.01 (d, J=8.5 Hz, 2H), 6.83 (d, J=7.8 Hz, 3H), 5.33 (dd, J=11.8, 4.4 Hz, 1H), 3.85 (s, 3H), 3.67 (dd, J=18.4, 12.1 Hz, 1H), 2.78-2.53 (m, 2H), 2.41-2.22 (m, 2H).

4-(5-(4-Chlorophenyl)-3-(4-(4-cyanophenyl)-2-oxo-1,2-dihydroquinolin-3-yl)-4,5-dihydro-1H-pyrazol-1-yl)-4-oxobutanoic acid (32) (997-27, GluN2D-154). Compound 32 (997-27) was prepared according to general procedure G using dihydrofuran-2,5-dione (0.059 g, 0.588 mmol) and 32f (0.150 g, 0.588 mmol). The title compound was obtained as a yellow solid after precipitation from EtOAc using hexanes followed by purification using flash chromatography with 10% MeOH:DCM as a yellow solid. Yield 0.150 g, 48.6%. $^1$H NMR (400 MHz, DMSO-$d_6$) δ 12.33 (s, 1H), 12.09 (s, 1H), 7.97 (ddd, J=11.8, 7.7, 1.7 Hz, 2H), 7.64-7.56 (m, 2H), 7.50 (dd, J=7.8, 1.7 Hz, 1H), 7.43 (d, J=8.1 Hz, 1H), 7.35-7.27 (m, 2H), 7.14 (t, J=7.7 Hz, 1H), 6.95 (dd, J=8.2, 1.2 Hz, 1H), 6.89-6.84 (m, 2H), 5.35 (dd, J=12.0, 4.4 Hz, 1H), 3.79 (dd, J=18.5, 12.0 Hz, 1H), 2.89 (dd, J=18.5, 4.5 Hz, 1H), 2.57-2.23 (m, 4H).

4-(5-(4-Chlorophenyl)-3-(2-oxo-4-(4-(trifluoromethyl)phenyl)-1,2-dihydroquinolin-3-yl)-4,5-dihydro-1H-pyrazol-1-yl)-4-oxobutanoic acid (33) (997-36, GluN2D-204). Compound 33 (997-36) was prepared according to general procedure G using dihydrofuran-2,5-dione (0.039 g, 0.385 mmol) and 33f (0.180 g, 0.220 mmol). The title compound was obtained after flash column chromatography using 0-10% MeOH:DCM and precipitation from EtOAc using hexanes as a yellow solid. Yield 0.125 g, 57.2%. $^1$H NMR (400 MHz, DMSO-$d_6$) δ 12.34 (s, 1H), 12.07 (s, 1H), 7.88 (dd, J=19.4, 8.1 Hz, 2H), 7.65 (d, J=8.1 Hz, 1H), 7.59 (t, J=7.6 Hz, 1H), 7.53 (d, J=8.1 Hz, 1H), 7.45 (d, J=8.2 Hz, 1H), 7.26 (d, J=8.2 Hz, 2H), 7.15 (t, J=7.7 Hz, 1H), 6.98 (d, J=8.1 Hz, 1H), 6.86 (d, J=8.2 Hz, 2H), 5.36 (dd, J=12.0, 4.6 Hz, 1H), 3.80 (dd, J=18.4, 12.0 Hz, 1H), 2.91 (dd, J=18.5, 4.8 Hz, 1H), 2.52-2.39 (m, 1H), 2.40-2.21 (m, 3H).

4-(5-(4-Chlorophenyl)-3-(4-(3-fluorophenyl)-2-oxo-1,2-dihydroquinolin-3-yl)-4,5-dihydro-1H-pyrazol-1-yl)-4-oxobutanoic acid (34) (997-28, GluN2D-156). Compound 34 (997-28) was prepared according to general procedure G using dihydrofuran-2,5-dione (0.060 g, 0.598 mmol) and 34f (0.250 g, 0.367 mmol). The title compound was obtained after precipitating from EtOAc using hexanes followed by flash column chromatography using 10% MeOH:DCM, as a yellow solid. Yield 0.190 g, 61.3%. $^1$H NMR (400 MHz, DMSO-$d_6$) δ 12.24 (s, 1H), 12.08 (s, 1H), 7.57 (t, J=7.5 Hz, 1H), 7.42 (d, J=8.2 Hz, 1H), 7.36-7.21 (m, 5H), 7.18-7.04 (m, 3H), 6.84 (d, J=8.2 Hz, 2H), 5.32 (dd, J=12.0, 4.5 Hz, 1H), 3.68 (dd, J=18.5, 12.0 Hz, 1H), 2.74 (dd, J=18.5, 4.5 Hz, 1H), 2.52-2.39 (m, 4H).

4-(5-(4-Chlorophenyl)-3-(4-(3-chlorophenyl)-2-oxo-1,2-dihydroquinolin-3-yl)-4,5-dihydro-1H-pyrazol-1-yl)-4-oxobutanoic acid (35) (997-22, GluN2D-140). Compound 35 (997-22) was prepared according to general procedure G using dihydrofuran-2,5-dione (0.069 g, 0.691 mmol) and 35f (0.300 g, 0.691 mmol). The title compound was obtained as a yellow solid after flash column chromatography using 2-10% MeOH:DCM. Yield 0.170 g, 46.1%. $^1$H NMR (600 MHz, DMSO-$d_6$) δ 12.25 (s, 1H), 12.04 (s, 1H), 7.58-7.51 (m, 2H), 7.51-7.46 (m, 1H), 7.39 (d, J=8.2 Hz, 1H), 7.36-7.32 (m, 1H), 7.25 (ddt, J=7.1, 4.9, 2.5 Hz, 2H), 7.19 (d, J=7.5 Hz, 1H), 7.12 (t, J=7.7 Hz, 1H), 7.01-6.94 (m, 1H), 6.81-6.73 (m, 2H), 5.34-5.28 (m, 1H), 3.83-3.74 (m, 1H), 2.84-2.70 (m, 1H), 2.52-2.34 (m, 2H), 2.31-2.24 (m, 2H).

4-(5-(4-Chlorophenyl)-3-(2-oxo-4-(m-tolyl)-1,2-dihydroquinolin-3-yl)-4,5-dihydro-1H-pyrazol-1-yl)-4-oxobutanoic acid (36) (997-25, gluN2D-152). Compound 36 (997-25) was prepared according to general procedure G using dihydrofuran-2,5-dione (0.060 g, 0.604 mmol) and 36f (0.250 g, 0.604 mmol). The title compound was obtained as a yellow solid after flash column chromatography using 0-10% MeOH:DCM followed by precipitation from hot EtOAc and hexanes. Yield 0.240 g, 77.0%. $^1$H NMR (400 MHz, DMSO-$d_6$) δ 12.21 (s, 1H), 12.05 (s, 1H), 7.53 (t, J=7.6 Hz, 1H), 7.42-7.27 (m, 3H), 7.27-7.17 (m, 2H), 7.16-7.06 (m, 2H), 7.00 (q, J=10.2, 8.9 Hz, 2H), 6.80-6.67 (m, 2H), 5.33-5.23 (m, 1H), 3.80-3.62 (m, 1H), 2.76 (dd, J=18.4, 4.6 Hz, 0.5H), 2.64 (dd, J=18.5, 4.6 Hz, 0.5H), 2.57-2.34 (m, 5H), 2.31-2.18 (m, 2H).

4-(5-(4-Chlorophenyl)-3-(4-(3-methoxyphenyl)-2-oxo-1,2-dihydroquinolin-3-yl)-4,5-dihydro-1H-pyrazol-1-yl)-4-oxobutanoic acid (37) (997-39, GluN2D-224). Compound 37 (997-39) was prepared according to general procedure G using dihydrofuran-2,5-dione (0.070 g, 0.698 mmol) and 37f (0.300 g, 0.698 mmol). The title compound was obtained as a yellow solid after flash column chromatography with two columns using 0-10% MeOH:DCM. Yield 0.090 g, 24.3%. $^1$H NMR (600 MHz, DMSO-$d_6$) δ 12.23 (s, 1H), 12.03 (s, 1H), 7.57 (t, J=7.8 Hz, 1H), 7.48-7.35 (m, 2H), 7.26 (dd, J=22.1, 8.1 Hz, 2H), 7.18-7.12 (m, 1H), 7.09 (t, J=8.3 Hz, 2H), 6.95 (d, J=9.9 Hz, 1H), 6.85-6.72 (m, 3H), 5.37-5.30 (m, 1H), 3.84-3.64 (m, 4H), 2.83-2.72 (m, 1H), 2.60-2.51 (m, 2H), 2.31 (t, J=7.1 Hz, 2H).

4-(5-(4-Chlorophenyl)-3-(4-(3-cyanophenyl)-2-oxo-1,2-dihydroquinolin-3-yl)-4,5-dihydro-1H-pyrazol-1-yl)-4-oxobutanoic acid (38) (997-40, GluN2D-225). Compound 38 (997-40) was prepared according to general procedure G using dihydrofuran-2,5-dione (0.021 g, 0.212 mmol) and 38f (0.090 g, 0.212 mmol). The title compound was obtained as a yellow solid after flash column chromatography using 0-10% MeOH:DCM. Yield 0.034 g, 31.0%. $^1$H NMR (400 MHz, DMSO-$d_6$) δ 12.35 (d, J=3.6 Hz, 1H), 12.10 (s, 1H), 8.04-7.91 (m, 1H), 7.84-7.67 (m, 2H), 7.65-7.55 (m, 2H), 7.43 (d, J=8.2 Hz, 1H), 7.31 (d, J=8.3 Hz, 2H), 7.16 (t, J=7.7 Hz, 1H), 6.97 (d, J=8.2 Hz, 1H), 6.82 (dd, J=13.4, 8.2 Hz, 2H), 5.40-5.32 (m, 1H), 3.96-3.81 (m, 1H), 2.87 (dt, J=18.3, 4.1 Hz, 1H), 2.42 (d, J=7.6 Hz, 2H), 2.35-2.26 (m, 2H).

4-(5-(4-Chlorophenyl)-3-(2-oxo-4-(3-(trifluoromethyl)phenyl)-1,2-dihydroquinolin-3-yl)-4,5-dihydro-1H-pyrazol-1-yl)-4-oxobutanoic acid (39) (997-51, GluN2D-365). Compound 39 (997-51) was prepared according to general procedure G using dihydrofuran-2,5-dione (0.054 g, 0.53 mmol) and 39f (0.250 g, 0.53 mmol). The title compound was obtained as a yellow solid using a 0-8% MeOH gradient in DCM. Yield 0.073 g, 24%. $^1$H NMR (400 MHz, DMSO-$d_6$) δ 12.34 (s, 1H), 12.06 (s, 1H), 7.96-7.84 (m, 2H), 7.82-7.66 (m, 1H), 7.59 (t, J=8.4 Hz, 2H), 7.44 (d, J=8.3 Hz, 1H), 7.28 (d, J=8.2 Hz, 1H), 7.23 (d, J=8.1 Hz, 1H), 7.20-7.13 (m, 1H), 6.95 (dd, J=23.9, 8.2 Hz, 1H), 6.84 (d, J=8.1 Hz, 1H), 6.76 (d, J=8.0 Hz, 1H), 5.34 (dt, J=12.2, 4.3 Hz, 1H), 3.95-3.70 (m, 1H), 3.00-2.74 (m, 1H), 2.54-2.23 (m, 4H).

4-(3-(4-(4-Chloro-3-fluorophenyl)-2-oxo-1,2-dihydroquinolin-3-yl)-5-(4-chlorophenyl)-4,5-dihydro-1H-pyrazol-1-yl)-4-oxobutanoic acid (40) (997-38, GluN2D-218). Compound 40 (997-38) was prepared according to general procedure G using dihydrofuran-2,5-dione (0.040 g, 0.398 mmol) and 40f (0.180 g, 0.398 mmol). The title compound was obtained after flash column chromatography using 0-10% MeOH:DCM as a yellow solid. Yield 0.096 g, 43.7%. $^1$H NMR (400 MHz, DMSO-$d_6$) δ 12.33 (s, 1H), 12.12 (s, 1H), 7.79-7.64 (m, 1H), 7.62-7.51 (m, 2H), 7.46-7.38 (m, 2H), 7.33-7.23 (m, 2H), 7.21-7.00 (m, 2H), 6.93-6.78 (m, 2H), 5.39 (dt, J=12.1, 4.4 Hz, 1H), 3.85-3.72 (m, 1H), 2.91-2.79 (m, 1H), 2.66-2.39 (m, 2H), 2.34 (td, J=7.0, 2.2 Hz, 2H).

4-(3-(4-(3-Chloro-4-fluorophenyl)-2-oxo-1,2-dihydroquinolin-3-yl)-5-(4-chlorophenyl)-4,5-dihydro-1H-pyrazol-1-yl)-4-oxobutanoic acid (41) (997-34, GluN2D-202). Compound 41 (997-34) was prepared according to general procedure G using dihydrofuran-2,5-dione (0.040 g, 0.398 mmol) and 41f (0.180 g, 0.398 mmol). The title compound was obtained after purifying using flash column chromatography using 0-10% MeOH:DCM as a yellow solid. Yield 0.120 g, 55.0%. $^1$H NMR (400 MHz, DMSO-$d_6$) δ 12.32 (s, 1H), 12.12 (s, 1H), 7.73-7.50 (m, 3H), 7.44 (dd, J=8.2, 1.7 Hz, 2H), 7.29 (td, J=8.8, 2.0 Hz, 2H), 7.17 (t, J=7.6 Hz, 1H), 7.09-7.01 (m, 1H), 6.88 (dt, J=8.6, 2.4 Hz, 2H), 5.38 (dd, J=10.4, 4.6 Hz, 1H), 3.90-3.76 (m, 1H), 2.93-2.77 (m, 1H), 2.66-2.40 (m, 2H), 2.40-2.28 (m, 2H).

4-(5-(4-Chlorophenyl)-3-(4-(3,4-dichlorophenyl)-2-oxo-1,2-dihydroquinolin-3-yl)-4,5-dihydro-1H-pyrazol-1-yl)-4-oxobutanoic acid (42) (997-41, GluN2D-228). Compound 42 (997-41) was prepared according to general procedure G using dihydrofuran-2,5-dione (0.043 g, 0.427 mmol) and 42f (0.200 g, 0.427 mmol). The title compound was obtained after purifying flash column chromatography using 0-10% MeOH:DCM as a yellow solid. Yield 0.102 g, 42.0%. $^1$H NMR (400 MHz, DMSO-$d_6$) δ 12.31 (s, 1H), 12.10 (s, 1H), 7.83-7.70 (m, 1H), 7.63-7.54 (m, 2H), 7.46-7.37 (m, 2H), 7.32-7.22 (m, 2H), 7.16 (t, J=7.7 Hz, 1H), 7.04 (t, J=7.0 Hz, 1H), 6.87-6.80 (m, 2H), 5.37 (dd, J=12.0, 4.3 Hz, 1H), 3.88-3.74 (m, 1H), 2.90-2.74 (m, 1H), 2.53-2.39 (m, 2H), 2.38-2.29 (m, 2H).

4-(5-(4-Chlorophenyl)-3-(4-(3,4-difluorophenyl)-2-oxo-1,2-dihydroquinolin-3-yl)-4,5-dihydro-1H-pyrazol-1-yl)-4-oxobutanoic acid (43) (997-42, GluN2D-229). Compound 43 (997-41) was prepared according to general procedure G using dihydrofuran-2,5-dione (0.0427 g, 0.427 mmol) and 43f (0.200 g, 0.427 mmol). The title compound was obtained after flash column chromatography using 0-10% MeOH:DCM as a yellow solid. Yield 0.110 g, 69%. $^1$H NMR (400 MHz, DMSO-$d_6$) δ 12.31 (s, 1H), 12.13 (s, 1H), 7.63-7.52 (m, 3H), 7.46-7.39 (m, 1H), 7.35-7.28 (m, 1H), 7.29-7.23 (m, 2H), 7.20-7.10 (m, 1H), 7.06 (d, J=8.2 Hz, 1H), 6.95-6.84 (m, 2H), 5.43-5.33 (m, 1H), 3.88-3.73 (m, 1H), 2.86 (dd, J=18.5, 4.4 Hz, 1H), 2.66-2.29 (m, 4H).

4-(5-(4-Chlorophenyl)-3-(4-(3,5-difluorophenyl)-2-oxo-1,2-dihydroquinolin-3-yl)-4,5-dihydro-1H-pyrazol-1-yl)-4-oxobutanoic acid (44) (997-35, GluN2D-203). Compound 44 (997-35) was prepared according to general procedure G using dihydrofuran-2,5-dione (0.041 g, 0.413 mmol) and 44f (0.180 g, 0.413 mmol). The title compound as a yellow solid was obtained after purifying using flash column chromatography with 0-10% MeOH:DCM. Yield 0.133 g, 56.5%. $^1$H NMR (400 MHz, DMSO-$d_6$) δ 12.33 (s, 1H), 12.07 (s, 1H), 7.59 (t, J=7.7 Hz, 1H), 7.47-7.33 (m, 2H), 7.29 (d, J=8.2 Hz, 2H), 7.23 (d, J=8.5 Hz, 1H), 7.17 (t, J=7.6 Hz, 1H), 7.08 (d, J=8.0 Hz, 2H), 6.89 (d, J=8.1 Hz, 2H), 5.40 (dd, J=12.0, 4.6 Hz, 1H), 3.86 (dd, J=18.4, 12.0 Hz, 1H), 2.90 (dd, J=18.5, 4.6 Hz, 1H), 2.59-2.41 (m, 2H), 2.33 (t, J=6.8 Hz, 2H).

4-(5-(4-Chlorophenyl)-3-(4-(3,5-dichloro (phenyl)-2-oxo-1,2-dihydroquinolin-3-yl)-4,5-dihydro-1H-pyrazol-1-yl)-4-oxobutanoic acid (45) (997-37, GluN2D-205). Compound 45 (997-37) was prepared according to general procedure G using dihydrofuran-2,5-dione (0.038 g, 0.384 mmol) and 45f (0.180 g, 0.384 mmol). The title compound was obtained as a yellow solid after purifying using flash column chromatography with 0-10% MeOH:DCM. Yield 0.080 g, 36.6%. $^1$H NMR (400 MHz, DMSO-$d_6$) δ 12.33 (s, 1H), 12.10 (s, 1H), 7.84-7.71 (m, 1H), 7.64-7.56 (m, 2H), 7.51-7.39 (m, 2H), 7.29 (t, J=7.3 Hz, 2H), 7.17 (t, J=7.6 Hz, 1H), 7.06 (t, J=6.9 Hz, 1H), 6.84 (d, J=8.1 Hz, 2H), 5.39 (dd, J=12.0, 4.3 Hz, 1H), 3.89-3.75 (m, 1H), 2.85-2.67 (m, 1H), 2.64-2.30 (m, 4H).

4-(5-(4-Chlorophenyl)-3-(4-(4-chlorophenyl)-6-methyl-2-oxo-1,2-dihydroquinolin-3-yl)-4,5-dihydro-1H-pyrazol-1-yl)-4-oxobutanoic acid (46) (997-43, GluN2D-301). Compound 46 (997-43) was prepared according to general procedure G using dihydrofuran-2,5-dione (0.039 g, 0.39 mmol) and 46f (0.175 g, 0.39 mmol). The title compound was obtained after flash column chromatography using 0-8% MeOH:DCM as a yellow solid. Yield, 0.114 g, 53%. $^1$H NMR (400 MHz, DMSO-$d_6$) δ 12.18 (s, 1H), 11.79 (s, 1H), 7.56 (dt, J=8.2, 2.3 Hz, 1H), 7.48 (dt, J=8.2, 2.3 Hz, 1H), 7.41-7.34 (m, 2H), 7.30 (dd, J=8.3, 2.2 Hz, 1H), 7.27-7.20 (m, 3H), 6.80-6.72 (m, 3H), 5.35-5.25 (m, 1H), 3.75-3.59 (m, 1H), 2.76-2.65 (m, 1H), 2.61-2.33 (m, 2H), 2.30 (m, 2H), 2.19 (s, 3H).

4-(5-(4-Chlorophenyl)-3-(4-(3-fluorophenyl)-6-methyl-2-oxo-1,2-dihydroquinolin-3-yl)-4,5-dihydro-1H-pyrazol-1-yl)-4-oxobutanoic acid (47) (997-44, GluN2D-329). Compound 47 (997-44) was prepared according to general procedure G using dihydrofuran-2,5-dione (0.037 g, 0.37 mmol) and 47f (0.160 g, 0.37 mmol). The title compound was obtained after flash column chromatography using 0-10% MeOH:DCM as a brown solid. Yield 0.094 g, 48%. $^1$H NMR (400 MHz, DMSO-$d_6$) δ 12.24 (s, 1H), 12.12 (s, 1H), 7.64-7.47 (m, 1H), 7.42 (d, J=8.5 Hz, 1H), 7.40-7.32 (m, 2H), 7.32-7.22 (m, 3H), 7.11 (dd, J=23.8, 8.5 Hz, 1H), 6.86-6.77 (m, 3H), 5.35 (dt, J=12.5, 3.4 Hz, 1H), 3.80 (dd, J=18.6, 12.1 Hz, 1H), 2.81 (dt, J=18.5, 5.2 Hz, 1H), 2.53-2.39 (m, 2H), 2.31 (t, J=6.8 Hz, 2H), 2.23 (s, 3H).

4-(3-(6-Chloro-4-(4-chlorophenyl)-2-oxo-1,2-dihydroquinolin-3-yl)-5-(4-chlorophenyl)-4,5-dihydro-1H-pyrazol-1-yl)-4-oxobutanoic acid (48) (997-46, GluN2D-337). Compound 48 (997-46) was prepared according to general procedure G using dihydrofuran-2,5-dione (0.038 g, 0.38 mmol) and 48f (0.180 g, 0.38 mmol). The title compound was obtained as a yellow solid after flash column chromatography using 0-8% MeOH:DCM. Yield 0.033 g, 15%. $^1$H NMR (400 MHz, DMSO-$d_6$) δ 12.44 (s, 1H), 12.08 (s, 1H), 7.69-7.58 (m, 2H), 7.54 (dd, J=8.2, 2.3 Hz, 1H), 7.44 (dd, J=8.5, 2.7 Hz, 2H), 7.35-7.23 (m, 3H), 6.93 (d, J=2.3 Hz, 1H), 6.85-6.76 (m, 2H), 5.35 (dd, J=12.0, 4.4 Hz, 1H), 3.72 (dd, J=18.5, 12.0 Hz, 1H), 2.76 (dd, J=18.5, 4.4 Hz, 1H), 2.64-2.38 (m, 2H), 2.33 (t, J=6.7 Hz, 2H).

4-(3-(6-Chloro-4-(3-fluorophenyl)-2-oxo-1,2-dihydroquinolin-3-yl)-5-(4-chlorophenyl)-4,5-dihydro-1H-pyrazol-1-yl)-4-oxobutanoic acid (49) (997-45, GluN2D-336). Compound 49 (997-45) was prepared according to general procedure G using dihydrofuran-2,5-dione (0.035 g, 0.35 mmol) and 49f (0.160 g, 0.35 mmol). The title compound was obtained as a yellow solid after flash column chromatography using 0-8% MeOH:DCM. Yield 0.039 g, 20%. $^1$H NMR (600 MHz, DMSO-$d_6$) δ 12.45 (s, 1H), 12.05 (s, 1H), 7.65 (dd, J=8.8, 2.5 Hz, 1H), 7.63-7.53 (m, 1H), 7.45 (d, J=8.8 Hz, 1H), 7.42-7.32 (m, 2H), 7.30 (d, J=8.2 Hz, 1H), 7.29-7.25 (m, 1H), 7.19 (dd, J=9.2, 2.1 Hz, 1H), 7.12 (d, J=7.5 Hz, 1H), 6.94 (d, J=2.4 Hz, 1H), 6.83 (dd, J=11.9, 8.3 Hz, 2H), 5.36 (dt, J=12.2, 4.6 Hz, 1H), 2.88-2.80 (m, 1H), 2.51-2.44 (m, 2H), 2.31 (t, J=6.9 Hz, 2H).

4-(5-(4-Chlorophenyl)-3-(4-(4-chlorophenyl)-6-fluoro-2-oxo-1,2-dihydroquinolin-3-yl)-4,5-dihydro-1H-pyrazol-1-yl)-4-oxobutanoic acid (50) (997-49, GluN2D-344). Compound 50 (997-49) was prepared according to general procedure G using dihydrofuran-2,5-dione (0.035 g, 0.35 mmol) and 50f (0.19 g, 0.42 mmol). The title compound was obtained after flash column chromatography using 0-10% MeOH:DCM as a yellow solid. Yield 0.151 g, 65.0%. $^1$H NMR (600 MHz, DMSO-$d_6$) δ 12.37 (s, 1H), 12.07 (s, 1H), 7.61 (dd, J=8.2, 2.4 Hz, 1H), 7.56-7.41 (m, 4H), 7.34-7.25 (m, 3H), 6.85-6.78 (m, 2H), 6.71 (dd, J=9.7, 2.9 Hz, 1H), 5.36 (dd, J=12.0, 4.5 Hz, 1H), 3.73 (dd, J=18.5, 12.1 Hz, 1H), 2.78 (dd, J=18.5, 4.4 Hz, 1H), 2.62-2.54 (m, 1H), 2.53-2.40 (m, 1H), 2.33 (t, J=6.7 Hz, 2H).

4-(5-(4-Chlorophenyl)-3-(6-fluoro-4-(3-fluorophenyl)-2-oxo-1,2-dihydroquinolin-3-yl)-4,5-dihydro-1H-pyrazol-1-yl)-4-oxobutanoic acid (51) (997-50, GLuN2D-345). Compound 51 (997-50) was prepared according to general procedure G using dihydrofuran-2,5-dione (0.041 g, 0.41 mmol) and 51f (0.180 g, 0.41 mmol). The title compound was obtained after flash column chromatography using 0-10% MeOH:DCM as a yellow solid. Yield 0.076 g, 34.0%. $^1$H NMR (600 MHz, DMSO-$d_6$) δ 12.34 (s, 1H), 12.01 (s, 1H), 7.59-7.39 (m, 3H), 7.37-7.19 (m, 3H), 7.14 (t, J=7.8 Hz, 1H), 7.07 (t, J=7.2 Hz, 1H), 6.83-6.75 (m, 2H), 6.74-6.63 (m, 1H), 5.40-5.33 (m, 1H), 3.81 (dd, J=18.5, 12.1 Hz, 2H), 2.85-2.75 (m, 1H), 2.46-2.36 (m, 2H), 2.27 (t, J=7.0 Hz, 2H).

4-(5-(4-Chlorophenyl)-3-(4-(4-chlorophenyl)-6-methoxy-2-oxo-1,2-dihydroquinolin-3-yl)-4,5-dihydro-1H-pyrazol-1-yl)-4-oxobutanoic acid (52) (997-47, GluN2D-340). Compound 52 (997-47) was prepared according to general procedure G using dihydrofuran-2,5-dione (0.039 g, 0.39 mmol) and 52f (0.180 g, 0.39 mmol). The title compound was obtained as a yellow solid after flash column chromatography using 0-10% MeOH:DCM. Yield 0.095 g, 43.0%. $^1$H NMR (600 MHz, DMSO-d6) δ 12.19 (s, 1H), 12.09 (s, 1H), 7.61 (dd, J=8.2, 2.4 Hz, 1H), 7.52 (dd, J=8.2, 2.4 Hz, 1H), 7.42 (dd, J=8.2, 2.3 Hz, 1H), 7.39 (d, J=8.8 Hz, 1H), 7.32-7.25 (m, 4H), 6.82 (d, J=8.5 Hz, 2H), 6.42 (d, J=2.8 Hz, 1H), 5.34 (dd, J=11.9, 4.5 Hz, 1H), 3.73 (dd, J=18.4, 12.0 Hz, 1H), 3.60 (s, 3H), 2.77 (dd, J=18.4, 4.4 Hz, 1H), 2.63-2.44 (m, 2H), 2.33 (t, J=6.6 Hz, 2H).

4-(5-(4-Chlorophenyl)-3-(4-(3-fluorophenyl)-6-methoxy-2-oxo-1,2-dihydroquinolin-3-yl)-4,5-dihydro-1H-pyrazol-1-yl)-4-oxobutanoic acid (53) (997-48, GluN2D-341). Compound 53 (997-48) was prepared according to general procedure G using dihydrofuran-2,5-dione (0.027 g, 0.27 mmol) and 53f (0.120 g, 0.27 mmol). The title compound was obtained as a yellow solid after flash column chromatography using 0-10% MeOH:DCM. Yield 0.040 g, 43.0%. $^1$H NMR (400 MHz, DMSO-$d_6$) δ 12.21 (s, 1H), 7.64-7.48 (m, 1H), 7.43-7.07 (m, 6H), 6.87-6.77 (m, 2H), 6.45-6.40 (m, 1H), 5.40-5.30 (m, 1H) 3.87-3.74 (m, 2H), 3.60 (s, 3H), 2.83 (dt, J=18.4, 5.2 Hz, 1H), 2.54-2.39 (m, 2H), 2.31 (dd, J=15.3, 8.6 Hz, 2H).

(Z)-4-(5-(4-Bromophenyl)-3-(6-chloro-2-oxo-4-phenyl-1,2-dihydroquinolin-3-yl)-4,5-dihydro-1H-pyrazol-1-yl)-4- oxobut-2-enoic acid (55) (997-9, gluN2D-055). Compound 55 (997-9) was prepared according to general procedure G using furan-2,5-dione (0.061 g, 0.63 mmol) and 55f (0.300 g, 0.63 mmol). The title compound was obtained after filtration from the cooled reaction medium and rinsed with THF. Yield 0.200 g, 55%. $^1$H NMR (400 MHz, DMSO-$d_6$) δ 12.69 (s, 1H), 12.41 (s, 1H), 7.64 (d, J=8.7 Hz, 1H), 7.54 (q, J=9.5, 6.9 Hz, 3H), 7.40 (dt, J=13.4, 7.9 Hz, 4H), 7.25 (d, J=7.2 Hz, 1H), 6.92 (s, 1H), 6.78 (d, J=8.1 Hz, 2H), 6.40 (d, J=12.1 Hz, 1H), 6.16 (d, J=12.1 Hz, 1H), 5.37 (dd, J=12.0, 4.9 Hz, 1H), 3.78 (dd, J=18.5, 12.0 Hz, 1H), 2.79 (dd, J=18.7, 4.8 Hz, 1H).

(E)-4-(5-(4-Bromophenyl)-3-(6-chloro-2-oxo-4-phenyl-1,2-dihydroquinolin-3-yl)-4,5-dihydro-1H-pyrazol-1-yl)-4-oxobut-2-enoic acid (54) (997-10, GluN2D-62). Compound 54 (997-10) was prepared from 54 g (0.190 g, 0.322 mmol) and 1M NaOH (1.222 mL, 1.222 mmol) were stirred to give a yellow solution. After four hours, 1M HCl (1.22 mL) was added and a yellow solid precipitated. The solid was filtered and rinsed with water to give the title compound as a yellow solid. Yield 0.170 g, 92%. $^1$H NMR (400 MHz, DMSO-$d_6$) δ 13.03 (s, 1H), 12.46 (s, 1H), 7.66 (dd, J=8.8, 2.4 Hz, 1H), 7.61-7.38 (m, 7H), 7.31 (dt, J=5.6, 2.5 Hz, 1H), 7.26 (d, J=15.7 Hz, 1H), 6.94 (d, J=2.4 Hz, 1H), 6.78 (d, J=8.3 Hz, 2H), 6.45 (d, J=15.7 Hz, 1H), 5.45 (dd, J=11.8, 4.5 Hz, 1H), 3.80 (dd, J=18.7, 11.9 Hz, 1H), 2.88 (dd, J=18.7, 4.5 Hz, 1H).

(Z)-4-(3-(4-(4-Bromophenyl)-2-oxo-1,2-dihydroquinolin-3-yl)-5-(4-chlorophenyl)-4,5-dihydro-1H-pyrazol-1-yl)-4-oxobut-2-enoic acid (59) (997-30, GluN2D-190). Compound 59 (997-30) was prepared according to general procedure G using furan-2,5-dione (0.061 g, 0.63 mmol) and 22f (0.300 g, 0.630 mmol). The THF was removed under vacuum and the resultant residue was dissolved in hot EtOAc. A yellow solid was present upon cooling which was filtered and determined to be the desired product. Yield 0.171 g, 47%. $^1$H NMR (400 MHz, DMSO-$d_6$) δ 12.74 (s, 1H), 12.30 (s, 1H), 7.75 (d, J=8.3 Hz, 1H), 7.67 (d, J=8.4 Hz, 1H), 7.58 (t, J=7.9 Hz, 1H), 7.43 (d, J=8.4 Hz, 1H), 7.32 (t, J=8.6 Hz, 3H), 7.22 (d, J=8.2 Hz, 1H), 7.15 (t, J=7.8 Hz, 1H), 7.03 (d, J=8.2 Hz, 1H), 6.87 (d, J=8.1 Hz, 2H), 6.48 (d, J=12.2 Hz, 1H), 6.20 (d, J=12.1 Hz, 1H), 5.47-5.38 (m, 1H), 3.76 (dd, J=18.8, 11.9 Hz, 1H), 2.84-2.74 (m, 1H).

(E)-4-(3-(4-(4-Bromophenyl)-2-oxo-1,2-dihydroquinolin-3-yl)-5-(4-chlorophenyl)-4,5-dihydro-1H-pyrazol-1-yl)-4-oxobut-2-enoic acid (58) (997-33, GluN2D-200). Compound 58 was prepared from compound 60 using the following method. In a 50 mL round-bottomed flask, ethanol (28.2 mL), 60 (0.500 g, 0.850 mmol) and 1M NaOH (3.22 mL, 3.22 mmol) were stirred to give a yellow solution. After four hours, 1M HCl (3.22 mL) was added and a yellow solid precipitated. The solid was filtered and rinsed with water. The resulting solid was dissolved in DCM, washed with brine and the organics were dried over magnesium sulfate in vacuo. The title compound was obtained from column chromatography (0-10% MeOH in DCM) as an off-white solid. Yield 0.320 g, 66%. $^1$H NMR (400 MHz, DMSO-$d_6$) δ 12.98 (s, 1H), 12.28 (s, 1H), 7.71-7.51 (m, 3H), 7.48-7.19 (m, 6H), 7.12 (t, J=7.6 Hz, 1H), 7.02 (d, J=8.2 Hz, 1H), 6.85 (d, J=8.2 Hz, 2H), 6.44 (d, J=15.7 Hz, 1H), 5.45 (dd, J=11.7, 4.4 Hz, 1H), 3.73 (dd, J=18.7, 11.8 Hz, 1H), 2.89 (dd, J=18.6, 4.4 Hz, 1H).

Methyl 4-(5-(4-bromophenyl)-3-(6-chloro-2-oxo-4-phenyl-1,2-dihydroquinolin-3-yl)-4,5-dihydro-1H-pyrazol-1-yl)-4-oxobutanoate (56) (997-11, GluN2D-64). Compound 56 (997-11) was prepared from 56 g (0.400 g, 0.69 mmol) in the following manner. 56 g (0.400 g, 0.69 mmol) was dissolved in 6.9 mL THF and freshly prepared HCl (Acetyl chloride added to methanol) in MeOH was added dropwise to the reaction vessel with stirring until TLC indicated completion. Upon completion, the THF was removed under vacuum, the residue dissolved in DCM, washed 3× with brine and column chromatographed using 0-10% MeOH gradient in DCM to give the title compound as a yellow solid. Yield 0.100 g, 24%. $^1$H NMR (400 MHz, DMSO-$d_6$) δ 12.42 (s, 1H), 7.64 (dd, J=8.7, 2.4 Hz, 1H), 7.54 (dtt, J=12.7, 6.4, 3.9 Hz, 3H), 7.48-7.38 (m, 4H), 7.31-7.24 (m, 1H), 6.93 (d, J=2.3 Hz, 1H), 6.77-6.70 (m, 2H), 5.31 (dd, J=12.0, 4.6 Hz, 1H), 3.76 (dd, J=18.5, 12.2 Hz, 1H), 3.59 (s, 1H), 3.54 (s, 2H), 2.79 (dd, J=18.5, 4.6 Hz, 1H), 2.61-2.42 (m, 2H), 2.37 (t, J=6.7 Hz, 2H).

(E)-Methyl 4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoate (60) (997-31, Glun2D-302 (191)). Compound 60 (997-31) was prepared from 22f (0.750 g, 1.60 mmol) and (E)-methyl 4-chloro-4-oxobut-2-enoate (0.280 g, 1.90 mmol) using standard procedure G. The THF was removed under vacuum, the residue dissolved in DCM, washed 3× with brine and the organics concentrated. The title compound was obtained as yellow solid by flash chromatography using a 0-10% MeOH gradient in DCM. Yield, 0.550 g, 59%. $^1$H NMR (600 MHz, DMSO-$d_6$) δ 12.32 (s, 1H), 7.70 (dt, J=8.3, 1.9 Hz, 1H), 7.67 (dt, J=8.1, 2.0 Hz, 1H), 7.60 (t, J=7.8 Hz, 1H), 7.44 (d, J=8.3 Hz, 1H), 7.37-7.32 (m, 3H), 7.30 (dt, J=8.2, 2.0 Hz, 1H), 7.27-7.22 (m, 1H), 7.16 (t, J=7.6 Hz, 1H), 7.08 (d, J=8.2 Hz, 1H), 6.95 (d, J=7.6 Hz, 2H), 6.53 (dd, J=15.5, 1.0 Hz, 1H), 5.49 (dd, J=11.6, 4.3 Hz, 1H), 3.86-3.73 (m, 4H), 3.03 (dd, J=18.6, 4.2 Hz, 1H).

5-(3-(6-Chloro-2-oxo-4-phenyl-1,2-dihydroquinolin-3-yl)-5-(4-nitrophenyl)-4,5-dihydro-1H-pyrazol-1-yl)-5-oxopentanoic acid (63) (997-4, GluN2D-29). Compound 63 was prepared according to general procedure G using dihydro-2H-pyran-2,6(3H)-dione (0.077 g, 0.67 mmol) and 63f (0.30 g, 0.67 mmol). The title compound was obtained after being dissolved in hot EtOAc followed by slow addition of hot hexanes to yield the title compound as a yellow solid. Yield 0.220 g, 58%. $^1$H NMR (400 MHz, DMSO-$d_6$) δ 12.44 (s, 1H), 12.12 (s, 1H), 8.12 (d, J=8.3 Hz, 2H), 7.70-7.51 (m, 4H), 7.51-7.38 (m, 2H), 7.28 (d, J=6.6 Hz, 1H), 7.07 (d, J=8.5 Hz, 2H), 6.95 (d, J=2.5 Hz, 1H), 5.50 (dd, J=12.3, 4.8 Hz, 1H), 3.83 (dd, J=18.6, 12.2 Hz, 1H), 2.86 (dd, J=18.6, 4.9 Hz, 1H), 2.45-2.30 (m, 1H), 2.29-2.17 (m, 1H), 2.13 (t, J=7.4 Hz, 2H), 1.65-1.45 (m, 2H).

5-(3-(4-(4-Bromophenyl)-2-oxo-1,2-dihydroquinolin-3-yl)-5-(4-chlorophenyl)-4,5-dihydro-1H-pyrazol-1-yl)-5-oxopentanoic acid (61) (997-32, GluN2D-192). Compound 61 (997-32) was prepared according to general procedure G using dihydro-2H-pyran-2,6(3H)-dione (0.071 g, 0.63 mmol) and 22f (0.30 g, 0.63 mmol). Upon completion, the THF was removed under vacuum and the residue was dissolved in hot EtOAc. Upon cooling, a yellow solid formed which was filtered, dried under vacuum and determined to be to desired product. Yield 0.200 g, 55%. $^1$H NMR (400 MHz, DMSO-d6) δ 12.29 (s, 1H), 12.09 (s, 1H), 7.77 (dd, J=8.2, 2.1 Hz, 1H), 7.70 (dd, J=8.2, 2.1 Hz, 1H), 7.58 (t, J=7.7 Hz, 1H), 7.43 (d, J=8.3 Hz, 1H), 7.36 (dd, J=8.2, 2.2 Hz, 1H), 7.34-7.28 (m, 2H), 7.23 (dd, J=8.1, 2.3 Hz, 1H), 7.15 (t, J=7.6 Hz, 1H), 7.04 (d, J=8.2 Hz, 1H), 6.86-6.76 (m, 2H), 5.36 (dd, J=12.0, 4.4 Hz, 1H), 3.81-3.68 (m, 1H), 2.80 (dd, J=18.7, 4.3 Hz, 1H), 2.40 (dt, J=15.3, 7.4 Hz, 1H), 2.29-2.06 (m, 3H), 1.68-1.51 (m, 2H).

4-(4-Chlorophenyl)-3-(5-(4-chlorophenyl)-1-(4-hydroxybutanoyl)-4,5-dihydro-1H-pyrazol-3-yl)quinolin-2

(1H)-one (64) (997-57, GluN2D-394). In a flame dried 25 mL round bottomed flask, 4-26 (0.300 g, 0.560 mmol) was dissolved in THF (10 mL) and cooled on an ice bath to 0° C. under nitrogen and with stirring. BH$_3$-DMS (2.0M in Hexanes, 0.561 ml, 2 eq.) was added dropwise. The reaction was stirred for thirty minutes, quenched with MeOH and the solvent removed under vacuum. The resultant residue was dissolved in DCM, washed three times with brine and the organics combined, dried over magnesium sulfate, concentrated in vacuo and column chromatographed using a 0-8% gradient of MeOH in DCM to give the title compound as a yellow solid. Yield 0.063 g, 22%. $^1$H NMR (400 MHz, DMSO-d$_6$) δ 12.29 (s, 1H), 7.65-7.49 (m, 3H), 7.46-7.24 (m, 5H), 7.20-7.00 (m, 2H), 6.89-6.78 (m, 2H), 5.35 (dd, J=12.0, 4.4 Hz, 1H), 4.45 (t, J=5.2 Hz, 1H), 3.74 (dd, J=18.5, 12.1 Hz, 1H), 3.41-3.27 (m, 2H), 2.80 (dd, J=18.5, 4.5 Hz, 1H), 2.44-2.19 (m, 2H), 1.59-1.39 (m, 2H).

4-(5-(4-Chlorophenyl)-3-(4-(4-chlorophenyl)-2-oxo-1,2-dihydroquinolin-3-yl)-4,5-dihydro-1H-pyrazol-1-yl)-4-oxobutanamide (65) (997-58, GluN2D-397). In a flame dried 25 mL round bottomed flask, 26 (0.300 g, 0.560 mmol), 4-dimethylaminopyridine (0.069 g, 0.560 mmol) and N1-((ethylimino)methylene)-N3,N3-dimethylpropane-1,3-diamine (0.096 g, 0.618 mmol) were added to THF (11.23 mL) at 0° C. and stirred for 45 minutes. Ammonia (0.5 M in dioxane, 1.0 eq, 1.1 ml) was added to the flask and the reaction mixture was stirred overnight while being allowed to warm to room temperature. The reaction was quenched with dilute HCl (0.1 M) and the organics were removed under vacuum. The resultant residue was dissolved in DCM, washed 3× with brine and the organics dried over magnesium sulfate and concentrated in vacuo prior to column chromatography using a 0-8% MeOH gradient in DCM (0.1% Et$_3$N). The title compound was obtained as a white solid. Yield 0.019 g, 6.4%. $^1$H NMR (400 MHz, DMSO-d$_6$) δ 12.29 (s, 1H), 7.66-7.56 (m, 2H), 7.55-7.49 (m, 1H), 7.43 (d, J=8.4 Hz, 2H), 7.28 (dd, J=8.2, 4.4 Hz, 3H), 7.24 (s, 1H), 7.15 (t, J=7.6 Hz, 1H), 7.03 (d, J=8.2 Hz, 1H), 6.79 (d, J=8.5 Hz, 2H), 6.73 (s, 1H), 5.34 (dd, J=12.1, 4.5 Hz, 1H), 3.71 (dd, J=18.4, 12.2 Hz, 1H), 2.72 (dd, J=18.4, 4.5 Hz, 1H), 2.59-2.50 (m, 2H), 2.20 (t, J=7.2 Hz, 2H).

Methyl 4-(5-(4-chlorophenyl)-3-(4-(4-chlorophenyl)-2-oxo-1,2-dihydroquinolin-3-yl)-4,5-dihydro-1H-pyrazol-1-yl)butanoate (66) (glun2d-453, 997-62). In a 20 mL round-bottomed flask, 26f (0.500 g, 1.151 mmol) and methyl 4-oxobutanoate (0.121 ml, 1.151 mmol) were dissolved in DCE (11.51 ml). The mixture was allowed to stir at room temperature for four hours and sodium triacetoxyborohydride (0.293 g, 1.381 mmol) was added in one portion. The reaction was monitored by TLC and HPLC-MS. Upon completion, the DCE was removed under vacuum, the residue diluted with DCM and washed 3× with brine. The organics were concentrated and the title compound was obtained from flash column chromatography using 0-10% MeOH in DCM and trituration of the compound from ether as a yellow solid. Yield 0.150 g, 24.4%. $^1$H NMR (400 MHz, CDCl$_3$) δ 12.22 (s, 1H), 7.55-7.45 (m, 3H), 7.40 (s, 1H), 7.34-7.26 (m, 5H), 7.22 (s, 2H), 7.13 (t, J=7.6 Hz, 1H), 4.11 (dd, J=13.6, 10.1 Hz, 1H), 3.62 (s, 3H), 3.41 (dd, J=16.4, 10.1 Hz, 1H), 2.91-2.78 (m, 1H), 2.70-2.53 (m, 2H), 2.30-2.08 (m, 2H), 1.84-1.66 (m, 2H).

4-(5-(4-Chlorophenyl)-3-(4-(4-chlorophenyl)-2-oxo-1,2-dihydroquinolin-3-yl)-4,5-dihydro-1H-pyrazol-1-yl)butanoic acid (67) (Glun2d-455, 997-63). In a 10 mL round-bottomed flask, compound 66 (0.100 g, 0.187 mmol) was dissolved in NaOH (0.711 ml, 0.711 mmol), H$_2$O (10.00 ml) and Ethanol (6.24 ml). The mixture was stirred at room temperature for four hours and monitored by TLC/LC-MS. Upon completion, HCl (0.711 ml, 0.711 mmol) was added, giving a bright yellow solid which was filtered, dissolved in DCM and washed 3× with acidified (pH 2, HCl) brine. The organics were combined, dried over magnesium sulfate and concentrated in vacuo. The title compound was obtained by flash chromatography using 0-8% MeOH in DCM. Yield 0.050 g, 51%. $^1$H NMR (600 MHz, DMSO-d$_6$) δ 12.16 (s, 1H), 11.92 (s, 1H), 7.54 (tt, J=6.4, 3.0 Hz, 4H), 7.47-7.27 (m, 6H), 7.17-7.01 (m, 2H), 4.03 (dd, J=13.8, 10.2 Hz, 1H), 3.33 (dd, J=16.4, 10.2 Hz, 1H), 2.73 (dd, J=16.5, 13.8 Hz, 1H), 2.50 (p, J=7.8 Hz, 1H), 2.35 (ddd, J=12.1, 7.4, 4.7 Hz, 1H), 2.12-1.96 (m, 2H), 1.55-1.39 (m, 2H).

4-(4-Chlorophenyl)-3-(5-(4-chlorophenyl)-1-(4-fluorobutanoyl)-4,5-dihydro-1H-pyrazol-3-yl)quinolin-2(1H)-one (68) (GluN2D-471, 997-64). In a 10 mL round-bottomed flask, 4-fluorobutanoic acid 68 g (0.100 g, 0.943 mmol), DMAP (0.127 g, 1.037 mmol) and EDCI (0.199 g, 1.037 mmol) were dissolved in DCM (9.43 ml) which had been pre-cooled to 0° C. The mixture was stirred for 45 minutes prior to the addition of the 26f (0.409 g, 0.943 mmol). The reaction was allowed to warm to room temperature, and monitored by TLC. The reaction was quenched with 0.2 N HCl and extracted into DCM. The organics were washed 3× with brine, dried over magnesium sulfate and concentrated. The title compound was obtained as a yellow solid after column chromatography using a gradient of 0-50% EtOAc in DCM as a yellow solid. Yield 0.050 g, 22%. $^1$H NMR (400 MHz, CDCl$_3$) δ 13.16 (s, 1H), 7.62-7.43 (m, 4H), 7.38 (d, J=8.2 Hz, 1H), 7.34-7.16 (m, 5H), 7.02 (d, J=8.3 Hz, 2H), 5.42 (dd, J=11.8, 4.0 Hz, 1H), 4.44 (dtd, J=47.3, 5.8, 1.7 Hz, 2H), 3.70 (dd, J=18.2, 11.8 Hz, 1H), 3.15 (dd, J=18.3, 4.1 Hz, 1H), 2.68-2.45 (m, 2H), 2.18-1.82 (m, 2H).

The invention claimed is:
1. A compound having a structure of Formula I or a salt or ester thereof:

Formula I

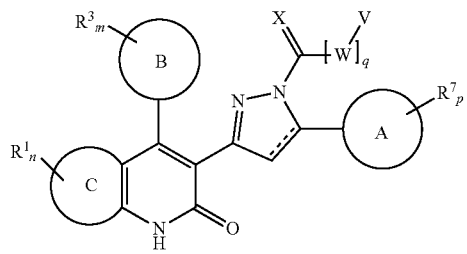

wherein:
rings A, B, and C are each individually and independently aryl, cycloalkyl, or heterocyclyl;
the dotted line represents a single bond or no bond;
n, m, and p are each individually and independently 0, 1, 2, 3, or 4;
q is 1;
W is CF$_2$CH$_2$, CH$_2$CF$_2$, or CH=CH;
V is (C=Y)Z;
X and Y are each individually and independently O, S, NH, N-alkyl, two hydrogens each singly bonded to the adjacent carbon, or two fluoros each singly bonded to the adjacent carbon;

Z is halogen, OH, O-alkyl, O-alkanoyl, $NH_2$, NH-alkyl, NH-alkanoyl, SH, S-alkyl, or S-alkanoyl, wherein Z is optionally substituted with one or more the same or different $R^{10}$;

$R^1$, $R^3$, and $R^7$ are at each occurrence individually and independently hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^3$, and $R^7$ are at each occurrence individually and independently optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein m is 1.

3. The compound of claim 1, wherein n is 0.

4. The compound of claim 1, wherein p is 1.

5. The compound of claim 1, wherein rings A, B, and C are each phenyl.

6. The compound of claim 5, wherein ring A is para-substituted with halogen, nitro, or trifluoromethyl.

7. The compound of claim 6, wherein ring A is para-substituted with chloro.

8. The compound of claim 5, wherein ring B is para-substituted with halogen, methyl, methoxy, cyano, or trifluoromethyl.

9. The compound of claim 8, wherein ring B is para-substituted with chloro.

10. The compound of claim 1, wherein W is $CH_2CF_2$ or $CF_2CH_2$.

11. The compound of claim 1, wherein X is O.

12. The compound of claim 1, wherein Y is O.

13. The compound of claim 1, wherein:
rings A, B, and C are each phenyl;
W is $CH_2CF_2$ or $CF_2CH_2$; and
X and Y are each O.

14. The compound of claim 1, wherein the compound has a structure of Formula IA or a salt or ester thereof:

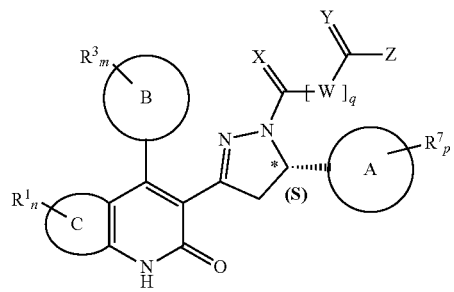

Formula IA wherein ring A, ring B, ring C, W, X, Y, Z, $R^1$, $R^3$, $R^7$, m, n, p, and q are the same as those described in claim 1.

15. The compound of claim 1, selected from:
4-(4-chlorophenyl)-3-(5-(4-chlorophenyl)-1-(3,3-difluoro-4-hydroxybutanoyl)-4,5-dihydro-1H-pyrazol-3-yl) quinolin-2 (1H)-one,
(S)-4-(4-chlorophenyl)-3-(5-(4-chlorophenyl)-1-(3,3-difluoro-4-hydroxybutanoyl)-4,5-dihydro-1H-pyrazol-3-yl) quinolin-2 (1H)-one,
(R)-4-(4-chlorophenyl)-3-(5-(4-chlorophenyl)-1-(3,3-difluoro-4-hydroxybutanoyl)-4,5-dihydro-1H-pyrazol-3-yl) quinolin-2 (1H)-one,
4-(4-chlorophenyl)-3-(5-(4-chlorophenyl)-1-(2,2-difluoro-4-hydroxybutanoyl)-4,5-dihydro-1H-pyrazol-3-yl) quinolin-2 (1H)-one,
3-(5-(4-chlorophenyl)-1-(3,3-difluoro-4-hydroxybutanoyl)-4,5-dihydro-1H-pyrazol-3-yl)-4-(3-fluorophenyl) quinolin-2 (1H)-one,
4-(5-(4-chlorophenyl)-3-(4-(4-chlorophenyl)-2-oxo-1,2-dihydroquinolin-3-yl)-4,5-dihydro-1H-pyrazol-1-yl)-3,3-difluoro-4-oxobutanoic acid,
4-(5-(4-chlorophenyl)-3-(4-(3-fluorophenyl)-2-oxo-1,2-dihydroquinolin-3-yl)-4,5-dihydro-1H-pyrazol-1-yl)-2,2-difluoro-4-oxobutanoic acid,
methyl 4-(5-(4-chlorophenyl)-3-(4-(4-chlorophenyl)-2-oxo-1,2-dihydroquinolin-3-yl)-4,5-dihydro-1H-pyrazol-1-yl)-2,2-difluoro-4-oxobutanoate,
(S)-4-(5-(4-chlorophenyl)-3-(4-(4-chlorophenyl)-2-oxo-1,2-dihydroquinolin-3-yl)-4,5-dihydro-1H-pyrazol-1-yl)-2,2-difluoro-4-oxobutanoic acid,
4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoic acid,
(Z)-4-(5-(4-bromophenyl)-3-(6-chloro-2-oxo-4-phenyl-1,2-dihydroquinolin-3-yl)-4,5-dihydro-1H-pyrazol-1-yl)-4-oxobut-2-enoic acid,
(E)-4-(5-(4-bromophenyl)-3-(6-chloro-2-oxo-4-phenyl-1,2-dihydroquinolin-3-yl)-4,5-dihydro-1H-pyrazol-1-yl)-4-oxobut-2-enoic acid,
(Z)-4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoic acid,
(E)-4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoic acid,
(S,E)-4-(3-(4-(4-bromophenyl)-2-oxo-1,2-dihydroquinolin-3-yl)-5-(4-chlorophenyl)-4,5-dihydro-1H-pyrazol-1-yl)-4-oxobut-2-enoic acid,
(S,E)-4-(5-(4-chlorophenyl)-3-(4-(4-chlorophenyl)-2-oxo-1,2-dihydroquinolin-3-yl)-4,5-dihydro-1H-pyrazol-1-yl)-4-oxobut-2-enoic acid, and
salts or esters thereof.

16. A composition comprising the compound of claim 14, wherein the compound is in greater than 95% enantiomeric excess for the S configuration, with respect to the stereocenter labeled by the * sign, as depicted in Formula IA.

17. A pharmaceutical formulation comprising a compound of claim 1 and a pharmaceutically acceptable excipient.

18. The pharmaceutical formulation of claim 17, wherein the pharmaceutical formulation is in the form of an oral formulation.

19. A method of treating or preventing a cognitive, psychiatric, or neurodegenerative disease or condition in a subject in need thereof, comprising administering to the subject a compound of claim 1.

20. The method of claim 19, wherein the disease or condition is cognitive impairment, neurodegenerative disease, pain, depression, schizophrenia, attention deficit hyperactivity disorder, ischemia, or addiction.

21. The method of claim 20, wherein the neurodegenerative disease is Alzheimer's disease, mild cognitive impairment, or Parkinson's disease.

22. A method of treating or preventing a disease or condition in a subject in need thereof, comprising administering to the subject a compound of claim 1, wherein the disease or disorder is stroke, traumatic brain injury, brain tumor, multiple sclerosis, or epilepsy.

* * * * *